(12) United States Patent
Ng

(10) Patent No.: US 7,101,668 B2
(45) Date of Patent: Sep. 5, 2006

(54) MOLECULAR MARKERS

(75) Inventor: Wee Chit Ng, Singapore (SG)

(73) Assignee: National University of Singapore, Singapore (SG)

( * ) Notice: Subject to any disclaimer, the term of this patent is extended or adjusted under 35 U.S.C. 154(b) by 277 days.

(21) Appl. No.: 10/240,689

(22) PCT Filed: Apr. 17, 2001

(86) PCT No.: PCT/SG01/00067

§ 371 (c)(1),
(2), (4) Date: Sep. 30, 2002

(87) PCT Pub. No.: WO01/79545

PCT Pub. Date: Oct. 25, 2001

(65) Prior Publication Data

US 2003/0175743 A1    Sep. 18, 2003

(51) Int. Cl.
*C12Q 1/68* (2006.01)

(52) U.S. Cl. ............................................. 435/6
(58) Field of Classification Search ............... 435/6, 435/91.1, 91.2; 536/23.1
See application file for complete search history.

(56) References Cited

FOREIGN PATENT DOCUMENTS

| AU | 721826 | 7/2000 |
|----|--------|--------|
| EP | 0669399 | 8/1995 |
| WO | 98/39473 | 9/1998 |

OTHER PUBLICATIONS

Blattner et al. The complete genome sequence of *Escherichia coli* K-12. 1997. Science vol. 277:1453-1462.*
Swidsinski et al. Association between intraepithelial *Escherichia coli* and colorectal cancer. 1998. Gastroenterology vol. 115:281-286.*
Oshima et al. DNA Research vol. 3:137-155. 1996.*
Buck et al. Biotechniques vol. 27:528-536. 1999.*
Blattner, et al., "The Complete Genome Sequence of *Escherichia coli* K-12", *Science*, 1997, vol. 277, pp. 1453-1462.
Swidsinski, et al., "Association Between Intraepithelial *Escherichia coli* and Colorectal Cancer," *Gastroenterology*, 1998, vol. 115, pp. 281-286.

* cited by examiner

*Primary Examiner*—Gary Benzion
*Assistant Examiner*—Heather G. Calamita
(74) *Attorney, Agent, or Firm*—Klarquist Sparkman, LLP

(57) ABSTRACT

Nucleic acid based methods for detecting the presence of *E. coli* or *Shigella* or related microorganisms in a sample using one or more *E. coli* or *Shigella* species specific nucleotide sequences are disclosed. More particularly the identification of molecules capable of binding or otherwise facilitating abnormal cell growth or abnormal physiology such as found in cancer or cellular instability is described. Further, molecular probes for performing the nucleic-acid based methods and methods of testing and selecting nucleic acid sequences suitable for same are provided. The methods and polynucleotides are useful inter alia in the testing of food and water samples, for testing for genetic and cellular instability, and for testing benign, pre-neoplastic and neoplastic disease in asymptomatic or symptomatic colorectal or gastric cancer patients or those at risk of the aforementioned conditions or those infected by Escherichieae and with other diseases or conditions.

22 Claims, 40 Drawing Sheets

GenBank accession number : AE 000203 (10751 bp)

Fragment 4 : 6073 (AE 000202) - 503

*9731 - 503

* of AE 000202 MAP

5944 - 6693

Equivalence to 1000 bp

Figure 1c

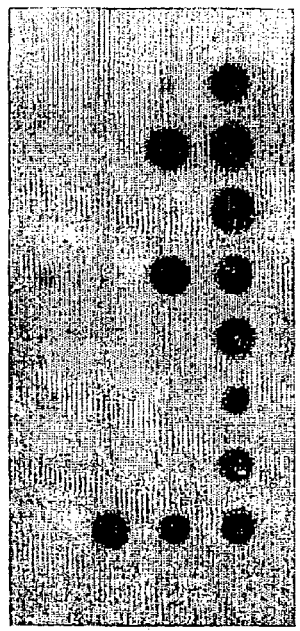
Fig 2. Grid C
Probe A
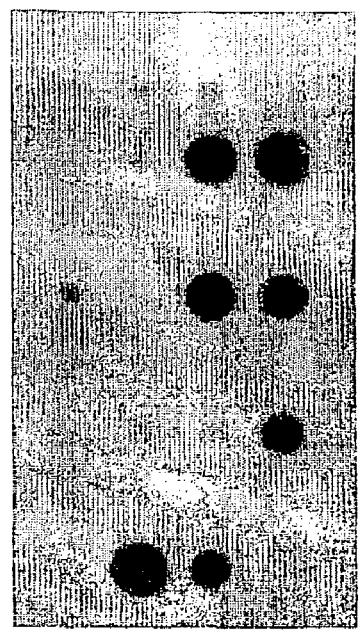
Fig 3. Grid A
Primers: ECM-246, ECM-850
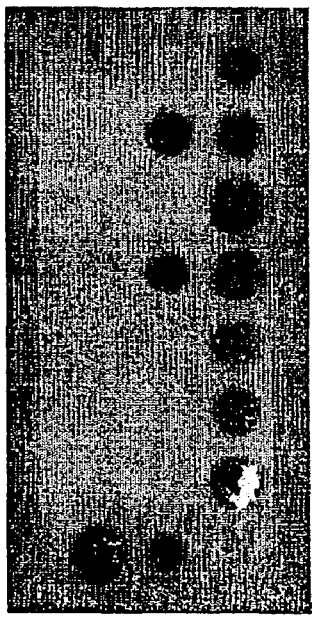
Fig 4. Grid B
Primers: ECM-1163, ECM-1958
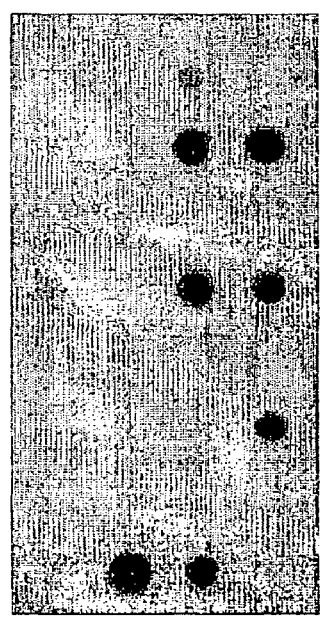
Fig 5. Grid A
Primers: tor C-7218, tor C-7761
Autoradiographs of dot blot hybridization result on panel of bacteria DNA.

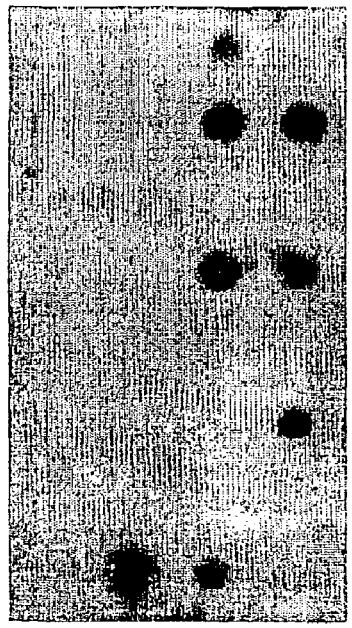
Fig 6. Grid A
Primers: tor A-8332, tor A 8891
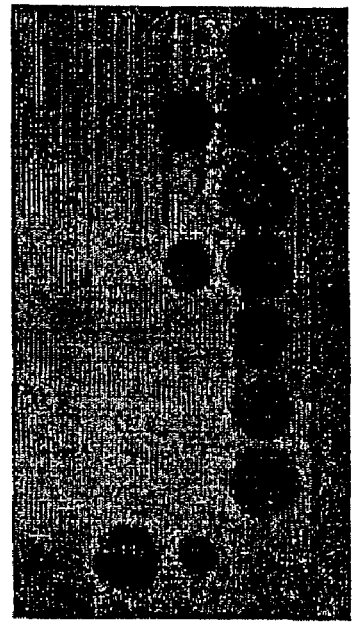
Fig 7. Grid B
Primers: tor D-10574, tor D-11160
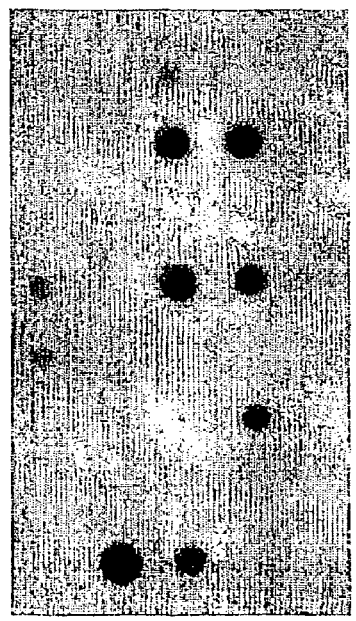
Fig 8. Grid A
Primers: CD-415, CD-1351
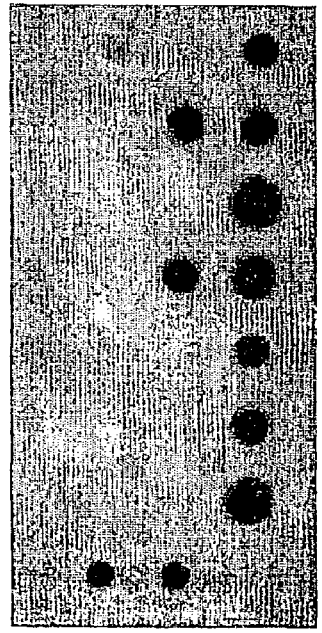
Fig 9. Grid B
Primers: agp-3151, agp-4359
Autoradiographs of dot blot hybridization result on panel of bacteria DNA.

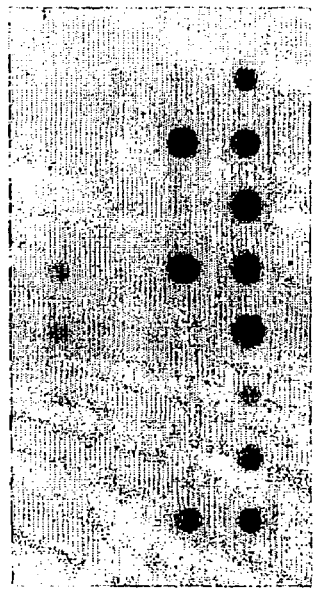
Fig 10. Grid C
Primers: Wrb-4807, Wrb-5235
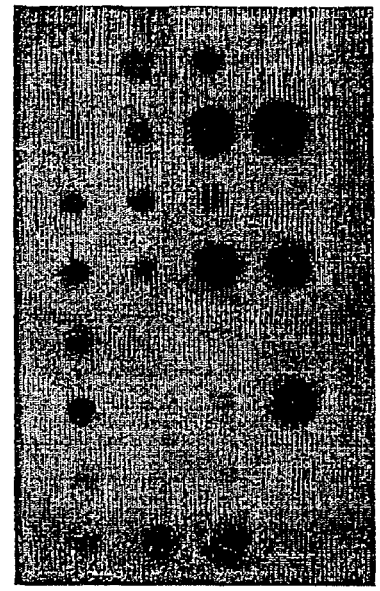
Fig 11. Grid A
Primers: ycdG-6073, ycdG-7359
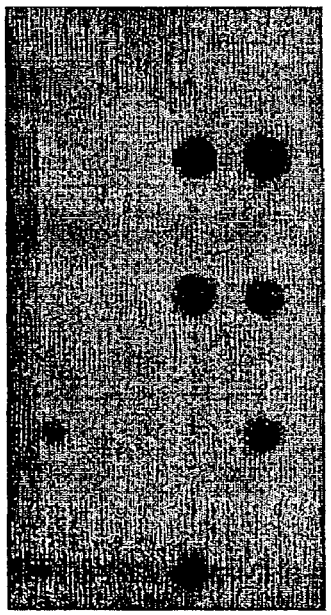
Fig 12. Grid A
Primers: 81B-7223, 81B-7794
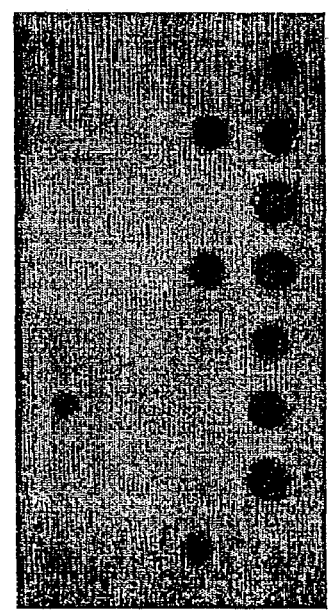
Fig 13. Grid B
Primers: 81B-7278, 81B-7754
Autoradiographs of dot blot hybridization result on panel of bacteria DNA.

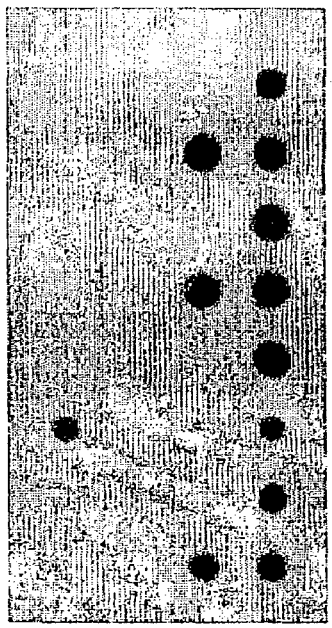
Fig 14. Grid C
Primers: OH-7419, OH-7985
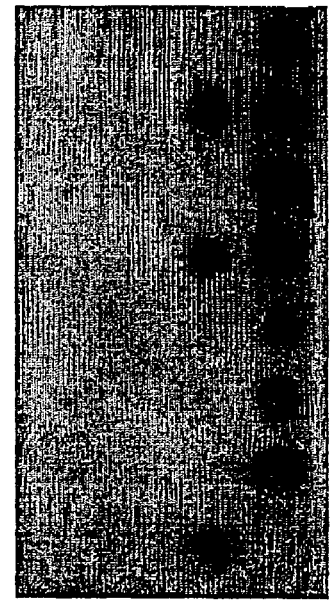
Fig 15. Grid B
Primers: OH-7562, 81B-7794
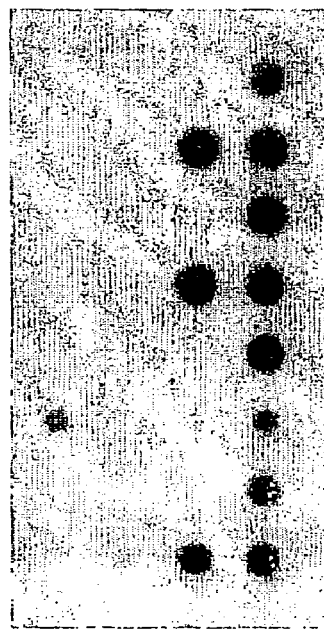
Fig 16. Grid C
Primers: New1-8160, New1-9704
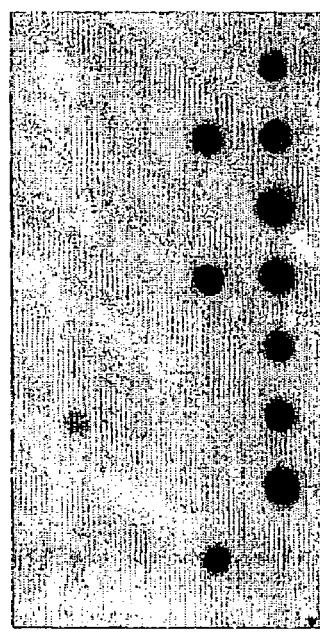
Fig 17. Grid B
Primers: New2-9731, B-11375
Autoradiographs of dot blot hybridization result on panel of bacteria DNA.

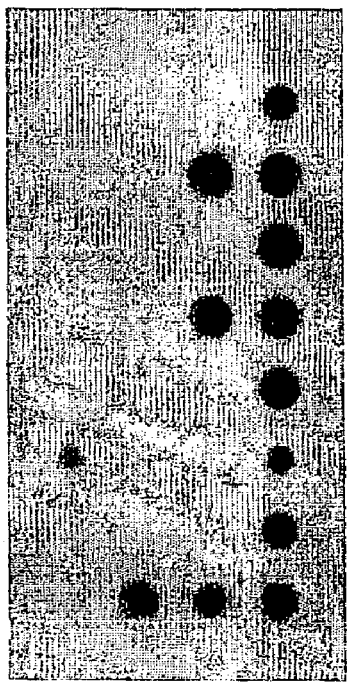 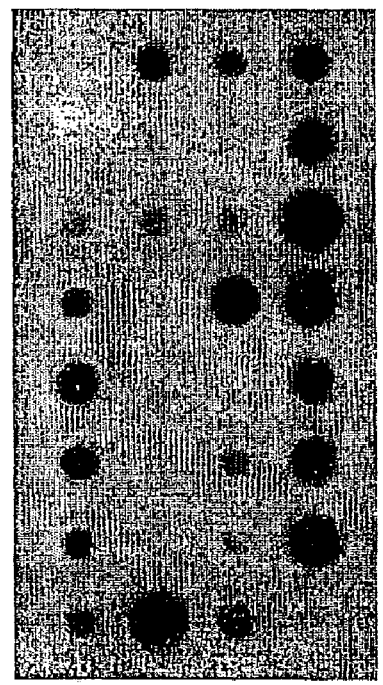
Fig 18. Grid C   Fig 19. Grid B
Primers: New2-9731, New2-503   Primers: putP-5944, putP-6693
Autoradiographs of dot blot hybridization result on panel of bacteria DNA.

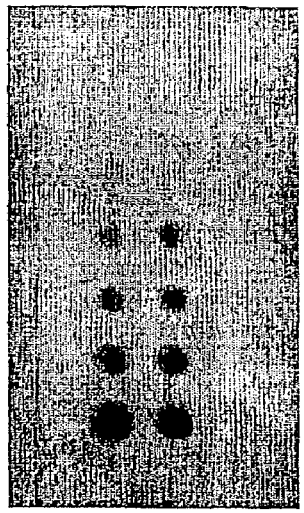
Fig 20. Grid E
Probe A
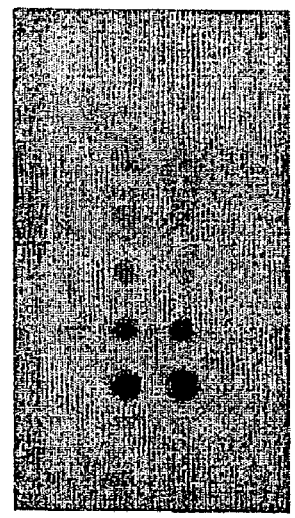
Fig 21. Grid E
Primers: OH-7562 & 81B-7794
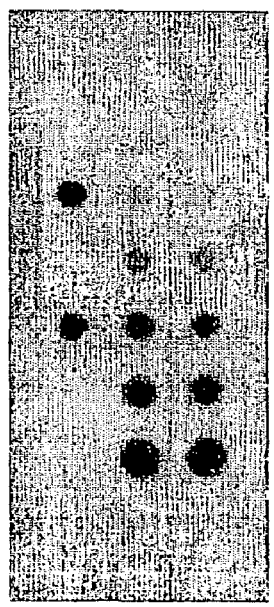
Fig 22. Grid E
Primers: 81B-7223 , 81B-7794
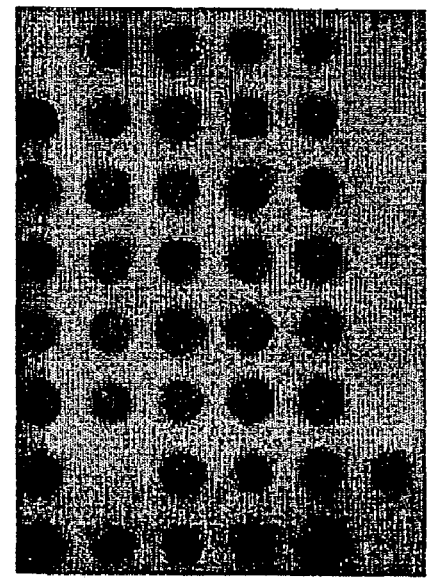
Fig 23. Grid D
Primers: 81B-7278 , 81B-7754
Autoradiographs of dot blot hybridization result on panel of bacteria DNA.

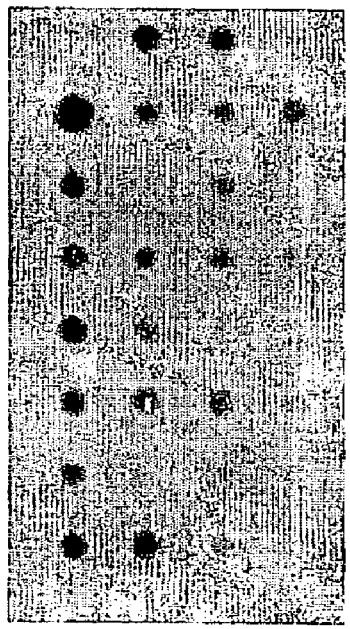 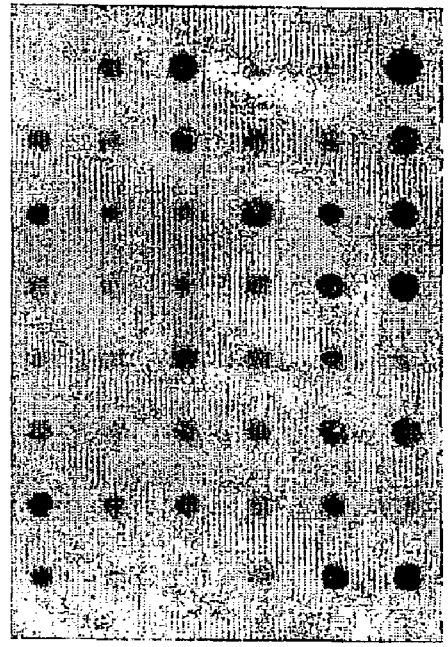
Fig 24. Grid A          Fig 25. Grid D
Primers: HP-228, HP-513     Primers: HP-228, HP-513
Autoradiographs of dot blot hybridization result on panel of bacteria DNA.

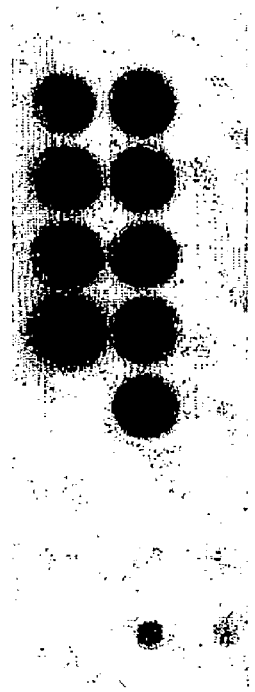
Fig 26. Grid F
Outer primers for PCR: HP-178, HP-775
Inner primers for generating probe: HP-228, HP-513
H. Pylori dot-blot hybridization result of in vitro simulated PCRISH

Figure 27
Insert

Figure 28
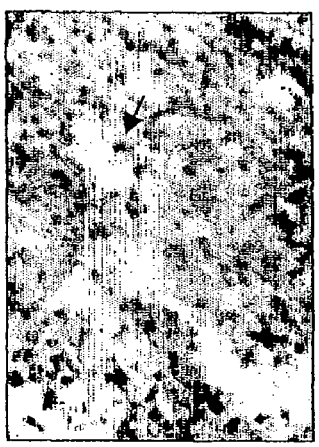
Insert

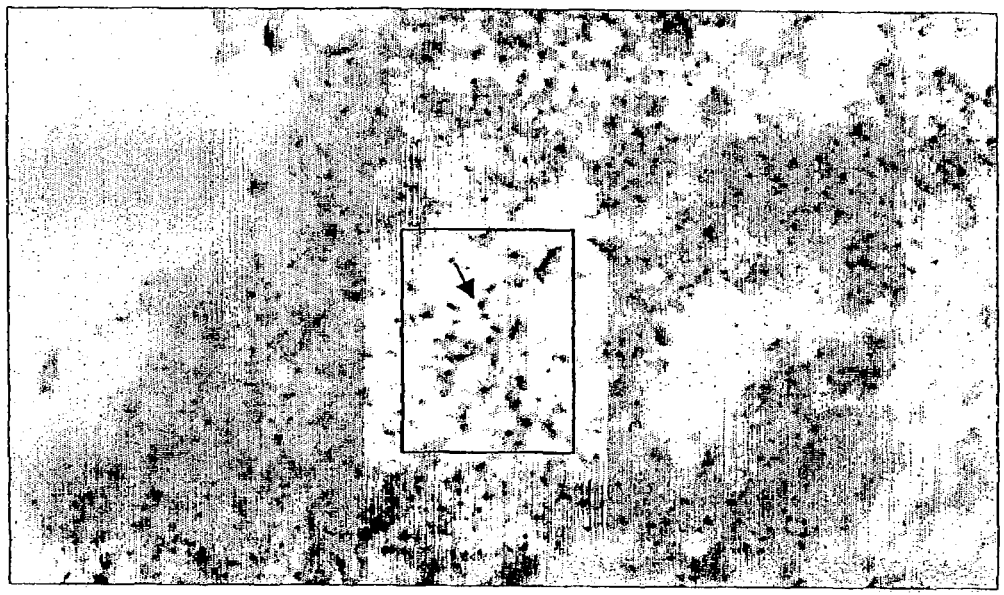
Figure 29
Insert

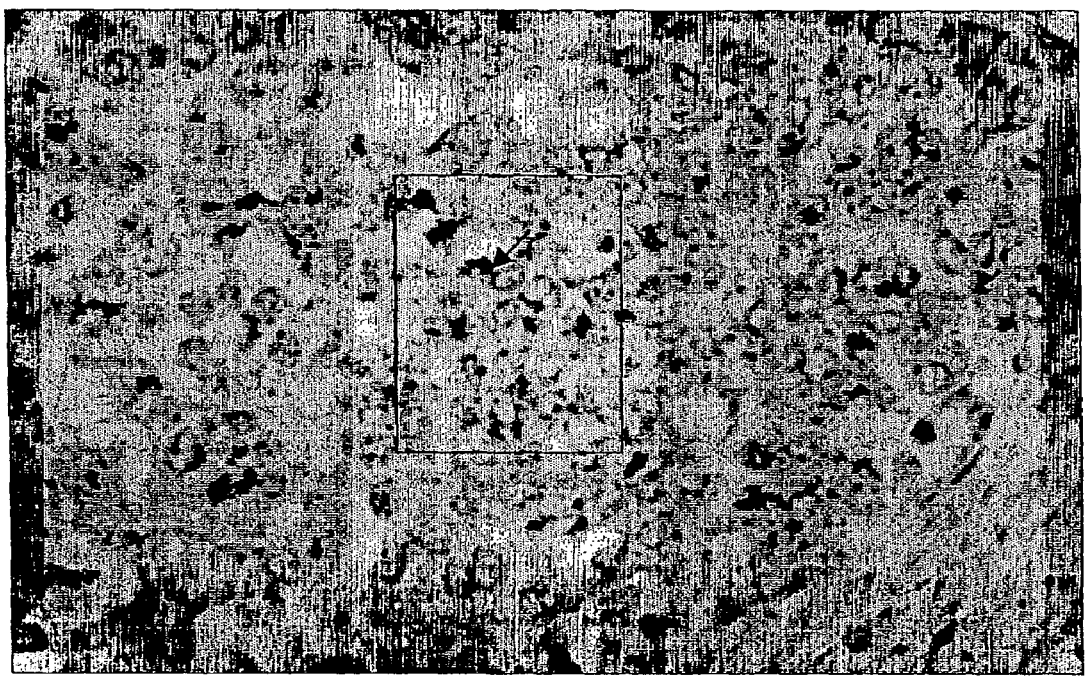
Figure 35
Insert

Figure 45
AE 000201 (Section 1)

```
   1 aagccagcga tatttaagac cgccggacgg ctaaataaa atttgcttaa tctcaattat
  61 catgcgttaa tagctgcgtc ggtttgaaag acagacagca tacaaagtag tttactaaag
 121 cagttctcat tatcaggcat tatcccttc ttttgagtct ctctcctgaa cactaagtag
 181 tttctgtatt aaagccctgt ttgccgaaag gcccaaaatg aaggaagtaa aatatgtcta
 241 ataaaatgac tggtttagta aaatggttta acgcagataa aggttttggc tttatcactc
 301 ctgatgatgg cagcaaagac gttttcgtcc atttcaccgc catccagagc aatgaattcc
 361 gcacgctgaa cgaaaatcag aaagttgaat tttctattga gcaggggcaa cgtggcccg
 421 cggcagcgaa cgttgttacg ctctaaggtt gccattatta ctcaacatct ccatttccgc
 481 tgtccatgtt gtcatggttc acagtaccgc acatcggcat tcgatgtgac ggagcgaaac
 541 cctttgggcg ctaagtgtat tttttgtaaa tcgacgatga tcacctttga taacgtcgcg
 601 ctgcaaatac gcactgacca tgcgccgctg gatttcacaa ataatatca ggctccctcg
 661 tggagccttt tttatatctg ccttatttt cttcaacgct gtatgtatag taagcgataa
 721 cctgttgatt attgaatctt tcggggagat ggcttataac atttcttacc tgaccagggt
 781 accgggaacc aacaccttac tggcgtgttg ctgtctttta agaccagaag aggttaacag
 841 tgaatattga agagtaaaa aaacaagccg aaacggaaat cgccgacttt atcgcgcaaa
 901 aaatcgccga gctgaacaag aatacaggga agaagtctc tgaaattcgc ttcaccgcac
 961 gagaaaaaat gaccgggctt gaaagttatg atgtcaaaat caaaataatg tgatttgtg
1021 aacatcaccc cgtgcgaggt gatgttccgc ttgttgctaa tttagtgacc aatcattggc
1081 gcttgtggaa ttaagcgtcg gtacaattcc tccggcaccg ggctttgcca tactcccgca
1141 tacattgcgt aaccaatcac cgcaaacata atcccagaa ccagtagcgt cattaaccag
1201 ccagacaacg caaaggcttt tttatttgcc gcaggttttt gcagtgaaaa ggtcaatgtt
1261 gaggctaccg gacatgactc tacgcaagtc atacagccgg tacattccac tgttcgtacc
1321 tgaattaatt tatcgaccgg gatccgtgat gggcaattt ttgcgcattt gccacagtcg
1381 atacaacttt cggcattgcg acgaatctta aacggcgaca atagcgaaac cacgcccatc
1441 agcgcgccat atgggcaaag ataacgacac caggcatggc gaataaacag gctggcaatc
1501 agcaaaacgg tcacgctgat taatgtcgcg gtccccatat gacgaaagaa atcgagcatt
1561 ttaacgtcca tcaccacgct gtagggcgac aacataaaat agtgaatcgc ctgagcgggc
1621 atcaataacg cgatatagat aaaaaaactc aacagcaaat acttcacgcc gcgcagagga
1681 atatccagcc agcggggaag gacacattgc cgaccaaaca gtttgttacc gagatcgccg
1741 attaattcag aaagcgtacc aaccgggcat aaccatgagc aaaaggcctt tttgagtaat
1801 agactgatga cgataaaagc gaccaataac agcatcgcgg cggcgtggac ggacggtaac
1861 tgacctgtta caaggctata tttcagattc atcagcccgg caatcggtag ccagccttcg
1921 atacctcccg gtctggcgac aaatgtcgtg ctacttgccg tttcgtaata gcgcacccaa
1981 taccagaacg tgatggcaat ataaatattc attgccaaca gtaataattg cgtcgcttta
2041 cgccaggtcg tggcattacg ccagtcattc cacggtaatt tgccgcccgt cgtgcctggc
2101 cgccgctgcc agcgggttct tttattctct gccatgattt tgccagtccg ttaagttgta
2161 taccaaatgc cactattcta gttgttctta actggctgat attgattcaa atcgcgttca
2221 ggtctttctt atgcaaccat gcttccagag cggcaacact gcgtgtaatt tcttcgtgtg
2281 gaagggggc agataatggc tgctgctcca gttgtgcgca tagctggctg gcgatatgca
2341 ttcccagact cgagcaactg ctttttagct gatgcgcggc acgctttatt ttctcgctat
2401 cctgactggc gcgggcaatg tcgatttcat cgagaagcgg cagggcatgt tgtgtaaata
2461 ataccagcca ttcgtggatc ttctccgtcc ccattaactg agcatcttca ttgagttgcg
2521 atacatccag cgattgatca ttattgactt gcagttggag atagtgcgcc agtaactgac
2581 cgagcacttc acgcggcacc ggtttaggga taatcccgcg gaataatgaa ctggtacgct
2641 ggcgcagcgt ttcgtcaatg acatgggcgc taaagccaat caaaaccagc gacggatatt
2701 gctgtgccag ttgtcgggca agcgtaatgc cgtcgatatc cggcagatca aaatccacca
2761 gtgcggcagc aaacggttcg ctattttgca gtgtctctaa agcctgcgcg gcattgccaa
2821 cagcaacaat ctgcgcacca ctggttttca gcatctcaat ggtaattcgc tgggttagcg
2881 ggttatcttc aattaacagc aaacgtaaac cgtcaagacg caccgcctga ttgactgttt
2941 ttggcacggg tgccgtggca acacgtaacg gcaagcgtaa acaaaaacag cttccaacct
3001 ccggcgtgct ggtggcgctc agttcgccgc ccatcgcctg gccagacgg ctactgatag
3061 tcagtcccag cccggtgccg ccgcgtttgc cgcttacctg cacaaatggc tggaagattt
3121 ctgccagttt cgcgggatca ataccgcagc cgctgtcttc cacttcgacc agccattgct
3181 cgccatcagt gcgactacgc aggataatgt acccttcgtc agtaaaacgc agggcgttgc
3241 tcaacaggtt ggttataacc tgacgaatac gtcgtggatc gcccattaac gcgcacggca
3301 tatcatcggc aattgccgtt gccaggcgaa tcggcgacc tttcacccgt ccgctcatta
3361 attgcagggt acttttccagc agcgggcgcg gttcaaaggg ctcatcgctg accgaaacat
3421 tcttgccacc tgcttcgata gcggaataat cgagaatatc gttgaggatg gtcagcaacg
```

```
3481 attcaccaga gtcagtaatt gcccgcaaat catcacgctg ggcgttaagt gcggggttat
3541 ctgccagcag ttgagcagtg ccgagaatac cgtacagcgg tgtgcggatc tcatggctca
3601 tcgccgccag aaacgccgat tttgcctggc tggcttttc tgcttccgcc cgtgcctgtc
3661 ggtgttctat caccagttcc tgcaattcag ctgtacgcgc tttgacctgc gccgccagct
3721 gttcgcggtg gcgattcagt gcatgaacat tgctgcgaaa cgcatccatc agccgcccga
3781 tggtatccag ctcccgtacg ccagcggttt ccgggaaagg ggagtcaata tcaccgtcca
3841 gcagccgttg cagcgcctgc gtttgttcgg caagtggacg cgtgactgag cgataaacca
3901 cgcgccagag gatcagaatc agtgcgcaaa gtgaaaccat ccccagcaat aacaggctgt
3961 attgcccgcg tgcactcgct ttttccagat gcgccagtcc gtgctgatta cgcagctcaa
4021 tggtgtcgac cagctgactg acttcgctac taaactgcgc gaactgggcg atgttatttt
4081 gtgcgagagt ttgtaggtga ttgctgattt cactgtcctg ctgatacagc gccagcaaat
4141 cgctatattg gctaacggta gttaacgttg ttgcgacctg cgcacgaaca cccggatctt
4201 caatgcgtat ttgccgacgt tgcagaattt tcaccgcatt attgagctgc ttttccagcg
4261 ttggtgcatt tttctggatc tgctccagcc ccagattcat caccatttgc tgcacccgca
4321 gagcgctaag gcgcagttca ttcatctggt taacatactc aagatcgata tcaatcagcc
4381 gatcgagtgc actttcagca gcctgacgct gatcttgttc gatcaaatcg taaatcccgg
4441 cctgggtcgc tccagcggaa gttgtcgcat tattcgcctg accttgcgcc aggcgtgcga
4501 tctcatcggc ggcagcgact atctgctgac tgagttgctg ttgttgctgg cgcagttgca
4561 aacgctgccc caccagttcc ccttgctgac gtaacgaacg ggagatctcc tgctcctgtt
4621 gttcaatagc ggtggtatca aaccttgtt cccgtaacgc ttgcagcaac gcattaatct
4681 tcaggctttg tgcggtgagc attcgcccct gcgcctgcca catcttttcg ttatcggcac
4741 tggtcaggtt ctgcgcggcg aaaagttccc aggcgctggc ttcgctcaac tggcgcgcca
4801 tattcatggt aggaatcaat gcctgagtgt tgtctttttc cacctggctg ataaagcgca
4861 ggttgtacca tcccaccagg gtactggtca gggttaacag cgccatcagg gcaaagccca
4921 tccagagtct tcgggtcagg gttaaattca cggtcggtgc actttaggtg aaaaaggttg
4981 agtcgcaaag cggaatgcat ctagcataaa gccttattat tgatgaggct atcatgcgcg
5041 tactgctatt tttacttctt tccctttca tgttccggc atttcggct gataacctgt
5101 tgcgctggca tgatgcgcag catttcacgg tgcaagcctc tacgccgctt aaagccaaac
5161 gcgcatggaa actgtgcgcg ctttatccca gcctgaaaga ttcatattgg ttatcgttga
5221 actatggtat gcaggaggct gctcgccgct acggtgtgga tttaaaagtg ctggaggcag
5281 gcggctacag ccagttggct accagcaag cacaaatcga ccagtgtaaa cagtggggcg
5341 cagaggccat tttgctcggt agtagcacga cctcatttcc cgacctgcaa aagcaggtag
5401 caagtctgcc ggtgatcgaa ctggtaaatg ctattgatgc tccccaggtg aaaagccgcg
5461 ttggtgtgcc ctggtttcag atgggctatc aaccggggcg atatctggtg caatgggcgc
5521 acggtaaacc actgaatgtg ctgttgatgc ccggacccga taacgccggg ggcagtaagg
5581 agatggtcga aggttttcgc gcagccattg ccggaagccc ggtgcgtatt gttgatattg
5641 cgcttggtga taacgatatt gaaatccagc gtaacctgtt gcaggagatg ctggaacgcc
5701 atccagaaat cgacgtcgtt gccggaacgg ccattgcggc agaggcggca atggggaag
5761 ggcgtaacct gaaaacgccg cttaccgtgg tgtcgtttta tctttcacat caggtgtatc
5821 gcgggctgaa gcggggaaga gtgattatgg ctgccagcga tcaaatggtc tggcaggggg
5881 aactggcggt tgagcaggcc atcaggcaat tacagggggca atcggtttct gataatgtca
5941 gcccaccgat tttagttctg acgccgaaaa atgccgaccg tgaacatatt cgccgctcgc
6001 tgtcaccagg gggatttcgt ccggtctatt tttatcagca cacatcagcg gctaagaaat
6061 aaccttcacc atgttgcgtc accagtaaat ccgcgctgag tttatgacgt aaacgacgaa
6121 ttaacacatc gacggtgcgc aggtcagggt tttccacccg acgcgcagaa agcatacgta
6181 gcagacgttc acggctgaga atttcgcccg gattcgtcac aaatgccacc aacatttcat
6241 actctgcgcg ggtcagttta atcggctcgc catcccgctc cagcgtatgg cgcgacacat
6301 tcaggcaata accggcaaag cgatagcagt tgtcctgagt gtgcggttga gcttgtcgcg
6361 cgaggtcgat tcgccagagc agatttttca cccgtactac cagttcgcgc agttccagcg
6421 gtttggtgac gtaatcgtct gcgcccattt ccagcccaac aatacggtca atccgatcgc
6481 tgcgtccggt aaccagaata atccccaccg ttgagcgttc tcgcagggcg cgggttaaca
6541 tcaggccatt tcatcgggt aagttgatat ccagcagaat taaatctacc gactgattct
6601 gcataatttc ccgtagccca gcaccgctcg ccgtaacgga aacggtatac ccctcctgag
6661 tgaagtagga ttgtaatcgc gcctgggtaa ccggctcatc ttcaacaata acaatgtgat
6721 gtggcatcag agggttttac tcattctgtt catatctgtt catattctgc cgtaagccgt
6781 tcatcctgac cagtgccgct gttcatattt gctcattaag atcgcttcac taaaccataa
6841 ttctacaggg gttattatgc ggaaactctg aacgcgcta cgccgaccca gtgctcgttg
6901 gtcggtactg gcgctggtcg caattgggat tgtgattggc attgcgctga ttgtattgcc
6961 acacgttggg atcaaagtca ccagcacaac cgaattttgt gtcagttgcc acagtatgca
7021 accggtgtat gaagaatata aacagtcggt gcatttccag aacgcctccg gcgtgcgagc
7081 tgaatgccat gactgtcata tcccgccgga tattccaggc atggtgaagc gcaaactgga
```

```
 7141 agcgagcaat gatatctacc agacctttat tgctcactcc attgatacac ctgaaaaatt
 7201 cgaagccaaa cgcgcggaac ttgccgagcg tgaatgggcg cgaatgaaag aaaacaactc
 7261 ggcaacctgc cgctcctgcc ataactacga tgcgatggat catgcgaagc agcatcctga
 7321 agcagcacgt cagatgaagg tggcagcgaa agataatcaa tcctgcatcg actgtcataa
 7381 aggtattgcc caccagttac cggatatgag tagcggcttc cgtaagcagt tcgatgagct
 7441 gcgcgccagt gctaatgaca gtggtgacac gctgtactct attgatatta agccaattta
 7501 tgcggcgaaa ggcgataaag aagcctctgg ttctctgctg cctgcttcgg aagtgaaagt
 7561 ccttaaacgt gacggcgact ggctgcaaat tgaaattacc ggctggacgg aaagcgccgg
 7621 acgtcagcgt gtactcaccc aattcccagg taaacgcatc tttgttgcct cgattcgtgg
 7681 tgatgtgcag cagcaggtaa aaacgctgga gaaaaccacc gttgccgaca ccaataccga
 7741 gtggagcaag ttgcaggcca ctgcgtggat gaagaaaggc gacatggtga acgatatcaa
 7801 accgatctgg gcttatgcgg attcgttgta caacggcacc tgtaaccagt gccacggcgc
 7861 accggaaatc gcccactttg acgctaacgg ttggctcggc acgctcaacg gcatgattgg
 7921 ctttaccagt ctcgataaac gtgaagaacg caccttgttg aaatatctgc aaatgaatgc
 7981 gtctgacacc gcaggtaagg ctcacggcga taagaaggaa gaaaaataat gaacaataac
 8041 gatctctttc aggcatcacg tcggcgtttt ctggcacaac tcggcggctt aaccgtcgcc
 8101 gggatgctgg ggccgtcatt gttaacgccg cgacgtgcga ctgcggcgca agcggcgact
 8161 gacgctgtca tctcgaaaga gggcattctt accgggtcgc actgggggc tatccgcgcg
 8221 acggtgaagg atggtcgctt tgtggcggca aaaccgttcg aactggataa atatccgtcg
 8281 aaaatgattg ccggattgcc ggatcacgta cacaacgcgg cgcgtattcg ttatccgatg
 8341 gtacgcgtgg actggctgcg taagcgccat ctcagcgata cctcccagcg cggtgataac
 8401 cgttttgtgc gcgtgagctg ggatgaagcc ctcgacatgt tctatgaaga actggaacgc
 8461 gtgcagaaaa ctcacgggcc gagtgccttg ctgaccgcca gtggttggca atcgacgggg
 8521 atgttccata acgcttcggg gatgctggcg aaagctattg ccttgcatgg taatagcgtt
 8581 ggtacgggcg gagattactc taccggtgct gcgcaggtga tcctgccgcg cgtagtcggt
 8641 tcgatggaag tgtatgaaca gcaaacctcc tggccgctgg tattgcagaa cagcaaaacc
 8701 attgtgctgt ggggctccga tttgctgaaa aaccagcaag cgaactggtg gtgcccggat
 8761 cacgatgttt atgaatatta cgcgcagcta aaagcgaaag tcgccgccgg tgaaattgag
 8821 gtcatcagca tcgatccggt tgtcacatcc acccatgagt atctggggcg cgagcatgtg
 8881 aagcacattg cggttaaccc gcaaactgac gtgccgctgc aactggcgct ggcacatacg
 8941 ctgtacagtg aaaacctgta cgacaaaaac ttccttgcta actactgtgt gggttttgag
 9001 cagttcctgc cgtatctgct gggtgagaaa gacggtcagc cgaaagatgc cgcatgggct
 9061 gaaaaactga ccggcattga tgccgaaacc attcgtgggc tggcgcggca gatgcggcg
 9121 aacagaacgc aaattattgc tggctggtgc gtgcagcgta tgcagcacgg taacagtgg
 9181 gcgtggatga ttgtggttct ggcggcgatg ctggggcaaa ttggcctgcc aggtggtgt
 9241 tttggttttg gctggcacta caacggcgca ggcacgccgg ggcgtaaagg cgttattctg
 9301 agtggtttct ccggctctac gtcgattccg cctgttcacg acaacagtga ctacaaaggc
 9361 tacagcagca ctattccgat tgcccgtttt atcgatgcga tcctcgaacc ggggaaagtg
 9421 atcaactgga acggtaaatc ggtaaaactg ccgccgctga aaatgtgtat ttttgccgga
 9481 actaacccat tccatcgcca tcagcagatc aaccgcatta ttgaaggctt gcgcaagctg
 9541 gaaacggtta tcgccataga taaccagtgg acctcaacct gccgctttgc cgatatcgta
 9601 ctgcctgcga ccacgcagtt tgagcgtaac gatctcgacc agtacggcaa tcactccaac
 9661 cgtggcatta tcgccatgaa acaggtggtg ccgccgcagt tcgaggcgcg caacgacttc
 9721 gatattttcc gcgagctgtg ccgtcgcttt aatcgcgaag aagcctttac cgaagggctg
 9781 gacgaaatgg gctggctgaa acgcatctgg caggaaggtg tacagcaagg caaaggacgc
 9841 ggcgttcatc tgccagcgtt tgatgacttc tggaataaca agagtacgt cgagtttgac
 9901 catccgcaga tgtttgttcg ccaccaggca ttccgcgaag atccggatct cgaaccgctg
 9961 ggcacgccga gtggcctgat tgagatctac tcgaaaacta tgccgatat gaactacgac
10021 gattgtcagg ggcatccgat gtggtttgag aaaatcgaac gctcccacgg tgggcctggc
10081 tcgcaaaagt atccgttgca tctgcaatct gtgcatccgg atttccgact tcactcgcag
10141 ttatgtgagt cggaaacgct gcgtcagcaa tatacggtag cgggtaaaga gccagtattc
10201 attaacccgc aggatgccag cgcgcgcggt attcgtaacg gtgatgtggt acgcgtcttt
10261 aacgctcgcg tcaggtgtt ggcaggggca gtggtttctg accgctatgc acccggcgtg
10321 gcacgaattc acgaaggggc atggtacgat ccagataaag cggcgagcc tggtgcgctg
10381 tgcaaatacg gtaaccccaa cgtgttgacc atcgacatcg gtacatcgca gctggcgcag
10441 gcgaccagtg cgcacactac gctggtggaa attgagaagt acaacggaac agtggagcag
10501 gtgacggcgt taacggccc cgtggagatg gtggcgcagt gcgaatatgt tcccgcgtcg
10561 caggtgaaat catgaccacg ctgacagcac aacagattgc ctgtgtttac gcctggctag
10621 cgcagttgtt ctcccgtgag ctggacatgg aacaactgac gcaaatcgcc agtgcgcaga
10681 tggctgaatg gttttcgttg ctgaaaagcg aaccgccgct cactgcggcg gtgaacgagc
10741 tggaaaaccg tattgccacg ctgacagtac gtgacgatgc ccgtctggaa ctggccgcgg
```

```
10801 acttttgcgg cctgtttctg atgaccgaca aacaagcggc gctgccgtat gcatcggcct
10861 acaaacagga cgagcaagag attaaacgct tgttagttga ggcagggatg gaaaccagcg
10921 gcaatttcaa cgaaccggca gatcatctgg cgatctatct cgaattgctc agccatctgc
10981 attttcgct gggagagggg accgttcctg cgcgaagaat cgacagtttg cggcaaaaaa
11041 cactgacggc gctgtggcaa tggttaccag agtttgttgc gcgttgtcgt cagtatgaca
11101 gctttggttt ttacgcggca ctaagccagt tattgctggt gttagtggag tgcgaccacc
11161 aaaacagata acgtcgtttg tgcgcctgaa aagacgcgtt tagcgtcgca tcaggcatta
11221 tggcgcagtt gccggatgcg gcgtgaacgt cttatccggc ccacaggaac tgtaa
```

AE 000202 (Section 2)

```
   1 ttatggcgca gttgccggat gcggcgtgaa cgtcttatcc ggcccacagg aactgtaatc
  61 tttgtagacc ggttaagatg cgtcatcgca tccggcaaac acacatcacg gatgagctac
 121 aaaccgggaa agccgctggc gcagcaggcg gtttcctgc ttcaggtgcg caatatcatc
 181 cattaacgtc agcgccaccg cgatccccgg ccagtccaga gccagttcat gacgcaggcg
 241 taccgcgcgt tgcaccacaa tggcggcatg gtcgtcaaat acccaggttg tttcctggat
 301 ctcacgcggt tcaaccaccc ccaaaccgac aatttcattc aactcctctt cagagatgcc
 361 ggtatgcagg caaaattcgg taatagtaaa agtcaccgta acattagcca ttatgctttc
 421 ccccaatctt tacgtggatc aaaagacgac tgggcgtctg ccagttgctg ccacagcgcg
 481 gcagtgtttt catccggttt cggcggcatc acgattttca gtaccgcata cagatcgccg
 541 gtctgttttt tgctcaccag acctttgcct ttaacgcgca atcgttgccc ggcctggctg
 601 cctggcggga tagtcagcaa aatgctttct ttcagtgttg aacggtgac tttagcaccc
 661 agcgccgctt cccacgggct aaccggcacc acaatttcca gatcctggcc gacaatatca
 721 aacagcggat gtggcgcaat atgaatcacc agccacaaat cgccatttgg accgccgttt
 781 tcgcccggcg tccctggcc tttcagacgg atgcgttgac cattgccgac gccgccggg
 841 atcttcacat tcagcgtttt cggaatttcc tgttcgatca tgccaaaggc gttataaacc
 901 ggcaggttat agctgatggt acgcttatgc tcagtaagcg tttcttcgag gaataccgcc
 961 acttcgattt caatatcgtg gccgcgtgtg gcggggcgtt gacggctctg gcgggcatgc
1021 tgaccgaaaa ttgacgagaa gatatcgtca aaatcttcgg cgttaaaact ctgaccgtcg
1081 ccatggtgga actgacggtt aaattgcgga tcgttgcgat gttgccacat ctgatcatac
1141 tcagcgcgac gttgttcatc acttaacact tcccaggctt cagcgacctc tttgaagcgg
1201 gcttcggcat ccggttcttt gctgacatca ggatggtatt tgcgggcaag tcgacgatag
1261 gcggtcttga ttgtcttgag atcgtccgtc ggtttcacgc ccatgatggc gtaataatcc
1321 tttaattcca tagcgttatc tcgcgtaaat caacacaaat tgaaggaacc cctgtaaggt
1381 aactcctata agtgtagggt aatcctcaaa atttcatatg ccaacacaga atatgttatt
1441 gaaatcatcg cggagaggag gtcgccatca agatgggttg ctgaacatat tttaaacagg
1501 tgaaaaaggg tgagcgattt ttgatagttg aaccaggcac tttaagttta actagggcgt
1561 cattatttat taaatttat agacgctata tatgggtagt aatatacatg gaattagttg
1621 cactgcaaat aattatttga acaggcctg gaacgatata aaaatgagt acgaaaaaaa
1681 tcaaacatat tcaatcacgc ttttttgaaaa cacactggtg tgttttatgc ggttatacaa
1741 tgaactcaga cgtaaagtaa atgaagagga tactccatgt ctggaatgtg aatcactaga
1801 aaaagaattt gaggaaatgc agaatgataa tgatctatca ttatttatga gaatattgcg
1861 tactaatgat acacaaattt attcagggt ttcaggaggt attacatata ctatacaata
1921 tgttcgagat attgatattg ttagagtgtc cttgccgggc agagcttcag agtctatcac
1981 agattttaaa ggttattatt ggtataactt tatggagtat attgaaaaca ttaatgcgtg
2041 tgatgatgtt ttttctgagt attgttttga tgatgaaaat ataagtgtcc agccagagcg
2101 gataaatacg ccgggaatat ctgatttgga ttctgacatt gatttgtctg gtatatcttt
2161 tattcagcgt gaaactaacc aggcattagg attaaaatat gctcctgtag atggcgatgg
2221 atattgtctg ttaagagcta tactggttttt aaaacaacat gattattcat gggcgctggt
2281 cagttataag atgcaaaagg aagtttacaa cgaattcatt aaaatggttg ataaaaaaac
2341 gatcgaggct cttgttgata cggcattcta taatctcagg gaagatgtaa agacgttatt
2401 tggcgttgat ctacaatctg acaaccaaat tcagggcag agtagtctta tgtcatggag
2461 ctttctgttt tttaaaaaac aattcattga tagttgcttg aataacgaaa atgtatcct
2521 gcatttaccc gagtttatat ttaatgataa caagaacttg cttgctttag ataccgacac
2581 gtcggatagg attaaagcgg tgaagaattt tcttgttgtt cttttcagata gcatttgctc
2641 attatttatt gttaatagta atgtggcatc aatccccttg gggaatgaat ccttttcaac
2701 agatgaagat cttgagtatg gttatttaat gaacactggc aatcattatg acgtttacct
2761 ccctcctgaa cttttttgctc aggcttacaa gttaaacaat aaggaaatga atgcgcaact
2821 cgactattta aatcgttatg caatttaatg gcaaaggcat atgctaaaaa ccattgttat
2881 tagtctcaca ctttttttatt ggtaaatatt gtctctgtat tggtaacgcc gcagatattc
2941 tgtttagcca caggtgcaat tatcagcggc gtacgcgagg caggggctaa tcaggcatag
3001 tttgcgtcaa accttgcctg tttttgaaga tgtatataga aaacaggcg ttcaacaagc
3061 catttttgcga acctgttccc ggaaaaaagt catattctg tcacactctt tagtgattga
3121 taacaaaaga ggtgccagga atgaacaaaa cgctaatcgc cgcagctgtg gcagggatag
3181 ttttactcgc ttcaaacgct caggcacaaa ccgtaccgga aggctatcag ctacagcaag
3241 tgctcatgat gagccgccat aacttacgtg cgccgctggc gaacaatggc agtgtgctgg
3301 agcagtcgac gccgaataaa tggccagaat gggacgtccc cggtgggcaa ctcaccacca
3361 aaggtggcgt gctcgaagtg tatatgggcc attacatgcg tgaatggctg cagagcagg
3421 ggatggtgaa atcggggaa tgcccgccgc cgtacaccgt ttatgcctat gccaatagtc
3481 tgcaacgtac cgttgcgacc gcacagttct ttattaccgg cgcattcccg gggtgtgata
```

```
3541 ttcctgtgca tcaccaggaa aaaatgggca ctatggaccc aacctttaac ccggtgatca
3601 ccgatgattc cgccgcattc agtgaacagg cggtggcggc aatggagaaa gagctcagca
3661 aactccagct taccgacagc taccagctac tggaaaaaat cgttaactat aaagattccc
3721 ctgcctgtaa agagaaacaa cagtgttcgc tggtggatgg caaaaatacc tttagcgcca
3781 agtatcaaca agaaccaggt gtttccgggc cgctgaaagt cggcaactcg ctggtagatg
3841 cgtttacttt gcaatattac gaaggttttc cgatggatca ggtggcctgg ggagaaatca
3901 aatctgacca gcagtggaag gtgttgtcga agcttaaaaa cggctaccag gacagcctgt
3961 ttacctcacc ggaagtggcg cgcaatgttg cgaaaccgct ggtcagttat atcgacaaag
4021 ctctggtcac cgatcgcacc agcgcaccga aaattacagt gttggttggg cacgactcca
4081 acattgcctc tctgttaacg gcgctggatt tcaaaccgta tcagttgcat gaccagaacg
4141 aacgcacgcc gattggcggc aaaatcgttt tccagcgttg gcatgacagc aaagccaatc
4201 gcgatttgat gaaaattgaa tatgtgtatc agagtgcgga acagttacgt aatgccgatg
4261 cgttaaccct gcaggcacct gcgcagcgtg tgacgctgga attaagcggt tgcccgatag
4321 acgctgatgg tttctgcccg atggataagt ttgatagcgt gttgaatgaa gcggtgaaat
4381 aacagaaaac tcccccgcga gaagcggggg agtcgctggt taaacgtttt tacgttcgat
4441 ggtctgttcg ccccaaaaaa gcgaatcttt atcggtctta gcaaaggctt tgactaacac
4501 ttcatcacta ccttcttccc aaatcttttc cgccatttttt tcgtcgtacc cggcgacttc
4561 gaaaatggcc tcggctattt ccggcgacgt attgcgcaga gatgcccatt caccgacgtg
4621 atgagctttc gcttcttgag ttggcatgcg tatcctcctg ttgaagatta gccgttaagt
4681 ttaactgcca gacctgcgac atattcccct tgataacgag caatagacag ttcttcctgg
4741 ctgggctggc gtgaaccgtc accgcctgcg atggtggttg cgccgtacgg cgtaccgccg
4801 cgaacctgtg aaacgtcaaa taattcctgc gctgcgtagc caatagggac aattaccatg
4861 ccgtgatgcg caagggtcgt ccaggtggat gtgatggttt gttcctgacc gccgccagta
4921 ccggtggaac taaagacgct cgccagtttt ccgtatagtg cgccggaagc ccacaggccg
4981 cccgtctggt cgaggaaggt acgcatttga ccggacatgt tgccaaagcg ggtaggtgta
5041 ccaaaaataa tggcgtcgta atcggccagt tcttgcgggg ttgcaaccgg tgcagtttgc
5101 gtttttaccgc ctgcttttc aaataattgc ggcggcatgg tttccggtac acgcttaacg
5161 acaacttcag cgccatccac tttgcttgca ccctcagcga ctgcgcgtgc catcgtttca
5221 atatgtccgt acatggaata ataaagcacc agaactttag ccatttctaa ccactcctcg
5281 tgttatctct attccgtagc gattcgctac cacttattta aagataagac gtcctttca
5341 gagtgcaaat ttcacaacca cttatttgat ttataacaac tttcacaagc acgtaatttt
5401 gtcgcaaaat gacacatttt tatctcatcg cgttttttta atcataagag cggcttatgg
5461 ataattattg gagatgatat ctattctcgc taagaagctg ttgcaggata ttaccaaacg
5521 cgggtctgtc cgcgtcagtt cactaagctt agtcccacgt agcgaaaata tggcagccgc
5581 catacgccgc gttaattcta tgcaatatga tgtctatacc cagacggagg tcagtaatgg
5641 caaaccatcg aggcggttcc ggcaattttg cagaagaccg cgaaagacga tcagaagcag
5701 gtaaaaaagg tggacagcac agcggggggta atttcaagaa tgacccgcag cgcgcatctg
5761 aagcaggtaa aaaaggtggt aagagcagtc acggcaaaag cgacaactag ccgggctaat
5821 caatgacgaa tgcatttttg tctgtagctc gtcaaaaagc catcaccgcc ggttacccgg
5881 tggttgatac tgatgacaaa tgtaagcttg cctgatgcgc gatgcttatc aggcctacca
5941 gaagattgca atatattgaa tttgcactgt tttgtaggcc ggataaggcg tttacgccgc
6001 atccggcatg aacaatgcgt acgttgtcaa caatctgcac cgccggtaac cccggcggtt
6061 ttctgtttat ggctcctgat gaacaacttc tgcggtgga acgtcaacca actttctgct
6121 taacaacgca ttgagtaaaa tcgcgccaaa ggttgctgta ccaatccctc caacgtaaa
6181 accgccagc gtgagagcaa aatcacccgc gcccagcact aaggttactg cgaccataat
6241 caaattaccg ttctggctta aatcgacacg gttttgtacc catatccttg cgcctgcgac
6301 ggcaatcagc ccgaacacaa caattgatgc accaccaata accgcggccg gaatggtatg
6361 aatcagcgca ccaaatttcg gtgaaaagcc caacagcatg gcgatgacgg cagcagcaac
6421 aaacaccagc gtcgagtaga ctttggtcac ggccatcaca ccgatatttt cagcataggt
6481 ggtcacgccg ctaccgccga cagagccgga aagcatcgtt gccagaccat cgcctacgaa
6541 tgcccgcccc atatacgggt ccatattgcg tccggtcatc ccggcgactg ccttgagatg
6601 acctaagttt tccgccacca gaatcaccgc cacgggcgca atcagcatca ttgcctgacc
6661 attaaaagca ggagtggaaa aatgtggcag accgaaccag gcagcatggc tgacgagagt
6721 aaaatcgacg gcttttccca gccctaaaac gttggtcatc acgccataca gcagacaggc
6781 gacaattaat cctacgagaa tcaataaccg ctggatcatg ccacgggtaa acaccgccac
6841 cagcccaata cacagcaccg tcattaccgc catccagcta tcaaggccg aagccgatac
6901 acttttcact gcgataggcg ctaagttcag gccaatcgcc atcaccaccg cacccgtcac
6961 caccggcggc atcagtcgtt caatccagcg cgtaccgatt ttcatcacca ccaggccaat
7021 gacggtataa accagcccac aggcgataat cccgcccagc gcaatgctga tattcgggtt
7081 aatgccctga ccgttaaagc ccgtcgcggc gatcaccacg ccgacaaaag ccgcgctaga
7141 gccgagataa ctggggacgc gcccgccggt aataaagaaa aacagtaacg tgccgatccc
```

```
7201 cgacattaaa atggaaagat tgggatccag ccccatcaga atcggcatta acaccgtcgc
7261 gccaaacatc gccaccgcgt gttgaacgcc cattactgcc gtctgagcaa acggcaatcg
7321 ttcatccggc gcgaccacgc cgctctctgt agaggtcgat tttaactgcc agtgaggaaa
7381 accgaacatt gccatcagct gtctccttaa ggaggttaac aagcagggcg catcagcgcg
7441 tgataactgc gatcgaacca caccagcccg tagggtgtgg tgtgacgatg aatcgcttcg
7501 atggcgcaaa acagaatgtc gtgggtgccg acgctcacca cctggctgat acggcagtca
7561 aacgaaacca gagcctcttc cagttgcggg catccggtca cccccgtctg ccagcgggcg
7621 gcggcaaagc ggtgttccat gggcgttttg ccgccaaaaa ggtttgaaag cggctcctgc
7681 ccggcgctaa gtgtatttac acacagcgtt cgattttcat tgaatgccgg ccagacggac
7741 gccccacgat tcaggcacac cagtaatgtg ggcggcgtat cggtcacact gcagacggcg
7801 ctggcggtga accggcgcg cccggctgga ccgtccgtgg tgataatatt gaccgccgcg
7861 cccatgcagg acatcgcatc gcgaaaagtt tgttgatcga caatgttcat agtttgctcc
7921 ttacaacagc ccgcaggctt cttcaaagga cagacgtggc aggcgcgcat aaagcttgct
7981 gctatcgcca tagccgtatat taatcagcag attgctcttc agcgtgctgc ccgtaaaaaa
8041 ggcgtcgtcc acgtgttgac ggtcaaagcc cgacatcggg ccggtatcca gtcccagcgc
8101 ccggcaggcg acgatcagat aggccgcctg catggaactg ttgcgaaacg ctgtttcttc
8161 ggcaagttgt gggctggagg taaaccaact gcgggcatca ccgtggggaa acagtagtgg
8221 taaccgttca taaaattcac tgtcccaggc gacgatagcg gtgacgggcg cggtcagggt
8281 tttttgcaga ttgccgctgg aaagtgccgg gcgcagacgt tcttttcctt ctgccgtgcg
8341 ggtaaacacg atccgtgccg gagaacagtt agctgatgtc ggcccccatt tcatcagggc
8401 ataaatctcc cgtaacgtct catcgctgac gggtgtctcc cgccagccgt tgtgagtgcg
8461 ggcatcggtg aacagggtgc taagcgcacc tgggctaacg gcttcgttca tagcaattcc
8521 ttacagggcg gcttcacggt gatgtaacag gctggcaagc ccgttgagta acagagcatt
8581 aaacgtttcg ggatcggtca cgttgcaggc gtgtccgcca tagggcatca ccattttctg
8641 gctatcgggc agggcggcat gaagttcact ggaacatgct gttggcacca gcagatcatc
8701 actggcgcag atgatttgca ccgggcagcg gatgcgatcc gcatggtgac taaagtcagc
8761 gcgtttgagg gcgttaagtc gacgcagtaa attattttg ccctgaaaat gcgccagtgc
8821 cagcgcgtct tctgcctcca ggcgaggtgc gcgggccgcc atccagtcgg cgggatagag
8881 gaacaacggc tgcgcttcca cccatgcctg cgcgccgcc ctatacagta atcgttcgcg
8941 aacctgaaaa cagcggcgcg tatggcgtt tattcgtagc cagccgttaa cgctgatcag
9001 cacagttacc gacgcgggat aatccagcgc cagctgcatt cccaccagcg caccgagcgc
9061 atggccgacc actgcgtaat gctcaatccc tgcggctacc agcgcctgat gcagttccgc
9121 tgccatctgg gcgatactgt aatcttctgc cagcgtgtcg ggattattgc cggtgccgcg
9181 ctggtcgtaa cagactacct gatactcctg ctccagcacc gccagttgcg gtaaccagta
9241 actgccgcta cccccaagac ccgaaatcaa caccactacg ggcgcatcag cataaggggg
9301 aggtgagagt gaaagtttca tcgcggcctc acttggcgat atgcgcaatt gtggcgattt
9361 ccaccagcgc gtcaggtttt accagtccgc actgaatgca gaatcgcgcc ggtttatcac
9421 ccggaaaaaa ctcggcgtag atttcgttaa tcgcggcgta attttttccag tcggtaataa
9481 agatgctgtt gaaggtcaca tccgccatcg tgccaccgc cgtctcgatc accttgcgga
9541 tagtttccag aacgtggcgg gtttgcgcct ttgggtcatc ggcaaacagc acgttattat
9601 gttgatcaaa agccagcgta ccggagacat acaccacgcc atcagccagc gtgccgggaa
9661 cgaaggggc cagcggtgcg ctgctgccag cggaataat tacggatttt ggcatcgtta
9721 aactccttaa gcgatatgag caaaggacgt gggagaaagc gcgtcgcaga atgtttcgac
9781 gtcgctgacc cagccaaaaa aggtttcgat attgaacaac gcggctttct gcgcaaattt
9841 cggccccgcc tggtgagttg cgtcttcaag caccacgccg aaatactcca gaaaaaagcc
9901 gtcgcgtagc gtcgattcga cgcagacgtt ggtagcgatg ccggtgaaaa ccagatggcg
9961 tattccgcgg ctgcgcaaaa tgctgtccag cggcgtattg aagaaaccgc tgtagcgcgg
10021 cttcggcagc acaatatcgc caggctgcgg caccagttca tccaccagtt gataatccca
10081 ggagcctttc gccagcaatt tcccctgcag ctgcggctgc ttacgcatgg ttttcagggc
10141 gttcgattta tgaaattcg gtgagccggg tccgccagcc tcgacatact gttcatccca
10201 gccattttga aaccagatga tcagcatccc tgccgctcgc gctgcggtca cggcggtttg
10261 aatgttggca atgaccgggc gagtggttga gacatcaaac ccggcgagat ctaagtagcc
10321 gcctggcgtg gcataagcgt tttgcatatc caccacgatc agcgcacttt gctgcggatc
10381 gaaggtaatg gcttccggtc gagcggttaa ggtcgtcatc atgccacctc ctgagtcagc
10441 gcaggtagat gggcgcggca ttcatcagt ggttgaatgc gctcgccgaa ggtttcgatt
10501 cccgacagaa aatcgtcgaa ggttaacagc acgccttcgg caccaggcac gcttgcgact
10561 tcatctaaca tgcgcgcgac actggcgtaa gaaccgacta acgtccccat attgatgttt
10621 accgccgaag tgggatcggc catctgacga acgttggtgt cagtaccgga gcgggtatct
10681 ttctgacttt gttcggttag ccagtcttaa gcctcttcat ccgcgcccgc tttgtagtgt
10741 tcccatttgg cgcgagcggc atcgtcggtt tcatcggcaa tcaccataaa caacacataa
10801 gagccaacgt cgcgtccggt ttgctctgcg gcctgtttca tccgcgcagc ggtcgggggcg
```

```
10861 aaagccgtgg gtgtatttac gcctttgccg aaacagaagt tgaaatcggc ataccgggcg
10921 gagaacgcca tgccagcgtc gctttgcccg gcgcagatca ctttcatggg gacactcggt
10981 tgcggactca cgcgacaatc attcatggtg aaaaaatcgc ctttaaaatc gctttccccc
11041 gtgccccaca ggtcgcgcag cacctgaaca tattcggtga gatagtcgta acgacgggag
11101 aaatagtcat cgccaggcca gatacccatc tgctcatact cgggcttttg ccagccagtc
11161 acgaggttga cgccaaaacg cccgccagag atggagtcga tggttgcggc catacgggcg
11221 acgattgccg gaggtaacgt taaggtggca gcagtggcgt aaatctgaat gcgcgaggtc
11281 acggccgcca gccccgccat caaggtgaac gactcaaggt tgtgatccca gaactcagtt
11341 ttgccgccaa agccacgcag tttgatcatc gacagggcga atcgaaatg gtagtgctcc
11401 gcttttttgca caatggcttt attcagttca aaggtcggca tgtactgcgg cgcgtgggtc
11461 gaaatgagcc agccgttgtt gccaataggt acgaatacgc caattttcat catcaacctc
11521 tcttcgtctc gtaaagtgaa agtcagacgg ggcgctgcat cctgcatatc cttttcagcc
11581 gcgtattggc ttgtttgcaa agcggatgcc agttttaaa aagttaatgt tattaatctg
11641 ttaacattac gttatctaaa atatctggta aaaagtggac taaacggtca aaacagttgc
11701 acataaaaca
```

AE 000203 (Section 3)

```
   1 tatctaaaat atctggtaaa aagtggacta aacggtcaaa acagttgcac ataaaacatg
  61 catctgtgcg cgatgagagt gcagaaggtc gaggccgggc gggggttttg ctatcctgtt
 121 gccaatctac aagaggggag agcgcatgac gcaaggcgca gtgaaaacaa cgggtaaacg
 181 ttcgcgcgca gtaagcgcga agaaaaagc gattcttagc gcagcactgg acactttttc
 241 acaattcggt tttcacggca caaggctgga gcagatcgca gagttggcgg gtgtttcaaa
 301 aaccaatctg ctgtattact ttccgtcaaa agaggcgctg tatattgccg tgctgcggca
 361 gattctcgat atctggctgg caccgttaaa agcgtttcgt gaagatttcg ccccgctggc
 421 ggcgatcaaa gagtacatcc gtctgaagct ggaagtctca cgcgattatc cgcaggcttc
 481 gcgcctgttc tgtatggaga tgctggcagg cgcgccgctg ttaatggatg aactgacggg
 541 cgatttgaag gcattaattg atgagaaatc ggcgctgatt gccggttggg tcaaaagcgg
 601 caaactcgcg ccgattgatc cgcagcattt gatttttatg atttgggctt ccactcaaca
 661 ttacgccgat tcgcccctc aggtggaggc ggtgacaggc gcgacgttgc gcgatgaggt
 721 atttttcaat caaacggttg aaaacgtgca gcggattatt attgagggga ttcgaccacg
 781 ttaaagatgc cggaggaggt tgtaacatcc tccggctacc tgtttaacct atagtcatta
 841 agctggcgtt accgccagcg gcagcggtat tcacactcag cgaacgctcg atatacagcc
 901 gttccagaag gatattgctt tcgccacggg caaaaccctg caccgaaaca attgtgccat
 961 cccgcgcggc aactgcttca cacaatgcgc gaagctgatc cgaatcaccg tggaagatca
1021 ccgcatcaaa cggttgagcg gttatatttt ccgctttcgc cagttgaata cgttcgctga
1081 ctgccgatgg caatgccttc actaactgac gatgcagcgc gtcatccggc cacagtacct
1141 ggctgcccac cgccagcacg gcggcgagct gagtcagcgc atcctgctca tcatcggcaa
1201 tacacaacac gcgctcacgc ggcagcagcg tccaggtgtt gcgttcaccc gtcggccccg
1261 gcagcaatcg ttgtgttcct gcctgcgcca gctcgccata ttgcgtacat aacgcctgca
1321 attctggacg atttgctgcc cattcccgca gtgcatttag cggctgagtc aatgcggctt
1381 tcaactgcgc atcgaccgga tactttgcat cctgacgcgc gagcgtcact gccagcgcac
1441 tttccgggcg attcgccagc agacggtaga gatagagcgg accgcctgct tcggccgg
1501 taccggacaa cccttcgccg ccgaacggct gcacaccaac cactgcgccc accatattac
1561 ggttaacata caggttacca acatgggccg agccagtgac ctgggcgatg gtttcatcaa
1621 tgcgcgtatg gacgccaagc gtcagaccat aaccggaagc gttaatctgc tcgatcagct
1681 ctggtagctg gttacggttg taacgcacca catgcagcac cggaccaaag acctctttt
1741 gcaattcggc aaagtcatcc agttcgatca gcgtcgggc gacaaggtg ccgctttgcc
1801 attcacgggc atcttcgctg ttttcccgca ccgcctggaa caccggacgg cctttgctac
1861 gcatggtctg aatatggcgc tcaatattgg ctttcgcttc gctatcaatc actggaccga
1921 tatcggtggt caggcgaccc ggattaccca tccggcattc ggccattgcg ccgcgcagca
1981 ttttcaacgt gtggtcggca atctcatctt gcaggcacag cacgcgcagc gccgaacaac
2041 gctgacccgc actgtcgaac gccgaggcca gtacatccac gacgacctgt tcggtcagtg
2101 ctgaagaatc gacaatcatc gcgttcatgc cgccggtttc agcgatgagc ggaatagggc
2161 gaccctgagc gtccaggcgg ctggcgatat tgcgctgcag taacgtagcg acttcggttg
2221 aaccggtaaa catcacccg cgcacgcgat catcacccgt cagttgcgcg cccacggttt
2281 caccccgacc tggcagcaat tgcaccacgc ctggcggtac acccgcttcc agcaaaatgg
2341 cgatcccttg cgcggcaatc agcggcgttt gttctgccgg ttttgccagc acgctgttac
2401 ctgccgccag tgcggcggcg atctgcccgg tgaaaatagc cagcgggaag ttccacggac
2461 tgatacacac cacaggccct aatggacggt gggtttcgtt agcgaaatca tccgcacct
2521 gtccggcgta gtagtggaga aaatcgaccg cttcgcgcac ttcggcaatg gcgttactga
2581 aggttttccc ggcctcacgc accagaatac caatcagttg ctgcatctgg cttttccatca
2641 gcacggcagc gcggtgcaaa atcgctgcgc gttcagccgg aggcgtggca aaccagattg
2701 gcgcgttatt aaccgcactt tccagcgcct gttctacttc acgcggcgtg gcttcacgca
2761 catagcccac aatatctttc ggttccgcag ggttaataac gggcgacatc tcacctgccg
2821 ctaccggttg ttccagcatt ggcaaggcct gccattttg cagtgcacta ttgagcaggg
2881 cagaggagag cgaggccagg cggtgttcgt tagcgagatc cagccctgcc gagttgtcgc
2941 gcccgtgacc gtaaagatcg cgcggcaggg gaattttcgg atgcggtaat ccagtttgcc
3001 cttcctgttg cgccagtttt tctacagcag tgaccggatc ggcgaccagt tcatccagtg
3061 gcaaagaggt gtcggcaata cggttaacaa acgaggtgtt agcaccgttt tccagcaggc
3121 gacgcaccag atacgccaac agcgtttcat gtgtgccaac cggagcataa atacgacacg
3181 gacggttaag tttgccgtcg gcaactttcc cggtgacctg ctcatacagt ggctcgccca
3241 taccatgcag gcactggaac tcgtactgac ccgggtagta gttctgcccc gccagttgat
3301 aaatcgccgc cagcgtatgg gcgttgtgcg tcgcgaactg cgggtagatt agattcggca
3361 ccgccagcag cttttcgca cagccgagat aagaaacgtc ggtatacacc ttgcgggtat
3421 aaaccggata accttcaagg ccgtccatct gcgcacgctt aatttcacta tcccagtacg
```

```
3481 cgcctttcac caggcgaatc atcagacggc gacggctgcg ggtggcgaga tcaatcaggt
3541 aatcgatcac caacgggcag cgttttttgat aagcctgaat aacaaaaccg atgccgttcc
3601 agcctgccag ttccggctcg aaacagagtt tttccagcag atcgagggag atctccaggc
3661 gatcggactc ttcggcgtca atgttgatac caatatcgta ctgacgcgcc agcagggtga
3721 gtgatttcag acgcgggtaa agctcttcca ttacccggtc atactgggcg cggctataac
3781 gcggatgcag cgccgacagt tgattgaaa tgcccggccc ttcatagatg ccacgaccgt
3841 tagacgcttt accgatggcg tgaatcgcct gctgatagga aaccatatac gcctgtgcat
3901 ctgcggcggt cagcgcggct tcgcccagca tatcgtaaga gtaacggaaa cctttctctt
3961 ccagcttgcg ggcattggct aacgcttccg cgatggtttc gccagtgacg aactgctcac
4021 ccatcaggcg catcgccata tccacacctt tgcggatcag cggttcaccg cttttaccga
4081 taatgcggtt cagcgagcgg gagaggctgg cttcgttatg ggtggaaacc agtttgccag
4141 taaacagcag cccccaggtg gcggcattaa caaacagtga cgggctacga ccaatgtgtg
4201 actgccagtt accgttgctg attttgtcgc gaattaacgc gtcgcgggtg gctttgtcgg
4261 gaatacgcaa caacgcttcc gccagacaca tcagcgccac gccttcctgc gatgacagcg
4321 aaaactcctg caataacccc tggaccatac ctgcgcgacc actggcattt ttttgattac
4381 gcagtttatc ggccagctga tacgccagtt tgtgcgcctg ttcagcaact ggctgcggca
4441 ggcgggcttg ttccagcagc atagaaaccg cttcggtttc cgggcggcga taggccgcgg
4501 tgatcgcggc gcgggaaacc gactggggca atatttgctc ggcaaagtcg aggaatggct
4561 ggtgtggttc ctctgccgga gtcggtgctt catcgctctc attggccgcg ccagaaagca
4621 gcgcaggtag ctccggcaga gtatcgctgt tttccagttg ttcgagataa gaaaaaatcg
4681 cctgcttaat taaccagtgt ggtgtgcgat cgatacgtgt cgcggcagac ttaatacgct
4741 cacgcgtcgc gtcgtccagc ttaaccccca tggtggtggt tccatgcca ttactcctgt
4801 tgttcagaaa ggtgcaactt aacgttatcg tgaaatatcc atgatgttgc aactttgtgc
4861 aaccatgtta aatgtgacat gcgtagcaag cttaaaaatg aatgaaatgt taataaaaga
4921 aatcgatatg acagggatta aaaaaataac tcagactttt tctctgcggc agttaacatt
4981 tttgaaaggt gcaaccgcaa aaaatgtgag agagtgcaac ctgatgaaaa atagtgtcgc
5041 tgagcactaa aatttaatgt aaatggtgtg ttaaatcgat tgtgaataac cagcgcttcc
5101 ggcaggatac ggtcgccctg gtaaaacata aactctgtta ccccgttccg gtggcagata
5161 taacggcaag tttcgacatt gccgataata attttttgga gactttagat ggctattagc
5221 acaccgatgt tggtgacatt ttgtgtctat atctttggca tgatattgat tgggtttatc
5281 gcctggcgat caacgaaaaa ctttgacgac tatattctgg gcggtcgtag tcttgggcca
5341 ttcgtgacgg cattatcggc gggtgcgtcg gatatgagcg gctggctgtt aatggggttg
5401 ccgggcgctg ttttttctttc cgggatttcc gaaagctgga tgccattgg cctgacatta
5461 ggcgcgtgga ttaactggaa gctggtggcc gggcggttgc gtgtgcatac cgaatacaac
5521 aataacgcct taacactgcc ggattatttc accgggcgct tgaagataa agccgcatt
5581 ttgcgcatta tctctgcgct ggttattttg ctgttcttca ccatttattg cgcttcgggc
5641 attgtgcag gcgcgcgtct gtttgaaagt acctttgcg tgagctacga acggctctg
5701 tgggcgggcg ctgcggcgac gatcctttac acctttattg gcggtttcct cgcggtgagc
5761 tggactgaca ctgtacaggc cagcctgatg attttttgcc tgatcctgac gccggttatc
5821 gtcattatca gtgtcggtgg ctttggtgac tcgctggaag tgatcaaaca aaagagcatc
5881 gaaaacgttg atatgctcaa aggtctgaac tttgttgcca ttatctcact gatgggttgg
5941 gggctgggtt acttcggcca gccgcacatt ctggcgcgtt ttatggcggc ggattctcac
6001 cacagcattg tccatgcgcg tcgtattagt atgacctgga tgatcctctg cctggcaggg
6061 gcggtggctg tcggcttctt tgggattgct tactttaacg atcatccggc gttggctggt
6121 gcggtaaatc agaacgccga gcgtgtgttt atcgaactgg cgcaaattct gtttaacccg
6181 tggattgccg ggattctgct gtcggcaatt ctggcggcgg taatgtcaac cttaagttgc
6241 cagctgctgg tgtgctccag tgcgattacc gaagatttgt acaaagcgtt tctgcgtaaa
6301 catgccagcc agaaagagct ggtgtgggta gggcgtgtga tggtgctggt ggtggcgctg
6361 gtggcgattg cgctggcggc aaacccggaa aaccgcgtgc tgggcttagt gagctacgcg
6421 tgggcaggct ttggcgcggc gtttggtcca gtggtgctgt tctcggtgat gtggtcacgc
6481 atgacgcgta acggtgcgct ggcgggatg atcatcggtg cgctgacggt tatcgtctgg
6541 aaacagttcg gctggctggg actgtacgaa attattccgg gctttatctt cggcagtatt
6601 gggattgtag tgtttagttt gctgggtaaa gcgccgtcag cggcgatgca aaaacgcttt
6661 gccgaggccg atgcgcacta tcattcggct ccgccgtcac ggttgcagga aagctaaggg
6721 acttagcctg cggcggtttt gtttggcttc agcagcgggt tgcgctccct taatgtgcct
6781 cgccatataa attgaatggt gcagggagcg cgcaggggc ggccaatcgc gccgccccc
6841 tgctgtcccg gccttcgggg aacgcttcag cgattttgac gccaccaaca cccgagctgt
6901 tattatgttc cgggcaaaaa gttagatttg ataatcgcgg atggacgaaa ttgcttgata
6961 cacccgctta tcagttttac atggaagctc tgatgcattg agtctggaca gttttgtcgg
7021 ctggatacgg cgtttacgcg gcatccggca agaacacatg gttctttgca aacaatccca
7081 tctttctacc ctggaataat cgtttatatc cccttggcatt acctctcttt gtttacattc
```

```
7141  caacatcatt ttataaacat tccgcttgtg tttttctttg ccgtaatgat aatcgctatc
7201  actgcgattt acttttcttt gcatagattg actcagaaaa acgtttaagg gtgggtggca
7261  tgtttgttcc gtttctcatt atgttgcgcg aaggacttga agccgcgctg attgtcagtt
7321  tgattgccag ctatcttaag cgtacccagc gaggccgatg gattgtgtga tgtggattgg
7381  cgtgttgctt gccgctgcgt tgtgcctggg cttgggtatc ttcattaacg aaaccaccgg
7441  cgaatttccg caaaaagaac aggaactgtt tgaaggtatc gtggcggtga tcgccgtggt
7501  gatccttacc tggatggttt tctggatgcg caaagtgtcg cgcaacgtca aagtgcaact
7561  ggaacaggca gtcgatagcg cattgcagcg tggaaatcat catggctggg cgctggtgat
7621  gatggtcttt tttgccgttg caagggaagg gctggagtcg gtcttttttcc tgctggcggc
7681  atttcaacaa gatgtcggga tctggccgcc gctgggtgca atgctcggtc ttgctactgc
7741  cgtggtgcta ggcttcctgc tctactgggg cggtattcgc ctcaatcttg gtgcatttt
7801  taaatggacc agcctgttta ttctcttcgt cgccgcaggg ctggcagctg gtgccattcg
7861  cgcatttcat gaagccggat tgtggaacca ctttcaggaa atcgccttcg atatgagtgc
7921  ggtgctctca actcactcgc tgtttggcac gctgatggaa gggattttg gctatcagga
7981  agcgccgagc gtcagcgaag tcgccgtctg gtttatttat ctcatcccgg cgctggtggc
8041  atttgctctg ccaccacgcg cagggcgac agcgtctcgc tccgcgtaac aaatacgacg
8101  caaactcttg cttagttaca acatacttta aagggatagt ctcgtcatga ccattaactt
8161  ccgccgtaac gcattgcagt tgagcgtggc tgcgctgttt tcttctgctt ttatggctaa
8221  cgccgctgat gtgccgcagg tcaaagtgac cgtgacggat aagcagtgcg aaccgatgac
8281  cattacggtt aacgccggga aaacacagtt cattattcag aaccacagcc agaaggcgct
8341  ggagtgggag atcctcaaag gcgtgatggt ggtggaagag cgggaaaata tcgcccctgg
8401  ctttagccag aaaatgacgg cgaatttaca gcctggcgaa tacgatatga cctgcggtct
8461  gctgactaac ccgaaaggga agttgatcgt caaggtgag gcaacggcgg atgcggcgca
8521  aagtgatgcg ctgttaagtc ttggtggtgc aattactgca tataaagcgt atgtcatggc
8581  ggaaaccacg cagctggtga ccgacaccaa agcctttacc gacgcgatta agcaggcga
8641  tatcgaaaaa gcgaaagcac tgtatgcacc gacgcgccag cactatgagc gtattgaacc
8701  gattgctgaa ctgttctccg atctggatgg cagcattgac gcccgtgaag atgattacga
8761  gcaaaagcc gccgacccaa aattcactgg tttccaccgt ctggaaaaag cattgtttgg
8821  cgacaacacc accaaaggga tggatcagta cgctgagcag ctttataccg atgtggtcga
8881  tttgcaaaaa cgcatcagtg aactggcttt cccaccttca aaagtggtcg gcggcgcagc
8941  cggactgatt gaggaagtgg cagccagcaa aattagcggt gaagaagatc gctacagcca
9001  caccgatctg tgggatttcc aggctaacgt tgaaggctcg cagaaaattg tcgatttgct
9061  gcgtccacaa ctgcaaaaag ccaacccgga actgctggca aaagtcgatg ccaactttaa
9121  aaaggtcgat accattctgg cgaaataccg tactaaagac ggttttgaaa cctacgacaa
9181  attgaccgat gccgaccgga atgcactgaa aggaccgatt actgcgctgg cggaagatct
9241  ggcgcaactt cgcggtgtgc tgggactgga ttaagcgtta tgcagtataa agatgaaaac
9301  ggcgtgaatg aaccgtcacg ccgacgttta ctgaaagtga taggtgcact ggcgctggcg
9361  ggaagttgtc cggtcgctca tgcacaaaaa acgcaaagtg cgccgggtac gctttcaccg
9421  gatgctcgca atgagaaaca gccgttttat ggtgagcatc aggcagggat cctgacgcca
9481  caacaggccg caatgatgct ggtggcgttt gatgtgcttg ccagcgataa agccgatctt
9541  gagcggttgt ttcgcttgtt gactcagcgt tttgcttttc tgactcaggg cggagcagca
9601  ccagaaacgc caaatccgcg cctgccacca ctcgattccg gcattcttgg cggctacatt
9661  gcgcccgata atctcaccat cacgttatcg gtgggtcact cattgtttga tgagcgcttt
9721  ggccttgcgc cacagatgcc aaaaaagctg cagaagatga cgcgtttccc caacgactcg
9781  ctggatgcgg cgttatgtca tggtgatgtg ttgctacaga tttgcgccaa cacccaggac
9841  acggttatcc atgcgctgcg cgatatcatc aaacacacgc cggatttgct cagtgtgcgc
9901  tggaagcggg aagggtttat ttccgatcac gcggcgcgta gtaaaggcaa agagacgccg
9961  attaatttgc tgggtttcaa agacggcact gccaatcccg atagccagaa tgataagttg
10021 atgcaaaaag tggtgtgggt aacggcagat cagcaggagc ctgcgtggac aatcggtggc
10081 agctatcagg cagtacgctt gattcagttt cgagtggaat tttgggacag aacgccgctg
10141 aaagaacagc agacgatttt tggccgtgat aagcaaaccg gtgcgccgct gggaatgcag
10201 catgagcatg atgtgcctga ttacgccagc gacccggaag ggaaggtgat cgcgctggac
10261 agccatatcc ggctggcgaa tccccgcacg gcggagagtg agtccagcct gatgctgcgt
10321 cgtggctaca gttattcact gggcgtcacc aactccgggc aactggatat ggggttgctg
10381 ttgtctgct accaacacga tctggaaaaa ggcttcctga cagtacaaaa aaggctcaat
10441 ggcgaagcgc tgaggaata cgttaaacct atcggcggcg gttatttttt tgcgctgccg
10501 ggggtgaagg acgcgaacga ttatttcgga agcgcgttat gcgggttta atgttttag
10561 gcggataagg catttgtgcg cagatgcctg atgcgacgct tgcgcgtctt atcatgccta
10621 caatcagtgc gggtttggta ggctggataa ggcgttcacg ccgcatccgg cgatcgtgca
10681 ctgatgcctg atgcaaatcc tgctgaaagc acacagcttt tttcatcact gtcatcactc
10741 tgtcatcttt c
```

MOLECULAR MARKERS

FIELD OF THE INVENTION

The present invention relates generally to nucleic acid based methods for detecting the presence of *E. coli* or *Shigella* or related microorganisms in a sample using one or more *E. coli* or *Shigella* species specific nucleotide sequences. More particularly, the present invention permits the identification of molecules capable of binding or otherwise facilitating abnormal cell growth or abnormal physiology such as found in cancer or cellular instability. The present invention further provides molecular probes for performing the nucleic-acid based methods of the invention and methods of testing and selecting nucleic acid sequences suitable for same. The methods and polynucleotides of the present invention are useful inter alia in the testing of food and water samples, for testing for genetic and cellular instability, and for testing for benign, pre-neoplastic and neoplastic disease in asymptomatic or symptomatic colorectal or gastric cancer patients or those at risk of the aforementioned conditions or those infected by Escherichieae and with other diseases or conditions.

BACKGROUND OF THE INVENTION

The identification of bacteria can be carried out using biochemical, cultural, antibody recognition and molecular biological tests (Feng P C S and Hartman P A: Fluorogenic Assays for Immediate Confirmation of *Escherichia coli*. 1982. Falkow S, Habermehl K O. ed: Rapid Methods and Automation in Microbiology and Immunology. Springer-Verlag, Berlin 1985: 30–33. AOAC Official Methods of Analysis 1995. Pepper Ill., Gerba C P and Brendecke J W: Environmental Microbiology. A laboratory Manual. Academic Press 1995.)

Food and Water Hygiene

Biochemical Test and Culture Medium

The most probable number (MPN) is the common method for the detection and quantitation of *E. coli* in foods. This method detects *E. coli* on the basis of the bacteria's ability to ferment lactose with the evolution of gas. Other non-*E. coli* organisms also ferment lactose and, therefore, several selective enrichment steps are required in order to sequentially select for coliform bacteria and *E. coli*.

This widely used MPN method has several limitations. Many clinical *E. coli* isolates are lactose negative and thus are not detected using the MPN method. The MPN method requires a minimum of about four days to determine the absence of *E. coli* in food products and about seven days are required to get confirmed results. The growth of some *E. coli*, including the serotype 0157:H7 strains, is severely inhibited by the selectivity of the EC broth at 45.5° C. and gas production in the MPN method is susceptible to interference by high levels of competitor organisms.

More rapid methods for detecting *E. coli* are needed because of the time and accuracy limitations of the MPN method. It has been reported that 94% to 97% of *E. coli* strains possess the B-D-glucuronidase that can be detected by specific hydrolysis of a synthetic substrate, 4-methylumbelliferyl-B-D-glucuronide (MUG), to a fluorescent end product. When MUG is incorporated into lauryl sulfate tryptose (LST) broth, $10^7$ to $10^8$ CFU/ml of *E. coli* will yield this fluorescent product which can be detected under longwave UV light. However, a number of enteropathogenic *E. coli* including serotype 0157:H7 strains, do not possess the B-D-glucuronidase enzyme, do not exhibit fluorescence in LST-MUG medium, and therefore yield false-negative results using the MUG method. In addition, the selectivity of the method is compromised by the fact that some *Shigella, Citrobacter, Ecterobacter, Klebsiella, Salmonella*, and *Yersinia* species also produce B-D-glucuronidase and therefore yield false-positive results.

Another widely used test, the Analytical profile index (API) test strips, produced by BioMerieux (France), may be used to obtain test results quickly. These consist of a series of miniature capsules on molded plastic strips, each of which contains a sterile dehydrated medium in powder form. Addition of water containing a bacterial suspension simultaneously re-hydrates and inoculates the medium. A rapid reaction is obtained because of the small volume of medium and the large inoculum used. The identification of the unknown bacterium is achieved by determining a seven digit profile index number and consulting the API profile recognition system. However, there are strains of *E. coli* that yield a low discrimination value with the API strips.

When this occurs, further identification with sugar test is required for affirmation. Acid production from sugars such as D-Adonitol, Cellobiose, Lactose and D-Xylose are additional biochemical test for differentiation of *Escherichia* species and related species.

DNA Probes

The use of genetic probes in the detection of microorganisms is popular because they obviate the need for pure cultures, and are specific, sensitive, fast and reliable (Fred C. Tenover: DNA probes for infectious diseases. CRC Press, Inc. 1989). In DNA probe test, it is essential to know something about the nucleotide sequence of the microorganisms under investigation.

Bacteria belonging to different families or strains can be differentiated on the basis of heterogeneity in genetic sequences. One approach is the identification and use of specific toxin genes of disease causing strains to distinguish them from the normal flora. Another approach makes use of the conserved and polymorphic sites that are found in bacterial 16S ribosomal RNA (rRNA) sequences not present in human 18 rRNA or human mitochondrial 12S rRNA. The combination of the polymerase chain reaction technique for gene amplification, followed by sequencing of polymorphic regions and phylogenetic analysis of the resulting sequence information can also assist in strain identification. (Relman et al. *The New Engl J of Medicine*, 327: 293–301, 1992, Kui et al. *FEMS Microbiology Letters* 57:19–24, 1989. DeLong et al. *Science* 243: 1360–1363, 1989).

The *E. coli* identification kit produced by gene-trak systems, Framingham, Mass., USA, uses DNA oligonucleotides that complement the 16S rRNA. This assay uses hybridization techniques to detect *E. coli*, non-coli *Escherichia fergusonii* and *Shigella* species.

Another way of identifying bacteria specific DNA probes is by using randomly cloned chromosomal fragments. This involves the cloning of restriction enzyme cleaved genomic DNA of a bacteria, and selection of specific clones by determining their hybridization profiles by hybridization against its own species-sequences and other species-sequences. Only clones that hybridize to sequences from the same species but the clones were derived from will be selected (Tenover FC: DNA Probes for Infectious Diseases. CRC Press 1989).

Gastrointestinal Infection

Colorectal cancer is one of the top three cancer killers in the world. Factors implicated in its etiology include inappropriate diet, environmental factors and lack of reliable diagnostic markers. Recently, greater understanding of the genetic predisposition to colon cancer has been achieved through the identification of genes responsible for such susceptibility (Cowell J K, ed: In Molecular Genetics of Cancer. Dunlop M G: Molecular genetics of colon cancer. 1995. 113–134). Despite intensive research efforts, the mortality rate from colorectal cancer has not declined dramatically over the last 40 years.

Markers associated with cancer initiation or progression are important in patient care. Tumours diagnosed at an early stage can usually be cured by surgical excision or polypectomy (surgical excision cures 90% of patients with adenoma or carcinomas that are confined to the mucosa). Patients with advanced disease have a poor prognosis as mortality increases to more than 90% after metastasis takes place.

The gastrointestinal tract is often exposed to a range of microorganisms. When bacteria come into contact with a susceptible host, they can establish either a transient presence, colonize the individual, infect the individual or evolve with the host. The outcome can either be harmless, acute illness or a chronic condition that may lead to a serious outcome (Gibson G R and Macfarlane G T: Human Colonic Bacteria: Role in Nutrition, Physiology, and Pathology. CRC Press, Inc., 1995).

Bacteria have been associated with inflammatory bowel disease such as ulcerative colitis and Crohn's disease (Giaffer et al. *Gut* 33:646–650, 1992, Cartun et al. *Mod Pathol* 6:212–219, 1993; Liu et al. *Gastroenterology* 108:1396–404, 1995). In addition, patients with pan-colitis of long duration are at risk of developing colorectal cancer (Wanebo H J: In Colorectal Cancer. Lev R: Precursors of Colon Carcinoma 1993; 158–163). Although frequently implicated, the role of bacteria in colon related disease remains ill-defined and controversial. The identification of bacteria in physical proximity to diseased tissue does not provide definitive proof of a causal relationship between a bacterium and the diseased condition. This is especially so when the bacteria are commonly found surrounding the tissue (Swidsinski et al. *Gastroenterology* 115:281–286, 1998), as is the case in the colon, and there is no additional information to differentiate between bacteria. It is perhaps more convincing if the bacterium can be shown to be positioned in-situ in the diseased tissue and when isolated and characterized found to possess properties that will substantiate its presence within the tissue.

The bacterium *Helicobacter pylori* is an accepted Group 1 (definite) biological carcinogen for gastric cancer and causes of related gastric conditions such as duodenal ulcer, gastric ulcer and ulcer complications. *H. pylori* attaches to and thrives on the gastric mucosa resulting in a chronic immunological response from the host. (Marshall, B. J. *Gastroenterologist* 1:241–247, 1993). It is not firmly established whether *H. pylori* has invasive properties. However, pathogenic strains have been identified that can cause epithelial cell damage and mucosal ulceration on an intragastric administration to mice (Telford et al. *J Exp Med* 179: 1653–1658, 1994) The question remains whether *H. pylori* is the only important factor in the development of gastric cancer because of its high infection/disease ratio. The current consensus is that there may be other factors other than *H. pylori* infection that are also important in gastric cancer risk (National Institutes of Health Consensus Development Panel on *Helicobacter pylori* in Peptic Ulcer Disease 1994). A separate study put forward the theory that a synergistic interaction between a non-invasive bacteria and other enteropathogens can facilitate invasion by the otherwise non-invasive bacteria (Geir Bukhowm and Georg Kapperud, *Infection and Immunity* 55:2816–2821, 1987).

Numerous in-vivo and in-vitro studies have vividly shown that microorganism carry transmissible tumorigenic genetic information. Mutagenesis in such instances is either by transposition or site-specific recombination facilitated by conjugation, transformation and transduction. This information is constantly being exploited scientifically in creating mutants (Sherratt D J (ed): Mobile genetic elements. Dale J W: Molecular genetics of bacteria. $2^{nd}$ Edition. John Wiley and Sons Ltd. Oxford University Press 1995). In 1995, Couralin et al. showed that invasive strains of *Shigella flexneri* and *E. coli* can carry out gene transfer that are stably inherited and expressed by the mammalian cell progeny (Courralin et al., *C. R. Acad. Sci. Paris* 318:1207–1212, 1995). Therefore, it is quite possible that the persistent presence of bacterial genetic sequences in the nucleus of mammalian cells can lead to genetic instability that may ultimately give rise to a tumour cell.

Bacterial invasion can stimulate similar a pattern of protein phosphorylation to that induced by growth factor (e.g. EGF) and cellular proliferative responses may then be altered with consequences for disease progression. (Galan et al. *Nature* 357:588–589, 1992). In addition, bacterial disruption of cell-cell interaction may affect cell proliferation patterns and differentiation (Epenetos A A and Pignatelli M (ed): Cell Adhesion Molecules in Cancer and Inflammation; Pignatelli et al.: Adhesion molecules in neoplasia: An overview. Chapter 1:1–13. Harwood academic publishers 1995). Cytonecrotizing factors have been identified that can cause formation of large multinucleated cells and cells spreading in tissue cultures. (Denko et al. *Experimental Cell Research* 234:132–138, 1997; Lemichez et al., *Molec Microbiol* 24:1061–1070, 1997; Machesky, L. M. and Hall, A, *TICB* 6:304–310, 1996). Accordingly, the persistence presence of bacteria can cause cellular changes leading to cell disorientation, proliferation and changes in cell morphology.

One cancer causing effect of bacteria is when *Agrobacterium tumefaciens*, a soil phytopathogen, genetically transforms plant cells by the transfer of the tumour-inducing (Ti) plasmid to the plant genome where its integration and expression result in the crown gall phenotype. A crown gall is a tumorous proliferation of plant cells which are released from normal metabolic and reproductive controls (Hughes M A: Plant Molecular Genetics. Addison Wesley Longman Ltd. 1996).

People travelling across continents may suffer from traveler's diarrhoea as the bacteria they are exposed to are not common in their county. The assays/kits that are used for detecting microorganisms in the Asia-Pacific region are imported from other continents and these imported assays/kits may not be as sensitive or as specific for the bacteria in the Asia-Pacific region.

Microorganisms transmitted by water and food usually grow in the intestinal tract of man and animals and leave the body in the faeces. Bacteria are known to possess gene sequences that make them toxigenic, hemorrhagic, invasive and adherent to tissues. Acute bacterial infection is well documented but it is still not known that if bacteria that do not cause overt symptoms but persist and remain undetected in their host can cause diseases with time. Therefore, it is important that the assays that are available are sensitive and specific for a wide range of pathogens.

The *E. coli* genetic sequence is published. (Blattner et al. *Science* 277:1453–1474, 1997). Some of its genetic sequence has homology to other bacteria (Janda J M and Abbott S L: The Enterobacteria. Lippincott-Raven Press 1998). The inventor, in accordance with the present invention, has identified *E. coli* DNA sequences which are unique to the Escherichae family and furthermore has shown that biochemical and cultural tests presently available are not adequate for detecting this family of bacteria. The present polynucleotide sequence in the genome of strains of the Escherichieae genus (*Escherichia* and *Shigella*), have proven to be more informative than the agar plates EMB, MacConkey and MUG. They can be used to detect *E. coli* that is either EMB, MacConkey or MUG negative. The sequences are also found in 0157:H7 and 029:NM strains of *E. coli*. Therefore, the present molecular markers provide improved tools for the detection and characterization of *E. coli*.

In addition, the invention permits the use of the sequence(s) to study the outcome of tissue infection in-situ. The present gene sequences are more specific than the gene-trak sequence (gene-trak systems) and the sequences can be amplified many-fold to increase their detection limit. This makes the present invention useful for studying the role of microorganism in gastrointestinal and other disease conditions. The presence of the polynucleotide sequence in cells can be located by the use of the polymerase-chain-reaction amplification technique in-situ followed by hybridization to the in-situ amplified signals with sequence specific DNA probe.

The identification of these specific polynucleotide sequence(s) that can be used to detect for the presence of strains of *E. coli* and *Shigella* and related microorganisms in food, water, fecal specimens, tissues, secretions and other biological, environmental and/or laboratory samples is important for health reasons as it enables one to check on the quality of food and water hygiene and monitor transmission of the microorganism. Sensitive detection techniques and methods for assessing the role of bacteria in clinical conditions will ultimately help in the control of harmful microorganisms.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

One aspect of the present invention provides a new use for the whole of Formula I and sequences within Formula I, as markers for species of bacteria within the Escherichieae family specifically *Escherichia coli* and *Shigella* species or related microorganisms.

Another aspect of the present invention relates to the use of the polynucleotide sequence of formula I to generate gene probes of smaller size which singularly or in combination have specificity for *E. coli* strains or related microorganisms but not necessarily specific for all the *Shigella* species.

A further aspect of the present invention provides Formula I and the smaller gene sequences within it as a means to detect the presence, in liquids, semisolids and solids combinations thereof or in aerosols or gases, of species of bacteria within the Escherichieae family specifically *E. coli* and some or all of the *Shigella* species so that high standard of sanitation can be achieved.

Yet another aspect of the present invention provides the aforementioned sequence(s) as a means to detect infection in a sample and/or a combination of samples by members of the Escherichieae family as aforementioned. Samples are defined in this invention as tissues or cells or explants of either human, animals or plant origin, such given examples being tissue/cells found in the colon, stomach, and other parts of the human or animal anatomy as well as in food, industrial and/or environmental samples.

A further aspect of the present invention provides a method for testing and identifying the various genes within formula I as new means to detect for changes in DNA content in cells infected or previously infected with the aforesaid Escherichieae family of bacteria (*E. coli* and *Shigella* species or related microorganisms). A cell is defined in this invention as a cell found in the animal and plant kingdom. Changes in DNA content in a cell in accordance with this invention includes DNA sequences found in the cell which differs by one or more nucleotide substitutions, additions and/or deletions of existing DNA or by the introduction of a heterologous DNA.

Yet another aspect of the present invention provides the aforementioned Formula I within which polynucleotide sequences are a marker for use in recognizing early cellular DNA changes associated with any one or more members of the Escherichieae family (*E. coli* and *Shigella* species and related microorganisms) in the colonic epithelium before the histology criteria for such cellular changes are detectable. Early changes are defined in this invention by the presence of at least bacterial DNA sequences that are present in high, low copy numbers or present as single copies per haploid genome in a normal population.

Still yet another aspect of the present invention provides the aforementioned Formula I within which polynucleotide sequences are a marker for use in recognizing pre-malignant changes associated with any one or more members of the Escherichieae family (*E. coli* and *Shigella* species and related microorganisms) in the colonic epithelium as defined by histology criteria for such pre-malignant tissue. Pre-malignant changes are defined in this invention by the presence of at least bacterial DNA sequences that are present in high or low copy numbers or present as single copies per haploid genome in a normal population and are supported by histology criteria.

Even still another aspect of the present invention provides the aforementioned Formula I within which polynucleotide sequences can be a marker for use in recognizing malignant changes associated with any one or more members of the Escherichieae family (*E. coli* and *Shigella* species and related microorganism) in the colonic epithelium and malignant colonic tumours residing in other tissues. Malignant changes are defined by histology criteria. Malignant changes associated with any one member of the Escherichieae family are defined in this invention by the presence of at least bacterial DNA sequences that are present in high or low copy numbers or present as single copies per haploid genome in a normal population.

Another, aspect of the present invention provides the aforementioned formula I within which polynucleotide sequences can be used as a marker for detecting pre-malignant changes associated with any one or more members of the Escherichieae family in the gastric mucosa as defined by histology criteria for such pre-malignant tissues. Pre-malignant changes are defined in this invention by the presence of at least bacteria DNA sequences that are present in high or low copy numbers or present as single copies per haploid genome in a normal population and its histology criteria for the tissue defined.

Yet another aspect of the present invention provides the aforementioned Formula I sequence within which polynucleotide sequences can be used as a marker to recognize malignant changes associated with any one or more members of the Escherichieae family in the malignant gastric tumours and malignant gastric tumours residing in other tissues. Malignant changes are defined inter alia by histology criteria. Malignant changes associated with the Escherichieae family in this invention is defined by the present of at least DNA sequences that are present in high or low copy numbers or present as single copies per haploid genome in a normal population.

Still another aspect of the present invention provides the aforementioned Formula I within which sequences can be used as markers to recognize patients that are found harboring any one or more member of the Escherichieae family relative to normal patients not haboring the same and are thus identified as marker of infection of said family that are important in patient care.

Even still another aspect of the present invention provides the aforementioned Formula I sequence within which polynucleotide sequences can be used as markers being found in colorectal cancer patients relative to normal patients and thus identified as a marker of malignant disease that is important in patient care.

Even yet another aspect of the present invention provides the aforementioned marker that is found in gastric cancer patients relative to normal patients and is thus identified as a marker of malignant disease that is important in patient care.

Another aspect of the present invention provides a marker for cellular instability and therefore a marker for predisposition to cellular carcinogenesis. Cellular instability may occur as a forerunner to cellular carcinogenesis or other condition and is characterized herein by changes in DNA content comprising one or more nucleotide substitutions, additions and/or deletions of existing DNA or by the presence of heterologous DNA.

Another aspect of the present invention provides a method of testing and selecting sequences in *E. coli* and *Shigella* species and related microorganisms as markers for use to detect changes in DNA content in cells in order to recognize cellular instability and, therefore, predisposition to cellular carcinogenesis, predisposition to colon and gastric cancer and as markers for use in recognizing benign, pre-malignant and malignant gastrointestinal tissues as optionally defined by histology criteria.

In accordance with the present invention, it is shown that Formula I comprises polynucleotide DNA sequence marker(s) for the Escherichieae family specifically *E. coli* species and *Shigella* species or related microorganisms. This Formula I and the various genes and sequence it contains allow the differentiation of the aforementioned members of the Escherichieae family from other bacteria families. In addition, the presence of such bacteria as indicated by the presence of the DNA sequences allows study of sanitation and health related matters such as infection, predisposition to cancer, cancer and cell instability.

Reference to "related microorganisms" includes microorganisms which are related at the immunological, biochemical, disease-causing, physiological or genetic levels. A derivative or mutant form of *E. coli* or *Shigella* species is an example of a related microorganism.

The present invention furthermore provides a method of testing and selecting other sequences in *E. coli* and *Shigella* species and related microorganisms as markers to test for their presence in cells with abnormal cell growth or physiology associated with cancer or a predisposition to the development of cancer.

Yet still another aspect of the present invention relates to a new use for the various polynucleotide sequences within Formula I as molecular probes in the determination of whether samples contain members of the Escherichieae family such as *E. coli* and *Shigella* species or related microorganisms.

In another aspect, the present invention provides methods for enhancement in the specificity and sensitivity of detecting the presence, among other bacteria of *E. coli* species and some of the *Shigella* species with some of the aforementioned sequences.

The presence of the polynucleotides sequences in food and water is evidence that they are contaminated with members of Escherichieae family such as *E. coli* species and probably some or all of the *Shigella* species. Thus the present molecular probes provide an alternative to microbiological and biochemical assays which are less specific, sensitive, reliable, often required for pure cultures, and are more time consuming.

A further related aspect of the present invention provides a new use for the sequences within the Formula I for determining whether tissue samples contain the DNA markers that originate from members of the *E. coli* and *Shigella* species. Both species within this family are known to have invasive, adherent and toxigenic properties. This aspect relates to the new use of polynucleotide sequence(s) within Formula I as marker(s) for detecting infection by identifying samples such as, for example, colonic and gastric mucosa tissues that contain them. The presence of the polynucleotide sequences in tissues is evident that the tissues are infected by members of the *E. coli* and *Shigella* species.

A further aspect of the instant invention relates to a new use for the sequences within the Formula I for determining which cell type within tissues samples contain marker DNA sequences that originate from members of the Escherichieae family such as *E. coli* and the *Shigella* species and related microorganisms.

A further aspect of the instant invention relates to a new use for the aforementioned polynucleotide sequence(s) within Formula I as a maker(s) for detecting changes in cellular DNA composition in, for example, colonic and gastric mucosa cells before histology criteria for changes are detectable. The presence of the polynucleotide sequences in cells of tissues is evidence that the cells are infected by members of the *E. coli* and *Shigella* species. Changes in cellular DNA composition are defined in this particular aspect of the invention by the presence of at least bacteria DNA sequences that are present in high or low copy numbers or present as single copies per haploid genome in a normal population. The polynucleotide sequence of the present invention are only found in Escherichieae family and, therefore, their presence in other species such as in eukaryotic cells, for an example, is a sign of an abnormal event. Accordingly, the present invention provides one or more molecular marker for screening patients to identify those who are at risk of having gastrointestinal tumours (benign, pre-malignant, or malignant).

A further additional aspect of the present invention relates to a new use for the sequences within the Formula I for determining whether pre-malignant tumours as defined by histology criteria contain aforementioned polynucleotides sequences that originate from members of the *E. coli* and *Shigella* species or related microorganisms. This aspect relates to the new use of the marker for detecting the presence of any one or more member of the Escherichieae family in the pre-malignant tumours such as colonic and gastric tissues as defined by histology criteria. The presence of the polynucleotide sequence in the cells of pre-malignant colonic and gastric tumours is evidence that the cells are infected by or contain DNA sequences of members of the *E. coli* and *Shigella* species. These pre-malignant tumours contain the presence of at least bacteria DNA sequences that are present in high or low copy numbers or present as single copies per haploid genome in a normal population. The polynucleotide sequence of the present invention are only found in Escherichieae family and, therefore, their presence in other species such as in eukaryotic cells, for an example, is a sign of an abnormal event. Accordingly, the present invention provides one or more molecular markers for screening patients to identify those at risk of having gastrointestinal tumours (benign, pre-malignant, malignant).

The present invention also relates to a new use for the aforementioned polynucleotide sequence(s) as a marker for determining whether malignant changes in the colonic and gastric mucosa contain marker sequences that originate from members of the *E. coli* and *Shigella* species. Malignant changes are defined by conventional histological criteria. This aspect of the invention relates to the new use of the marker for detecting the DNA presence of any one or more member of the Escherichieae family in the malignant tumours. The presence of the polynucleotide sequence in the cells of these malignant tumours is evidence that the cells are infected by or contain DNA sequences of members of the *E. coli* and/or *Shigella* species. These malignant tumours contain the presence of at least bacteria DNA sequences that are present in high, low copy numbers or present as single copies per haploid genome in a normal population. The polynucleotide sequence of the present invention are only found in Escherichieae family and, therefore, their presence in other species such as in eukaryotic cells, for an example, is a sign of an abnormal event. Accordingly, the present invention provides one or more molecular markers for screening patients having gastrointestinal tumours (benign, pre-malignant, malignant).

The instant invention provides in a related embodiment a new use for the aforementioned polynucleotide DNA sequence(s) as markers for determining the presence of any member of the *E. coli* and *Shigella* species in metastatic cells of colonic or of gastric tumour origin residing in other tissues. This aspect of the invention relates to the new use of the marker sequence for detecting the DNA presence of any one or more member of the *E. coli* and/or *Shigella* species in the metastatic cells. The presence of the polynucleotide sequence in the cells of these malignant tumours is evidence that the cells are infected by or contain DNA sequences of members of the *E. coli* and/or *Shigella* species. These metastatic cells contain the presence of at least bacteria DNA sequences that are present m high or low copy numbers or present as single copies per haploid genome in a normal population. The polynucleotide sequence of the present invention are only found in Escherichieae family and, therefore, their presence in other species such as in eukaryotic cells, for an example, is a sign of an abnormal event. Accordingly, the present invention provides one or more molecular markers for screening patients having gastrointestinal metastatic cells.

The present invention furthermore relates in a different aspect to a new use for the formula I sequence that is found in *E. coli* and *Shigella* species or in related microorganisms, as a marker for determining cells that possess it. The invention relates to the new use of the marker sequence for detecting the DNA presence of any one or more member of the *E. coli* and/or *Shigella* species in the cells. This gene sequence is only found in Escherichieae family and therefore its presence in high, low copy numbers or as single copies per haploid genome in a normal population in eukaryotic cells, for an example, is a sign of an abnormal event that may lead to genetic instability of cell that possess it. It provides as a molecular marker for risk of and genetic instability and therefore tumourigenesis.

Even more particularly the present invention, in one aspect, provides a method for detecting the presence of *E. coli* or *Shigella* species or related microorganisms in a sample, said method comprising subjecting a nucleic acid molecule preparation from said sample to genetic analysis using one or more *E. coli-* or *Shigella* species'-specific nucleotide sequences obtainable from one or more nucleotide sequences of Formula 1 and/or Table 1 wherein the ability for said *E. coli-* or *Shigella* species'-specific nucleotide sequences to hybridize to complementary nucleotide sequences in the nucleic acid preparation is indicative of the presence of *E. coli, Shigella* species or related microorganisms.

In a further aspect of the present invention there is provided a method for detecting the presence of *E. coli* and/or *Shigella* species or related microorganisms in a sample as hereinbefore described wherein the nucleotide sequences of Formula I comprises from nucleotide position 246 of GenBank Accession No. AE000201 to nucleotide position 6693 of GenBank Accession No. AE000203 including the nucleotide sequence of GenBank Accession No. AE000202.

Still a further aspect of the present invention provides a method for detecting the presence of *E. coli* or *Shigella* species or related microorganisms in a sample as hereinbefore described wherein the *E. coli-* and/or *Shigella* species'-specific nucleotide sequences comprises at least 8 nucleotides in length.

A related aspect of the present invention discloses a method for detecting the presence of *E. coli* or *Shigella* species or related microorganisms in a sample as hereinbefore described wherein hybridization of *E. coli-* and/or *Shigella* species'-specific nucleotide sequences to the nucleic acid preparation is detected by the presence of amplified nucleic acid products.

A further related aspect of the present invention provides a method for detecting the presence of *E. coli, Shigella* species or related microorganisms in a sample wherein hybridization of *E. coli-* and/or *Shigella* species'-specific nucleotide sequences to the nucleic acid preparation or the presence of amplified nucleic acid products is detected by a reporter molecule giving an identifiable signal.

Still yet a further related aspect of the present invention provides a method for detecting the presence of *E. coli, Shigella* species or related microorganisms in a the sample wherein the sample comprises food, water, semi-solids or semi-liquid material, mammalian tissue, tissue extract or cells of tissue or normal tissue or tissue predisposed to cancer growth or malignancy or cellular instability.

In a particularly preferred aspect of the present the mammalian tissue is associated with colon, stomach or colorectal tissue.

A related aspect of the present invention provides a method for identifying nucleotide sequences, or their expressed products, capable of inducing or otherwise facilitating abnormal cell growth or abnormal physiology, said method comprising introducing a nucleotide sequence comprising *E. coli-* and/or *Shigella* species'-specific nucleotide sequences from the nucleotide sequences in Formula I into cells and observing morphological and/or physiological changes to said cells compared to control cells without said introduced nucleotide sequences wherein the presence of abnormal morphology and/or physiology in a cell is indicative of a nucleotide sequence from Formula I, or a polypeptide expressed therefrom, which is capable of inducing or facilitating abnormal cell growth or physiology.

In a further preferred aspect of the instant invention the abnormal cell growth or physiology is associated with cancer or a predisposition to the development of cancer or cellular instability.

A further aspect of the present invention provides a molecular probe comprising at least 8 nucleotides obtainable from the nucleotide sequences of Formula I wherein said molecular probe is capable of specifically hybridizing to *E. coli*- and/or *Shigella* species'-derived nucleic acid molecules.

Yet more particularly the present invention encompasses a use of a nucleotide sequence obtainable from the nucleotide sequence of Formula I in the manufacture of a molecular probe for the identification of *E. coli* and/or *Shigella* species and/or for the identification of a cellular instability or a cancer or tumor or a predisposition to development of same.

Still even yet more especially the present invention provides a method for testing and selecting other sequences in *E. coli*, *Shigella* species or related microorganisms in a sample, said method comprising subjecting a nucleic acid molecule preparation from said sample to genetic analysis using one or more *E. coli* or *Shigella* species'-specific nucleotide sequences obtainable from one or more nucleotide sequences of Formula 1 and/or Table 1 wherein the ability for said *E. coli*- or *Shigella* species'-specific nucleotide sequences to hybridize to complementary sequences in the nucleic acid preparation is indicative of an *E. coli* or *Shigella* species'-specific nucleotide sequence.

Another aspect of the instant invention provides a molecular probe of at least 8 nucleotides, identified by the methods as herein described wherein said probe comprises a sequence of nucleotides from Formula I and wherein said molecular probe is capable of specifically hybridizing to *E. coli* and/or *Shigella* species'-derived nucleic acids.

The invention still yet provides the use of a nucleotide sequence identified by the methods herein disclosed in the manufacture of a molecular probe for the identification of *E. coli*, *Shigella* species and/or for the identification of a cellular instability or a cancer or tumour or a predisposition to development of same.

A related aspect of the instant invention discloses a use of a nucleotide sequence specific to *E. coli* and/or *Shigella* species and/or related microorganism in the manufacture of a molecular probe for the identification of one or more gastrointestinal cancers or tumours or a predisposition to the development of same.

A final preferred aspect of the instant invention provides a molecular probe comprising a nucleotide sequence specific to *E. coli* and/or *Shigella* species and/or related microorganism for the identification of one or more gastrointestinal cancers or tumours or a predisposition to same.

Other aspects, features and advantages of the present invention will become apparent from the detailed description that follows, or may be learned by practice of the invention.

For the sale of brevity, reference to specific microorganisms such as *Escherichia coli* (*E. coli*) or *Shigella* species includes reference to related microorganisms.

BRIEF DESCRIPTION OF THE DRAWINGS

The accompanying figures serve to further explain the principles of the instant invention. It is to be understood, however, that the figures are designed for purposes of illustration only, and not as a definition of the limits of the invention for which reference should be made to the claims appearing at the end of the description.

FIGS. 1*a*–*c*. Schematic diagram of the various locations of the genes tested that is within the polynucleotide sequence of formula I. The formula I sequence extends from nucleotide position (nt) 246 of GenBank accession #AE000201, including sequence of GenBank accession #AE000202 to nucleotide position 6693 of GenBank accession #AE000203.

FIG. 2. Autoradiograph result of probe A hybridizing to a panel of bacteria DNA as listed in Table 2a grid C. Probe A consists of fragments 1,2,3 and 4 as depicted in FIG. 1, *a*–*c*. Each fragment is generated by primer directed PCR carried out on K12 *E. coli* DNA and subsequently combined for $^{32}$P labeling and hybridization. The gene sequence spans between nucleotide position 1163 of AE000201 through AE000202 to 503 of AE000203. The primer pairs used are: ECM-1163, torT-5750 (fragment 1, AE000201); torT-5129 AE000201, CD-1351 AE000202 (fragment 2); CD-415, ycdG 7359 (fragment 3, AE000202); ycdG-6073 AE000202, New2-503 AE000203 (fragment 4). Five hundred nanogram DNA is loaded per dot. Post hybridization wash condition is 1×SSC, 0.1% w/v SDS, 20 mM Na pyrophosphate at 65° C.

FIG. 3. Autoradiograph result of radiolabeled gene probe hybridized to bacteria DNA as listed in Table 2a grid A. The gene sequence spans between nucleotide position 246 to 850 of AE000201. ECM-246 and ECM-850 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM NA pyrophosphate at 65° C.

FIG. 4. Autoradiograph result of radiolabeled gene probe hybridized to bacteria DNA as listed in Table 2a grid B. The gene sequence spans between nucleotide position 1163 to 1958 of AE000201. ECM-1163 and ECM-1958 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 5. Autoradiograph result of radiolabeled gene probe hybridized to bacteria DNA as listed in Table 2a grid A. The gene sequence spans between nucleotide position 7218 to 7761 of AE000201. Primers tor C-7218 and tor C-7761 are used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 6. Autoradiograph result of radiolabeled gene probe hybridized to bacteria DNA as listed in Table 2a grid A. The gene sequence spans between nucleotide position 8332 to 8891 of AE000201. Primers tor A-8332 and tor A-8891 are used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 7. Autoradiograph result of radiolabeled gene probe hybridized to bacteria DNA as listed in Table 2a grid B. The gene sequence spans between nucleotide position 10574 to 11160 of AE000201. Primers tor D-10574 and tor D-11160 are used to generate the gene probe by PCR amplification of K12 *E. coli* genomic DNA. Five hundred nanogram DNA is loaded per dot. Post hybridization wash condition is 0.1× SSC, 0.1% w/v SDS, 20 mM Na pyrophosphate at 65° C.

FIG. 8. Autoradiograph result of radiolabeled gene probe hybridized to bacteria DNA as listed in Table 2a grid A. The gene sequence spans between nucleotide position 415 to 1351 of AE000202. CD-415 and CD-1351 are the primers used to generate the gene probe by PCR amplification of K12 *E. coli* genomic DNA. Five hundred nanogram DNA is loaded per dot. Post hybridization wash condition is 0.1× SSC, 0.1% w/v SDS, 20 mM Na pyrophosphate at 65° C.

FIG. 9. Autoradiograph result of radiolabeled gene probe hybridized to bacteria DNA as listed in Table 2a grid B. The gene sequence spans between nucleotide position 3151 to 4359 of AE000202. Primers agp-3151 and agp4359 are used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 10. Autoradiograph result of radiolabeled gene probe hybridized to bacteria DNA as listed in Table 2a grid C. The gene sequence spans between nucleotide position 4807 to 5235 of AE000202. Wrb-4807 and Wrb-5235 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 11. Autoradiograph result of radiolabeled gene probe hybridized to bacteria DNA as listed in Table 2a grid A. The gene sequence spans between nucleotide position 6073 to 7359 of AE000202. Primers ycdG-6073 and ycdG-7359 are used to generate the gene probe by PCR amplification of K12 *E. coli* genomic DNA. Five hundred nanogram DNA is loaded per dot. Post hybridization wash condition is 0.1× SSC, 0.1% w/v SDS, 20 mM Na pyrophosphate at 65° C.

FIG. 12. Autoradiograph result of radiolabeled gene probe hybridized to bacteria DNA as listed in Table 2a grid A. The gene sequence spans between nucleotide position 7223 to 7794 of AE000202. 81B-7223 and 81B-7794 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 13. Autoradiograph result of radiolabeled gene probe hybridized to bacteria DNA as listed in Table 2a grid B. The gene sequence spans between nucleotide position 7278 to 7773 of AE000202. 81B-7278 and 81B-7754 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 14. Autoradiograph result of radiolabeled gene probe hybridized to bacteria DNA as listed in Table 2a grid C. The gene sequence spans between nucleotide position 7419 to 7985 of AE000202. OH-7419 and OH-7985 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 15. Autoradiograph result of radiolabeled gene probe hybridized to bacteria DNA as listed in Table 2a grid B. The gene sequence spans between nucleotide position 7562 to 7794 of AE000202. OH-7562 and 81B-7794 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 16. Autoradiograph result of radiolabeled gene probe hybridized to bacteria DNA as listed in Table 2a grid C. The gene sequence spans between nucleotide position 8160 to 9704 of AE000202. New1-8160 and New1-9704 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 MM Na pyrophosphate at 65° C.

FIG. 17. Autoradiograph result of radiolabeled gene probe hybridized to bacteria DNA as listed in Table 2a grid B. The gene sequence spans between nucleotide position 9731 to 11375 of AE000202. New2-9731 and B-11375 are the primers used to generate the gene probe by PCR amplification of K12 *E. coli* genomic DNA. Five hundred nanogram DNA is loaded per dot. Post hybridization wash condition is 5×SSC, 0.05% w/v SDS, 20 mM Na pyrophosphate at 65° C.

FIG. 18. Autoradiograph result of radiolabeled gene probe hybridized to bacteria DNA as listed in Table 2a grid C. The gene sequence spans between nucleotide position 9731 of AE000202 to 503 of AE000203. New 2-9731 and New2-503 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 19. Autoradiograph result of radiolabeled gene probe hybridized to bacteria DNA as listed in Table 2a grid B. The gene sequence spans between nucleotide position 5944 to 6693 of AE000203. Primers putP-5944 and putP-6693 are used to generate the gene probe by PCR amplification of K12 *E. coli* genomic DNA. Five hundred nanogram DNA is loaded per dot. Post hybridization wash condition is 1×SSC, 0.1% w/v SDS, 20 MM Na pyrophosphate at 65° C.

FIG. 20. Autoradiograph result of radiolabeled probe A hybridized to Enterobacter cloacae and K12 *E. coli* genomic DNA as depicted in Table 2a grid E. Post hybridization wash condition is 1×SSC, 0.1% w/v SDS, 20 mM Na pyrophosphate at 65° C.

FIG. 21. Autoradiograph result of radiolabeled gene probe hybridized to Enterobacter cloacae and K12 *E. coli* genomic DNA as depicted in Table 2a grid E. The gene sequence spans between nucleotide position 7562 to 7794 of AE000202. OH-7562 and 81B-7794 are the primers used to generate the gene probe by PCR amplification of K12 *E. coli* genomic DNA. Post hybridization wash condition is 1×SSC, 0.1% w/v SDS, 20 mM Na pyrophosphate at 65° C.

FIG. 22. Autoradiograph result of radiolabeled gene probe hybridized to Enterobacter cloacae and K12 *E. coli* genomic DNA as depicted in Table 2a grid E. The gene sequence spans between nucleotide position 7223 to 7794 of AE000202. 81B-7223 and 81B-7794 are the primers used to generate the gene probe by PCR amplification of K12 *E. coli* genomic DNA. Post hybridization wash condition is 1×SSC, 0.1% w/v SDS, 20 mM Na pyrophosphate at 65° C.

FIG. 23. Autoradiograph result of radiolabeled gene probe hybridized to bacteria DNA as listed in Table 2a grid D. The gene sequence spans between nucleotide position 7278 to 7773 of AE000202. 81B-7278 and 81B-7754 are the primers used to generate the gene probe by PCR amplification of K12 *E. coli* genomic DNA. Five hundred nanogram DNA is loaded per dot. Post hybridization wash condition is 1×SSC, 0.1% w/v SDS, 20 mM Na pyrophosphate at 65° C.

FIG. 24 Autoradiograph result of $^{32}$P radiolabeled *H. pylori* ribosomal gene probe hybridized to bacteria DNA as listed in Table 2a grid A. Primer pairs indicated are used for PCR amplification of *H. pylori* genomic DNA to generate the required gene segment. Five hundred nanogram of genomic DNA is loaded per dot. Post hybridization wash condition is 0.1×SSC, 0.1% w/v SDS, 20 mM Na pyrophosphate at 65° C.

FIG. 25. Autoradiograph result of $^{32}$P radiolabeled *H. pylori* ribosomal gene probe hybridized to bacteria DNA as listed in Table 2a grid D. Primer pairs indicated are used for PCR amplification of *H. pylori* genomic DNA to generate the required gene segment. Five hundred nanogram of genomic DNA is loaded per dot. Post hybridization wash condition is 0.1×SSC, 0.1% w/v SDS, 20 mM Na pyrophosphate at 65° C.

FIG. 26. Autoradiograph result of in vitro simulated PCRISH. *H. pylori* $^{32}$P radiolabeled ribosomal gene probe is hybridized to products generated from its primer directed PCR amplification of *H. pylori* and *E. coli* genomic DNA and total DNA of *H. pylori* and *E. coli* isolates obtained from patients' fecal specimens. The post hybridization wash condition is 5×SSC, 0.05% w/v SDS, 20 mM Na pyrophosphate at 65° C. See Table 2a grid F.

Figure 1A:
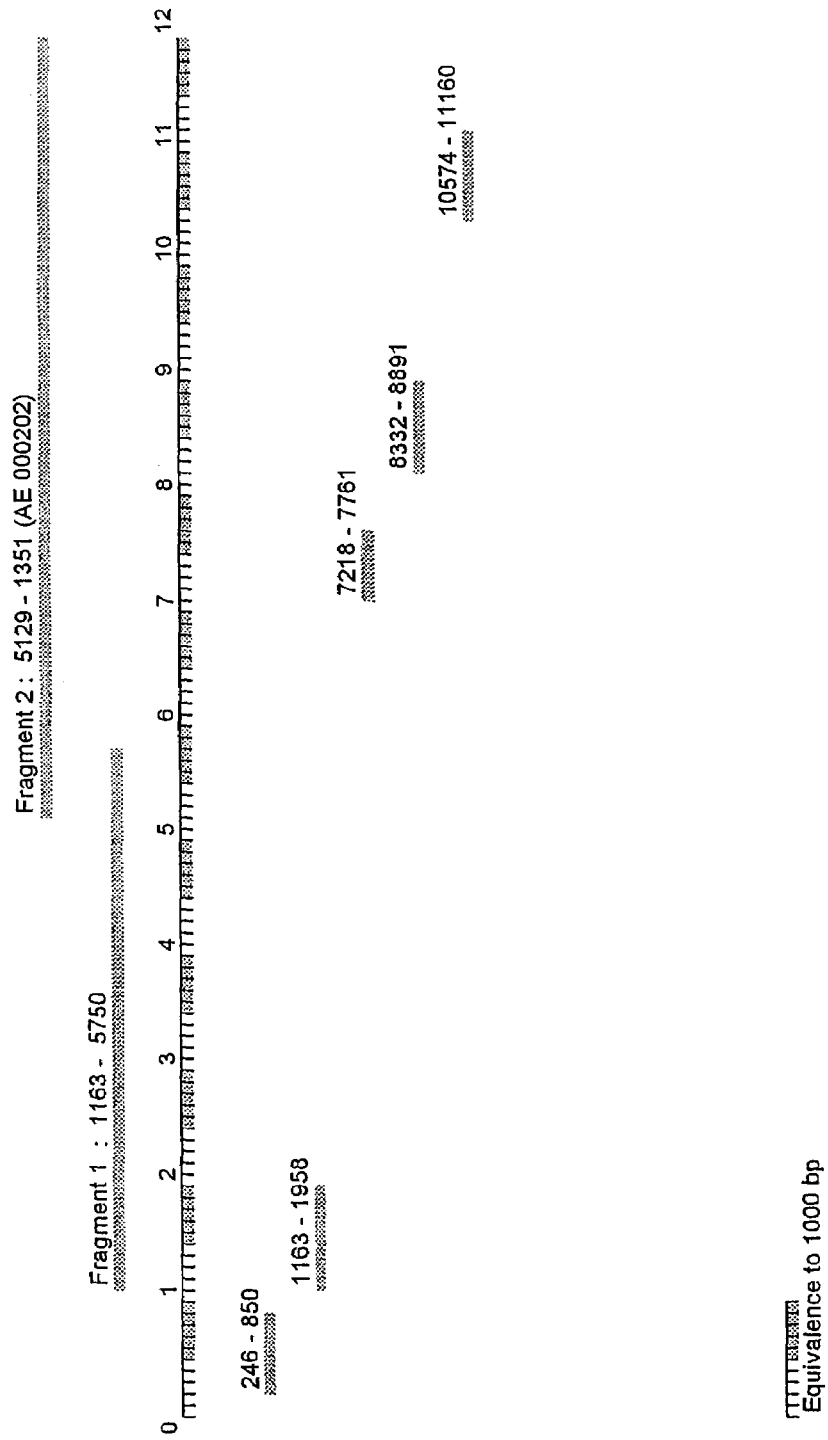

Table 1. Oligonucleotide Primers.

Table 2a. Grids A,B,C show the different types of bacteria genomic DNA loaded onto corresponding nylon plus membrane and hybridized to random primed $^{32}$P-radiolabeled gene probes. Columns W to Y for all three grids have the same panel of bacteria DNA. Column Z as indicated, has only a few bacteria DNA that is common among them. DNA of *E. coli* isolates obtained from patient fecal specimens are: 219/1, 196/1, 196/28, 197/5, 218/40, 142/31, 179/36, and 117/3B. Patient's *Shigella* sonnei isolate is 219/1. 078:H11 and 0157:H7 are commercial *E. coli* strains. TG2 is a gift from Gibson T J. Placental DNA is from commercial source (Sigma, UK). SssDNA is sonicated denatured salmon sperm DNA (Sigma, UK). These membranes exist in replicates and are hybridized to different radio-labeled gene probes. 500 ng DNA is loaded per dot.

Table 2a. Grid D correspond to nylon plus membrane that contain DNA from *E. coli* and gram positive bacteria isolated from patients' fecal specimen. Unless otherwise stated, all are *E. coli* DNA. Placental DNA, K12 and 0157:H7 are from commercial source. 114/3 g is *Streptococcus* group D DNA, 115/TA is *Streptococcus* group G DNA, 116/TC is *Aeromonass sobria* DNA, 116/TD is *Streptococcus viridans* DNA, 117/2D is *Streptococcus* group D DNA, 154/9 is unidentified gram positive bacteria DNA and HP is *Helicobacter pylori* DNA. 500 ng DNA is loaded per dot.

Table 2a. Grid E correspond to nylon plus membranes that contain in duplicate a range of different amount of Enterobacter cloacae and K12 *E. coli* DNA. The membranes are then hybridized to different $^{32}$P-radiolabeled gene probes to determine the level of crossover between the 2 different species of bacteria.

Table 2a. Grid F correspond to nylon plus membrane that contains different amount of *E. coli* DNA, *H. pylori* DNA and *H. pylori* primer directed PCR product of *E. coli* and *H. pylori* DNA. This is hybridized to $^{32}$P radiolabeled *H. pylori* ribosomal gene probe (HP).

Table 2b. Bacteria source.

Table 3. Result of in-vitro simulation of PCRISH. The primer directed PCR amplification of bacteria DNA has resulted in amplification of product(s). This is indicated by the appearance of band(s) upon gel resolution of a given aliquot of a post PCR mixture (not shown). Post PCR mixture having multiple bands is denoted as positive if any one DNA band migrates at the expected molecular weight of the intended target product. Hybridization with corresponding radiolabeled gene probe has not picked up any non-specific bands other than the single band of the intended target.

FIGS. 27–34: Detection of bacteria DNA in biopsies and surgical specimens obtained from the colon by polymerase-chain-reaction-in-situ-hybridization technique (PCRISH). For the detection of 81B gene sequence (marker for *E. coli/Shigella* species except *Shigella boydii*) PCR in-situ amplification is carried out with outer primers 81B-7223 and 81-7794. The PCR digoxigenin labeled 81B gene probe is made with inner primers 81B-7278 and 81B-7754. For detection of *H. pylori* ribosomal gene sequence, PCR in situ amplification is carried out with the outer primers HP-178 and HP-775. The PCR digoxigenin labeled *H. pylori* Probe is made with inner primers HP-228 and HP-513. Positive signals are denoted by the dark spots and an example is highlighted by the arrow. Tissue condition is defined by histologic criteria.

FIG. 27: Hyperplastic polyp with no evidence of malignancy tested with 81B probe.

FIG. 28: Adenomatous polyp, tubulovillous type tested with 81B probe.

FIG. 29: Well differentiated adenocarcinoma tested with 81B probe.

Figure 30:
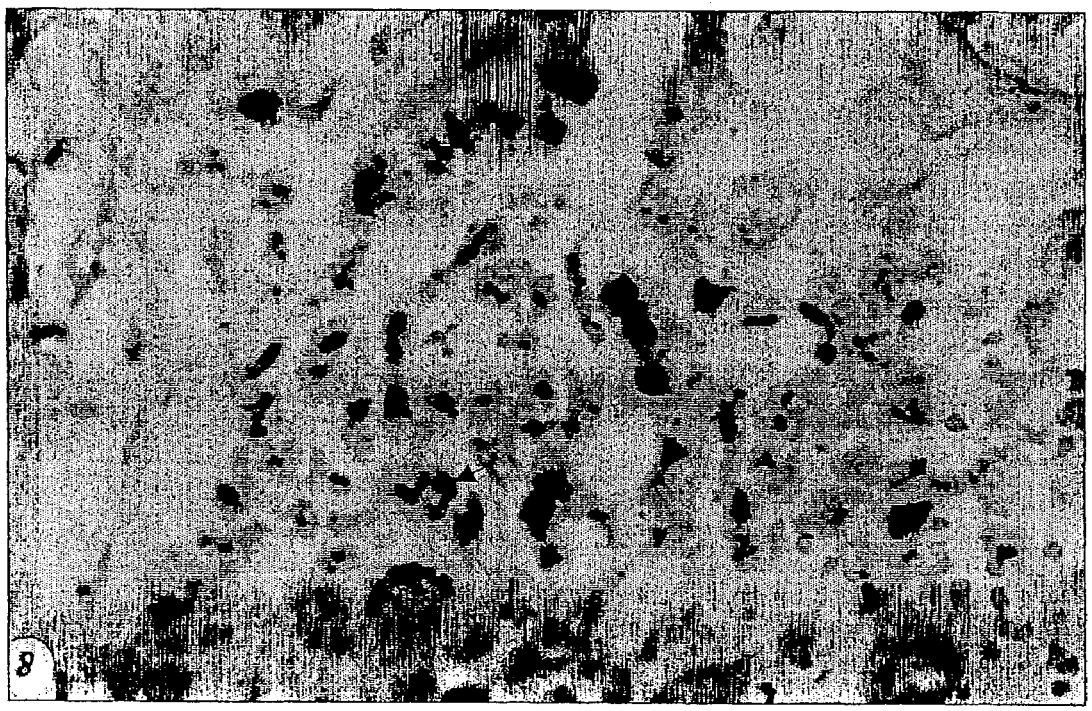

FIG. 30: Liver tissue: metastatic, poorly differentiated adenocarcinoma with primary in the gastrointestinal/pancreatico-biliary tract tested with 81B probe.

Figure 31:

FIG. 31: Normal mucosa next to tumour tested with 81B probe.

Figure 32:
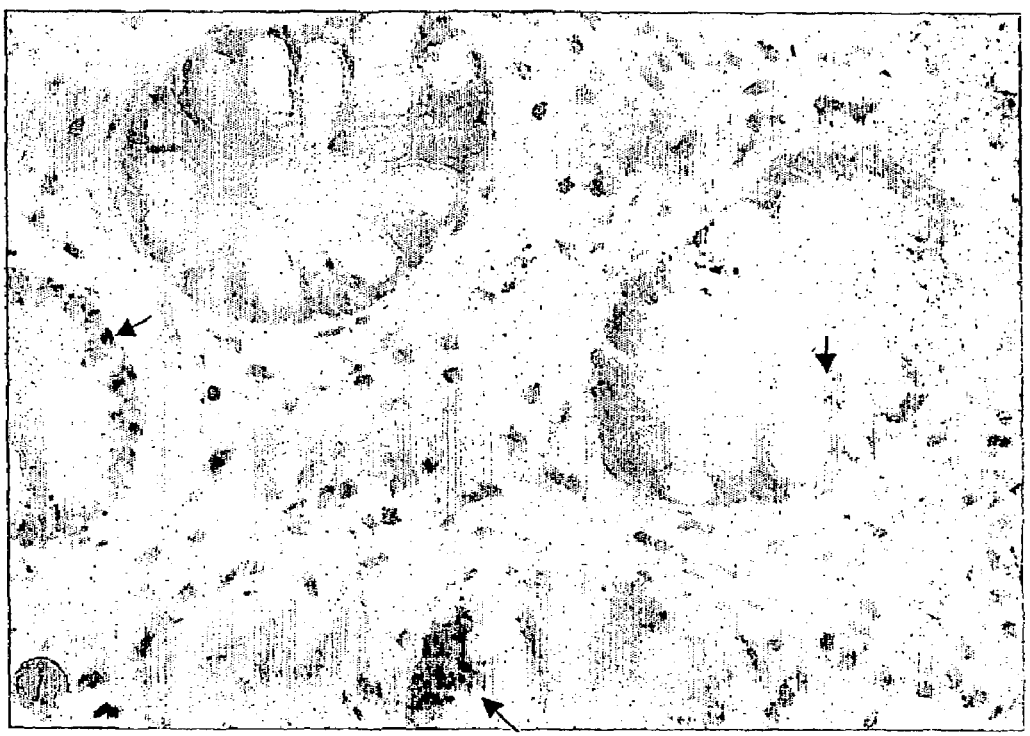

FIG. 32: Normal mucosa tested with 81B probe.

Figure 33:
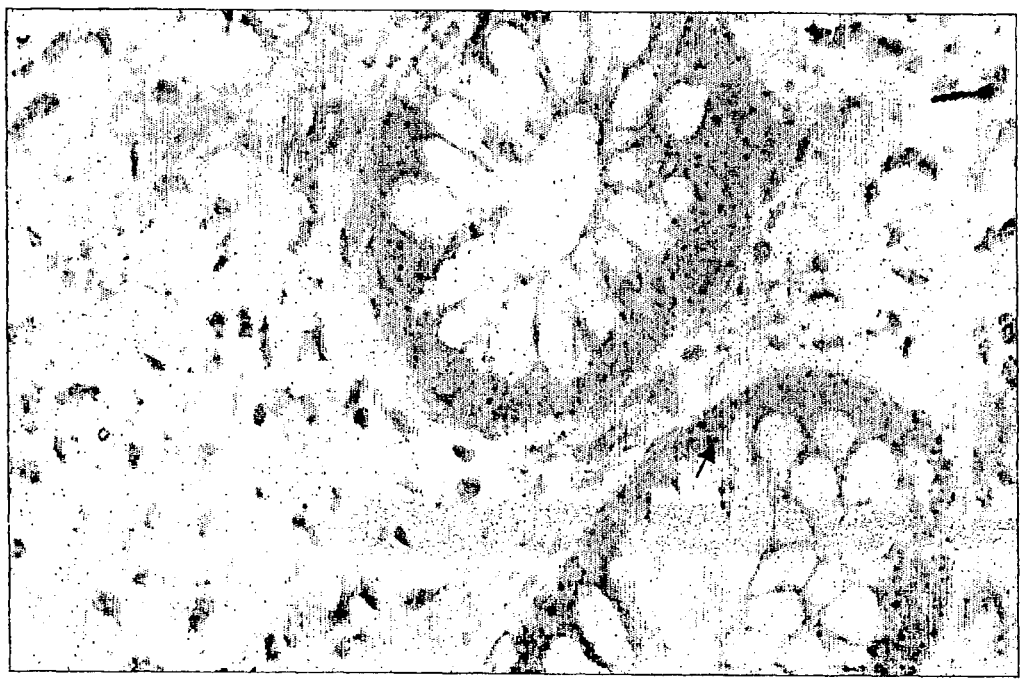

FIG. 33: Colonic mucosa diagnosed with proctitis tested with 81B probe.

Figure 34:
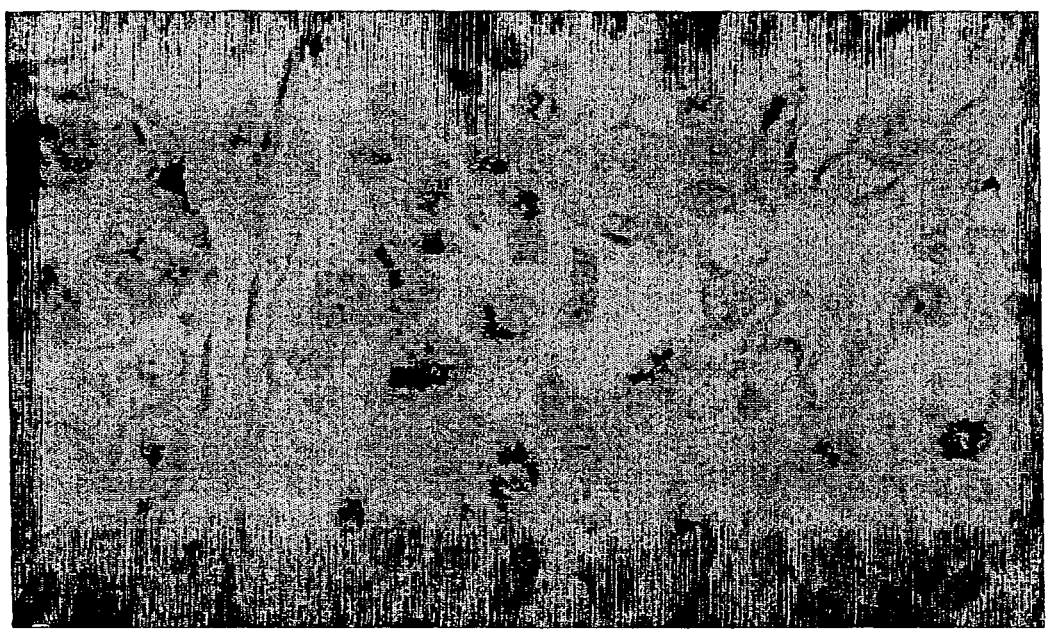

FIG. 34: Liver specimen: metastatic, poorly differentiated adenocarcinoma with primary in the gastrointestinal/pancreatico-biliary tract. Specimen tested negative with *H. pylori* ribosomal gene probe.

FIGS. 35–44: PCRISH detection of 81B DNA (marker for *E. coli/Shigella* except *Shigella boydii*) and *H. pylori* DNA in biopsies and surgical specimens obtained from the stomach. *H. pylori* Probe has not been tested against closely related Helicobacter species, and therefore does not claim to detect only *H. pylori*. Positive signals are denoted by the dark spots and an example is highlighted by the arrow. PCR in-situ amplification is carried out with outer primers 81B-7223 and 81B-7794 for the detection of the 81B gene and HP-178 and HP-775 for the detection of *H. pylori* gene. The PCR digoxigenin labeled 81B gene probe is made with inner primers 81B-7278 and 81B-7754, while HP-228 and HP-513 Primers are used for the *H. pylori* gene probe. Tissue condition is defined by histologic criteria.

FIG. 35: Adenocarcinoma of stomach tested with 81B probe.

Figure 36:
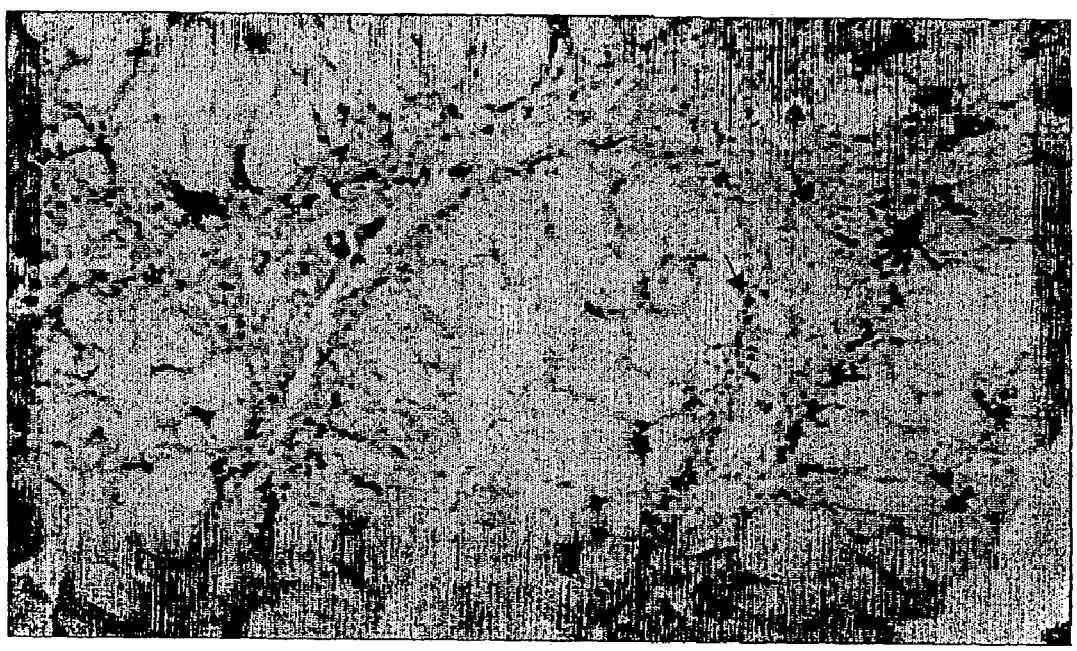

FIG. 36: Normal gastric mucosa adjacent to gastric tumour tested with 81B probe.

Figure 37:
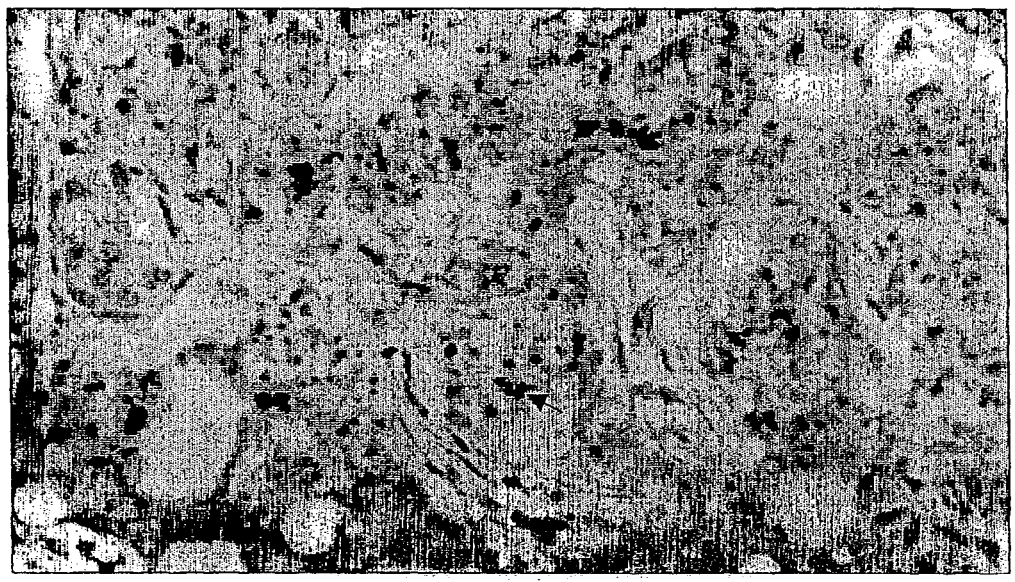

FIG. 37: Liver specimen: metastatic, poorly differentiated adenocarcinoma from gastric cancer, tested with 81B probe.

Figure 38:

FIG. 38: *H. pylori* negative normal gastric mucosa tested with 81B probe.

Figure 39:
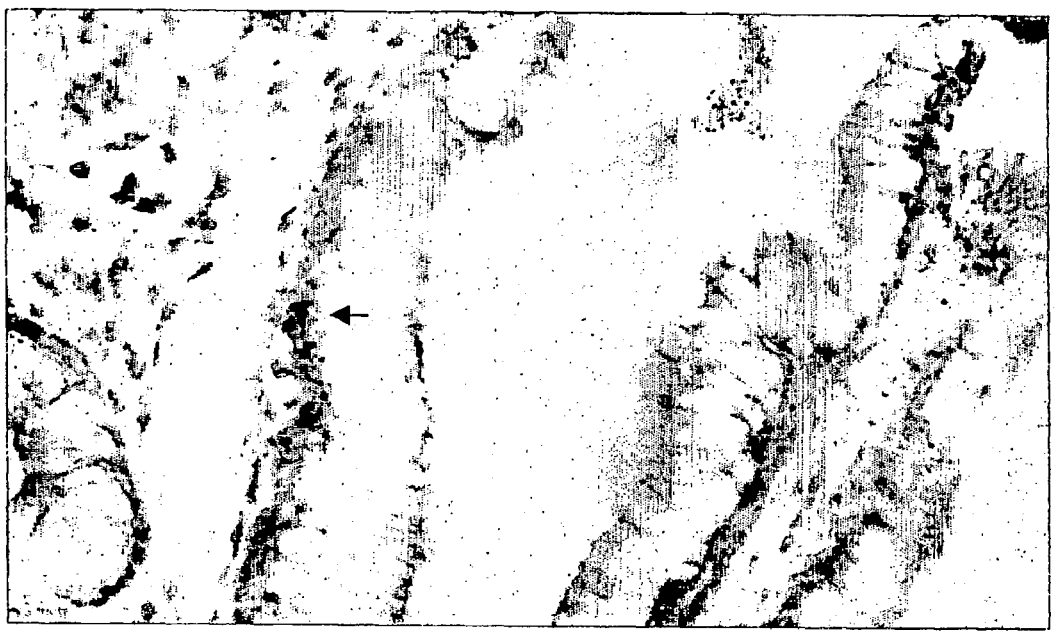

FIG. 39: *H. pylori* negative normal gastric mucosa tested with 81B probe. Specimen is the same as the one shown in FIG. 38 but showing a different area.

Figure 40:
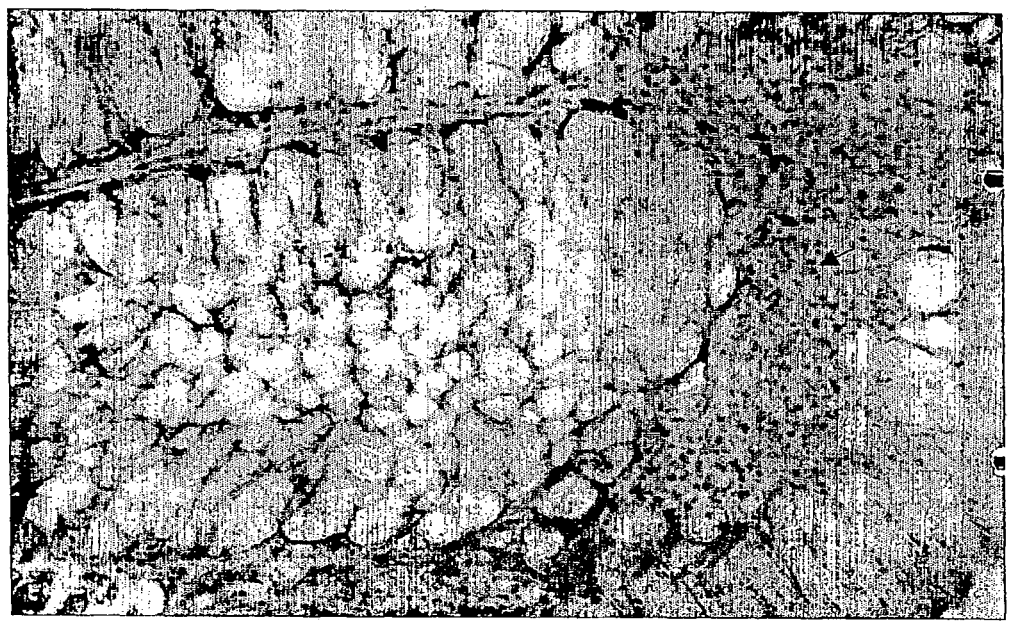

FIG. 40: Normal gastric mucosa adjacent to gastric tumour tested with *H. pylori* Probe.

Figure 41:
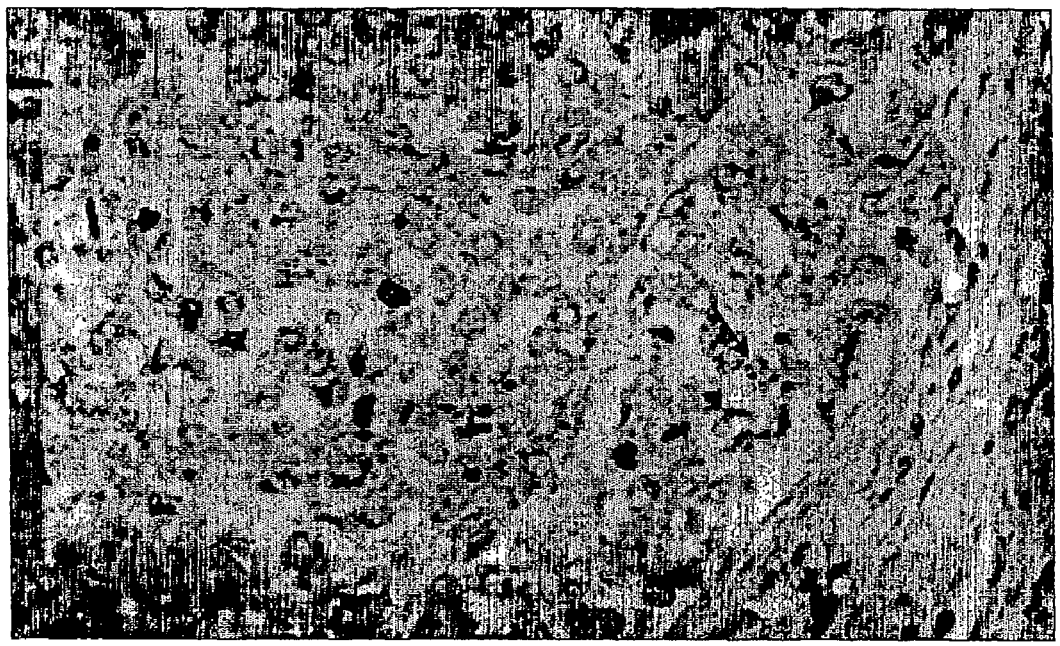

FIG. 41: Adenocarcinoma of stomach tested with *H. Pylori* probe.

Figure 42:
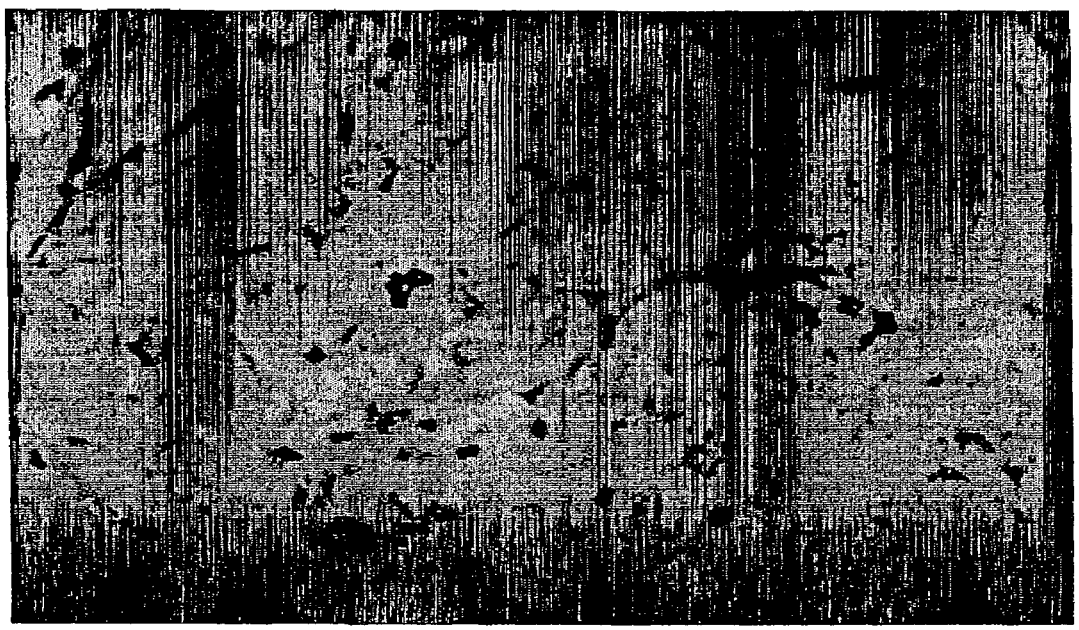

FIG. 42: Liver specimen: metastatic, poorly differentiated adenocarcinoma from gastric cancer tested with *H. pylori* Probe.

Figure 43:
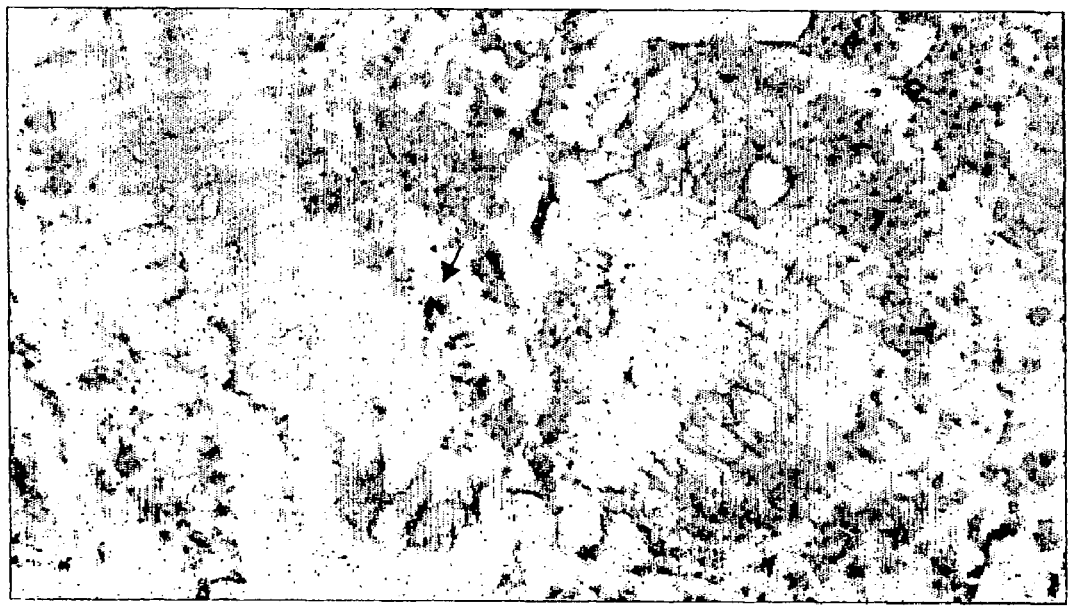

FIG. 43: Active chronic gastritis in the presence of *H. pylori* and tested with *H. pylori* probe.

Figure 44:
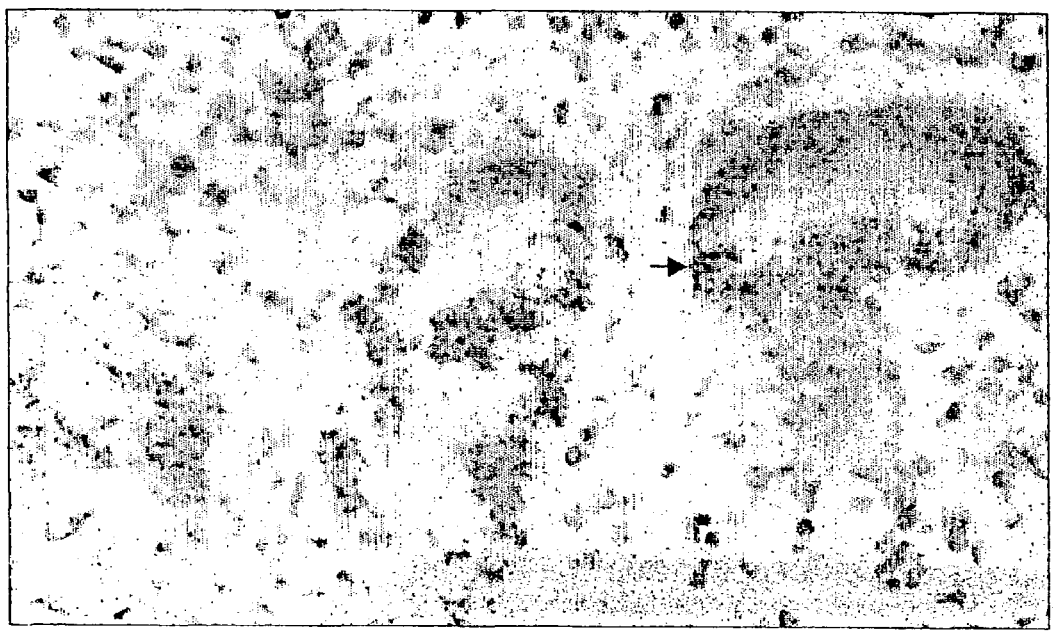

FIG. 44: Active chronic gastritis in the presence of *H. pylori*, tested with 81B probe.

FIG. 45: GenBank Accession Nos. AE000201, AE000202 and AE000203 comprising respectively sections 91, 92 and 93 of 400 of the complete genome sequences of *Escherichia coli* K-12.

DETAILED DESCRIPTION OF THE INVENTION

Figure 1B:
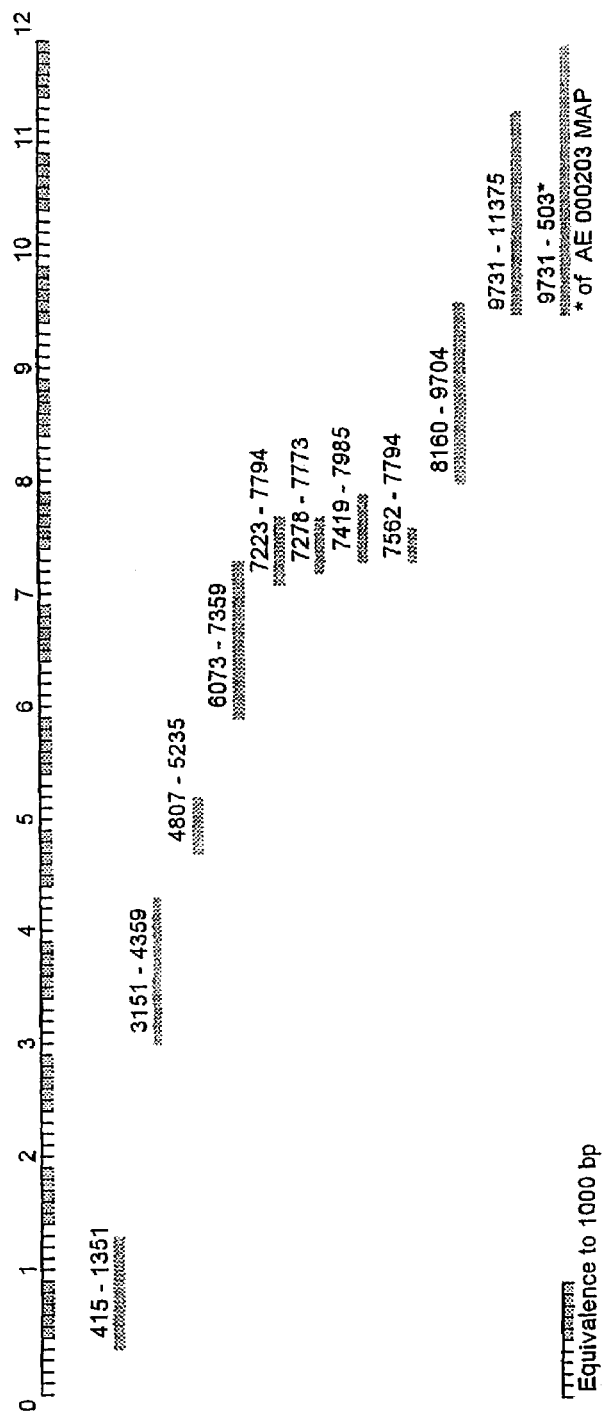

The invention herein identifies inter alia a new use for Formula I and nucleotide sequences that are part of Formula I (FIG. 1, *a–c*) as molecular markers. The Formula I sequence extends from nucleotide position (nt) 246 of GenBank accession #AE000201, including sequence of GenBank accession #AE000202 to nucleotide position 6693 of GenBank accession #AE000203.

The various DNA fragments for use as hybridization probes can be generated by polymerase chain reaction (PCR) using the primer sequences tabulated in Table 1. In this invention the various DNA fragments are shown to have a new use for identifying bacteria in the Escherichieae family such as *E. coli* and *Shigella* species. Each DNA fragment generated is specific for *E. coli* species and some *Shigella* species as some of the gene sequences show different specificity towards *Shigella boydii* and *Shigella Flexneri* (Table 2a, FIG. 2–19).

The DNA fragments highlighted in this invention as examples, and including Formula 1, can be use in detecting the aforementioned bacteria presence in liquids, solids, semi-solids to identify the level of sanitation, in monitoring the level/depth of infection, in studying the association of the presence of sequences within Formula I in gastrointestinal conditions or other clinical conditions where their presence/aforementioned bacteria is sought. The invention finds particular utility in monitoring for the presence of metastatic gastric and/or colon tumour cells. In addition, it can be used to study the association of such aforementioned sequences with gastrointestinal cancer risk. In addition, it can be used for studying the stability of genome sequence in cells that contains sequences of Formula I whether in parts, complete or in association with sequence upstream or downstream of Formula I as can be obtained in the published sequence of *E. coli* strains (example of source: GenBank database). Furthermore, the invention shows that when the sequences of Formula I are found inside cells of tissues, it is useful to identify specimens where the pathogen can be isolated and identified by probing with gene sequences for pathogenic properties, especially when the pathogen does not cause overt symptoms.

Accordingly, one aspect of present invention provides a method for detecting the presence of *E. coli* or *Shigella* species or related microorganisms in a sample, said method comprising subjecting a nucleic acid molecule preparation from said sample to genetic analysis using one or more *E. coli*- or *Shigella* species'-specific nucleotide sequences obtainable from one or more nucleotide sequences of Formula 1 and/or Table 1 wherein the ability for said *E. coli*- or *Shigella* species'-specific nucleotide sequences to hybridize to complementary nucleotide sequences in the nucleic acid preparation is indicative of the presence of *E. coli*, *Shigella* species or related microorganisms.

In a particularly preferred embodiment Formula I comprises from nucleotide position 246 of GenBank Accession No. AE000201 to nucleotide position 6693 of GenBank Accession No. AE000203 including the nucleotide sequence of GenBank Accession No. AE000202.

Specificity of DNA Probe.

The invention herein describes Formula I and the various genes it encodes, which characteristically permit identification of members of the Escherichieae family especially *E. coli* species and *Shigella* species.

The various DNA gene probes are generated by primer directed PCR amplification carried out on *E. coli* genomic DNA. The choice of primer sequence is assisted with the use of the software programme, PCR PLAN (PC/Gene system, Intelligenetics, Inc. USA) as applied on the published sequence of *E. coli* obtained from GenBank database accession #AE000201, #AE000202, and #AE000203. The suitability of a gene probe will depend on its specificity. The specificity of the primer sequence and gene probe will have to be determined empirically in a step-wise systematic fashion along the Formula I sequence or by use of software programmes. The gene fragment generated by primer directed PCR or the primer sequence should preferably be without degeneracy when tested on the panel of bacteria of related species. For the gene fragment, any variation observed is further characterized so that the variation is consistent with a particular strain or species (e.g. *E. coli* versus *Shigella*) but yet having homology to the test probe. Each gene probe fragment is preferably purified after amplification to ensure specificity.

There are many ways of obtaining such bacteria-specific fragments: this can be achieved, for example, by cloning the bacteria DNA, either in parts or complete, and screening with oligonucleotide or genomic probes of *E. coli*. The species or strain specificity of the cloned probes is determined.

The dot blot format (96 well dot-blot manifold, Bio-Rad, USA) is used here for creating a panel of bacteria genomic DNA to test for the specificity of the DNA probes (Table 2a). Reference strains are obtained from American Type Culture Collection (Table 2b. ATCC, Rockville, Md., USA). A representative bacteria from each member of the enterobacteriaceae family is chosen for the panel on which the probes are to be tested against. Gram-negative and gram-positive microorganisms obtained from subjects/patients are used as test samples (Table 2a, grid D). The reference strain and test strains are streaked for isolation, colony purified, and verified by analytical profile index test strips (API, bioMerieux, USA) and if required additional sugar test (acid production test from D-Mannitol, Cellobiose, Lactose and D-Xylose). The panel of bacteria chosen include organisms that are likely to be found in the natural flora of food and fecal specimens or have known or suggested physiologic or genetic relatedness to *E. coli* and *Shigella* species.

The nucleotide sequence of the present invention may be a non-ribosomal sequence of *E. coli*, *Shigella* species or a related species.

The DNA probes are $^{32}$P-labeled by random prime method (Amersham Pharmacia Biotech Inc, USA ) as per supplier's instruction but with modifications. The probe specificity is refined carefully by controlling the hybridization condition and the post hybridization wash condition. It will be noticed herein, that for optimal specificity, the post hybridization salt wash condition ranges between 5×SSC and 0.1×SSC for the various probes. Unless specified, the wash temperature for the membranes is at 65° C.

Probe A is made up of a combination of fragments (1,2,3 and 4 of FIG. 1, a–c) and covers a large part of the Formula I sequence. It will be noticed that probe A and some of the gene probes within Formula I (Table 2a, FIGS. 2–19) are specific for the *E. coli* species and some *Shigella* species, implying that there are highly conserved and specific regions among *E. coli* species and *Shigella* species. For example, within the Escherichieae family, gene probes defined by primers pairs ECM-1163, ECM-1958 (FIG. 4) and tor D-10574, tor D-11160 (FIG. 7) detect *E. coli* and *Shigella* species but not non-coli *Escherichia* species such as *E. vulneris* (ATCC 33821), *E. hermannii* (ATCC 33650) and *E. blattae* (ATCC 29907). Gene probes defined by primer pairs 81B-7223, 81B-7794 (FIG. 12) and 81B-7278, 81B-7754 (FIG. 13) detect the presence of *E. coli, Shigella flexneri* and *sonnei*, except *Shigella boydii*. Gene probe defined by putP-5944 and putP-6693 (FIG. 19) detects *E. coli, Shigella boydii* and *Shigella sonnei* and other enterobacteria (showing variable homology) but does not detect *Shigella flexneri*. Probe A detect *E. coli* and *Shigella* species only (FIG. 2). This invention also indicates that when a large gene probe is reduced to many smaller gene probes, the specificity of the smaller probes can be different from the parent probe and therefore must be tested out before use.

The method of the present invention encompasses the use of probes of any length however it is envisages that the *E. coli-* and/or *Shigella* species'-specific nucleotide sequences comprise at least 8 nucleotides in length.

A further aspect of the present invention provides a molecular probe comprising at least 8 nucleotides obtainable from the nucleotide sequences of Formula I wherein said molecular probe is capable of specifically hybridizing to *E. coli-* and/or *Shigella* species'-derived nucleic acid molecules.

Still even yet more especially the present invention provides a method for testing and selecting other sequences in *E. coli, Shigella* species or related microorganisms in a sample, said method comprising subjecting a nucleic acid molecule preparation from said sample to genetic analysis using one or more *E. coli* or *Shigella* species'-specific nucleotide sequences obtainable from one or more nucleotide sequences of Formula 1 and/or Table 1 wherein the ability for said *E. coli-* or *Shigella* species'-specific nucleotide sequences to hybridize to complementary nucleotide sequences in the nucleic acid preparation is indicative of an *E. coli* or *Shigella* species'-specific nucleotide sequence.

Some of the advantages of a smaller size probe are the ease with which they can be amplified by PCR to generate more material to work with and to carry out PCRISH.

The specificity of a smaller gene probe may be greater, equivalent or less. *E. coli* gene sequence at 7562 to 7794, AE000202 has relatively similar specificity as probe A (FIGS. 21, 20) to *Enterobacter cloacae* but has the added advantage of not having homology to *Shigella boydii* (FIGS. 15, 2). A dilution assay indicates that *Enterobacter cloacae* DNA has 50 times less hybridization signal intensity to both probe A and *E. coli* gene probe sequence (nt 7562 to 7794 of AE000202) as compared to *E. coli* DNA. Post hybridization wash condition is at 1×SSC, 0.1% w/v SDS, 20 mM Na pyrophosphate at 65° C. Other examples such as those shown in FIGS. 3,4 and 7 indicate higher specificity than probe A. An example of a more specific gene probe that recognizes *E. coli* and *Shigella* is that defined by primer sequence torD-10574 and torD-11160. Although the wash condition for FIG. 7 is at 0.1×SSC, 0.1% SDS, 20 mM pyrophosphate at 65° C., the probe is equally specific at 1×SSC wash (data not included). The wash at 0.1×SSC indicates the hybrids are relatively stable and specific.

DNA Probe Test, Selective Agar Media and Biochemical Test

The invention herein describes the specificity of the gene probe at nt 7223 to 7794, AE000202 (FIG. 12), herein called 81B, as an example, in identifying *E. coli*. This probe give 10 times less intense signal with *Enterobacter cloacae* DNA at the selected hybridization (see assay section: hybridization and post hybridization conditions) and post hybridization wash (1×SSC at 65° C.) condition (FIG. 22). Despite this cross over in hybridization signal with *Enterobacter cloacae*, the primer sequence and gene probe sequence is relatively conserved. This molecular DNA test is compared to the selective isolation media and biochemical test. This comparative study is carried out on ATCC strains of *E. coli* and fecal isolates of subjects. The fecal isolates that are either positive or negative for this gene probe are isolated and tested on eosin methylene blue (EMB) lactose-sucrose agar (bioMerieux, France), MacConkey agar (Oxoid, USA) and MUG agar (Oxoid, USA), API (bioMerieux, France) and sugar test.

All 66 (100% sensitive) randomly selected colony purified fecal bacteria isolates that are positive for the probe 81B are identified to be *E. coli* with the API test strip and additional sugar test (4/66).

All 89 (100% specificity) randomly selected colony purified fecal bacteria isolates that are negative for the probe 81B are identified to be either gram negative or gram positive microorganism but not *E. coli* or *Shigella* species.

Of the patients' *E. coli*, 27 of 38 (71%) *E. coli* tested are EMB positive, 56/66 (85%) of *E. coli* are tested positive on MacConkey and MUG agar plates alone. *E. coli* that is MacConkey positive need not be MUG positive and vice versa. The *E. coli* identified by the probe 81B included lactose-negative *E. coli* which cannot be identified using the MPN method alone, or the MacConkey media alone or the MUG media alone. The probe detects the enteropathogenic serotype 0157:H7 and the 029:NM *E. coli* that will not be picked up by the MUG assay. The selective agar plates and biochemical test are purchased in dried form and reconstituted according to supplier's instruction.

The 81B probe will recognize *E. coli* strains even those possessing haemolytic properties, as observed on blood agar, and possessing DNA sequences that encodes known toxigenic genes, invasive genes, adherent genes and cytonecrotizing genes.

One particularly preferred aspect of the present invention discloses a method for detecting the presence of *E. coli* or *Shigella* species or related microorganisms in a sample as hereinbefore described wherein hybridization of *E. coli-* and/or *Shigella* species'-specific nucleotide sequences to the nucleic acid preparation is detected by the presence of amplified nucleic acid products.

A further related aspect of the present invention provides a method for detecting the presence of *E. coli, Shigella* species or related microorganisms in a sample wherein hybridization of *E. coli-* and/or *Shigella* species'-specific nucleotide sequences to the nucleic acid preparation or the presence of amplified nucleic acid products is detected by a reporter molecule giving an identifiable signal.

Tissue Infection

Several techniques employing molecular hybridization for diagnosis of bacteria infection can be used. They include southern filter or dot-blot hybridization on DNA extracted from tissues. They may be useful but they are unable to tell the investigator where precisely the infection is and if it is specific to certain cell type within a tissue. The DNA molecular probes we have identified in this invention can be used for those assays which follows the aforementioned approach as an early investigation tool. However, the use of primer sequences and DNA gene probes can be made more informative in the technique of polymerase-chain-reaction-in-situ-hybridization (PCRISH). This technique can help in locating the presence of the microorganism, bearing in mind that presence of specific antigen within a test sample, may not necessarily imply that the identified pathogen is viable or necessarily causative of the clinical infectious disease at that tissue site. The causative agent at the site of mucosal disease if isolated, identified and shown to have properties that can account for the diseased state, will provide additional evidence of its role for the disease condition.

The invention herein will describe the utility of the new probes to show the association of bacteria DNA presence with histopathology of tissue samples.

Presence of Bacteria in Tissue as Detected by PCR of Tissue Total Genomic DNA

The invention herein used PCR technique in amplifying the gene sequence 81B (primers: 81B-7223, 81B-7794) to test for its presence in total DNA extracted from colon tissue (total of 1 µg per 100 µl PCR reaction mix). Five microlitres of the PCR product mixture is resolved on ethidium bromide stained agarose that has a molecular weight marker on one of the tracks. A PCR product migrating at the expected position and is hybridization positive for the $^{32}$P labeled DNA probe (probe sequence correspond to nucleotide (nt) 7278 to 7773 of AE000202) is taken as positive. The inventors found the presence of the sequence as visualized under 312 nm ultra-violet (uv) illumination, in all cancer patients studied, either in tumour tissues (25/29, 86%) or in adjacent normal tissues (17/23, 74%). In contrast, in 34 control patients with no cancer, but is admitted for some related gastrointestinal complaints, this sequence is found in 7/34 (21%). The P value is <0.001.

It is emphasized that confirmation of target PCR product can be carried out by hybridization of the Southern transferred membrane bound PCR products to specific radiolabeled gene probes.

This data suggests that colon tissue from patients with colon cancer harbor more bacteria than patients with no colon cancer. Such data are informative when correlated with histology, clinical diagnosis and pathogenic bacteria isolates from tissue samples devoid of contaminants.

Accordingly, yet a further related aspect of the present invention provides a method for detecting the presence of *E. coli, Shigella* species or related microorganisms in a sample wherein the sample comprises food, water, semi-solids or semi-liquid material, mammalian tissue, tissue extract or cells of tissue or normal tissue or tissue predisposed to cancer growth or malignancy or cellular instability.

In a particularly preferred aspect of the present the mammalian tissue is associated with colon, stomach or colorectal tissue.

A related aspect of the present invention provides a method for identifying nucleotide sequences, or their expressed products, capable of inducing or otherwise facilitating abnormal cell growth or abnormal physiology, said method comprising introducing a nucleotide sequence comprising *E. coli*- and/or *Shigella* species'-specific nucleotide sequences from the nucleotide sequences in Formula I into cells and observing morphological and/or physiological changes to said cells compared to control cells without said introduced nucleotide sequences wherein the presence of abnormal morphology and/or physiology in a cell is indicative of a nucleotide sequence from Formula I, or a polypeptide expressed therefrom, which is capable of inducing or facilitating abnormal cell growth or physiology.

In a further preferred aspect of the instant invention the abnormal cell growth or physiology is associated with cancer or a predisposition to the development of cancer or cellular instability.

The genes encoded within Formula I can be transcribed into mRNA and translated into functional proteins. These can serve as targets for detection and intervention. The detection systems that can be used include imaging, scintigraphy, immunohistological methods, enzyme-chemical/amplification detection methods, chemical methods and microchip computer assisted methods (direct/indirect). These can be carried out on patients or animals or on samples such as serum, tissues, food and liquids.

The invention can be used in the following areas:
(1) Molecular diagnosis—for example, testing patients, e.g. predisposed to cancer, cancer, having infection, for the presence of Formula I and/or its transcripts;
(2) Serological diagnosis—for example, testing patients predisposed to cancer, cancer having infection, for the presence of the protein encoded by the Formula I sequence, or that specifically binds to such a polynucleotide, or testing such patients for the presence of antibodies to such protein. A sample from the patient is preferably blood, urine or other body fluids, tissue or excretion products;
(3) Immunohistochemistry/histochemistry applications—for the diagnosis of predisposition to cancer, cancer, cellular instability, infection in tissue samples;
(4) Diagnostic imaging—in which case the antibody or probe will have an appropriate label or marker, for example, a radioactive label or marker;
(5) Therapy
   (a) for example, antibodies of the present invention may form part of an immunotoxin, in order to deliver toxic agents, such as plant toxins, e.g. ricin, to the site of a malignant or even a benign tumour (see, for example, European Patent Application No. 84304801.8—Publication No. 0145111);
   (b) for example, polynucleotides of the present invention may be useful alone in therapy as anti-sense DNA or RNA. Thus, polynucleotides of the present invention optionally in a vector or in a polynucleotide analogue, which contains sequences complementary to DNA or RNA defining a protein which is differentially expressed during cancer initiation, progression and metastasis or a portion thereof can be employed to prevent expression of the said protein;
   (c) for example, the metabolic pathway that the Formula I sequence or its nearby sequence encode can be utilized to activate pro-drugs;
(6) Histological analysis—DNA or RNA or protein having an appropriate label or marker may be useful for in-situ detection for histological analysis; and
(7) Food and water sanitation.

Polymerase-Chain-Reaction-In-Situ-Hybridization Technology (PCRISH).

In this invention herein, we will describe the new use for DNA probes that permit the detection and localization of members of Escherichieae family (and *Shigella* species) in paraffin embedded tissue samples by polymerase-chain-reaction-in-situ-hybridization (PCRISH). This is useful for the study of (1) clinical conditions with bacteria infection (2) treatment and infection (3) association of bacteria in the development of cancer and (4) identifying cells at risk of or having genome that is genetically unstable.

These investigations can be carried out on routinely processed, formalin-fixed and paraffin-embedded tissues obtained from pathology files at any hospital. Such tissues have excellent preservation of tissue architecture and cellular detail and allow retrospective analysis of stored tissue blocks. To illustrate the utility of the above-mentioned probe, we will provide data on its use in the study of colon and gastric related conditions.

Sensitivity and Specificity

This invention herein will provide data on how sensitivity and specificity of an assay can be dramatically improved by carrying out a hybridization step after PCR. The inventors will describe an assay that will simulate PCRISH in-vitro. First, PCR is carried out on randomly selected *E. coli* (number, N=3), *Shigella sonnei* (N=1), Enterobacter agglomerans (N=1), *Pseudomonas aeruginosa* (N=1), *H. pylori* (N=1) from patients, TG2, K12 and the panel of ATCC bacteria total genomic DNA (Table 3). A given volume of the PCR product mixture is then resolved on an agarose gel, and the PCR products visualized by ethidium bromide staining under UV illumination. The primer targeted bacteria sequence will give a single band. Many additional bands indicates the lack of specificity of the primer sequences. The products in the gel are subsequently transferred onto nylon-plus membrane (Amersham Pharmacia Biotech Inc, USA) by the method of Southern, and hybridized to $^{32}$P random-prime labeled sequence specific probes. This hybridization step increases the detection level and also improves the specificity of the assay by hybridizing specifically to homologous sequences. Specificity is denoted by a single band when exposed to an autoradiograph. Such assays indicate whether the primers and probes are specific and can help to detect the presence of bacteria when used in PCR-ISH. The selection of primer and probe sequence within the Formula 1 can be empirically carried out in a step-wise systematic fashion until all the appropriate ones are selected.

Gene sequences between nt 7419 and 7985 (AE000202), herein called the OH, the 81B (nt 7223 to 7794, AE000202) and the *H. pylori* ribosomal gene (Table 3) have been tested in accordance with the present invention. By varying the PCR conditions, OH-7419 and OH-7985 primers directed PCR amplification of bacteria DNA could give rise to specific and non-specific products. Any DNA sample giving rise to PCR amplified band, whether or not in the presence of non-specific bands, and migrating in agarose gel at the expected molecular weight is denoted as positive (Table 3). Hybridization of labeled gene probe defined by the sequence between primers OH-7562 and 81B-7794 specifically picks up PCR products from *E. coli* and *Shigella* species except *Shigella boydii*. Primers 81B-7223 and 81B-7794 are more specific under the PCR conditions used and give specific bands of expected molecular weight. The labeled gene probe having the sequence between nt 7278 and 7773 specifically hybridizes to the products from *E. coli* and *Shigella* species except *Shigella boydii*. The specificity of this latter gene probe for genomic DNA of *E. coli* species is shown in FIG. 23. Although there is low homology between *Enterobacter cloacae* DNA and OH gene probes (low, FIGS. 14,15,21) and 81B gene probes (relatively higher than OH, FIGS. 12,13,22), the aforementioned OH and 81B PCR primer pairs do not amplify specific products from *Enterobacter cloacae* DNA.

The dramatic increase in sensitivity and specificity is illustrated by the *H. pylori* ribosomal gene primers and gene probe. FIGS. 24 and 25 shows that the *H. pylori* probe has a low to moderate level of homology to enterobacteria and gram positive bacteria DNA even with stringent post hybridization wash condition of 0.1×SSC, 0.1% SDS, 20 mM pyrophosphate at 65° C. However, upon PCR and hybridization to DNA of a selected number of enterobacteria and gram positive bacteria (Table 2a, grid D) likely to be found in the gastrointestinal tract, only *H. pylori* Presence is detected (Table 3). FIG. 26 and Table 2a, grid F will show the dot-blot hybridization result where the detection limits for the presence of *H. pylori* DNA is dramatically improved after a simulated PCRISH technique. Two hundred nanogram each of total genomic HP DNA and different purified fecal isolates of *E. coli* genomic DNA from different patients, are each PCR amplified in 100 μl of reaction mixture. After PCR, 10 μl is taken out from the *H. pylori* reaction tube and diluted with 90 μl of water before a known volume is being dot-blotted onto Amersham nylon plus membranes and hybridized to random primed $^{32}$P labeled *H. pylori* (HP) ribosomal probe.

FIG. 26, column A, rows 1 to 4 each contained 1, 5, 10 and 50 μl of the 10 fold diluted *H. pylori* post PCR reaction mixture. The hybridization signals intensified with increase in amount of PCR products. Rows 5 to 8 contained 1, 5, 10 and 50 μl of 10 fold diluted PCR product comprising of equal portions of 4 *E. coli* DNA PCR products (K12, 142/31, 179/36, 197/5 and 117/3B). No amplified PCR products are obtained with *H. pylori* primer directed amplification of *E. coli* DNA. This column shows that the *H. pylori* primers are specific for the *H. pylori* genome.

FIG. 26, column B, rows 1 to 5 contained mixture of 5 μl diluted post *H. pylori* PCR reaction mixture and 5 μl (undiluted) of post PCR reaction mixture of different *E. coli* DNA isolates respectively. The result indicates that the hybridization of HP probe to the *H. pylori* PCR products is not affected by the presence of *E. coli* DNA. This is indicated by the equal intensity of the dot.

FIG. 26, column C, rows 1 to 5, each contained 5 μl (undiluted) post PCR reaction mixture of different *E. coli* isolates of different patients. The HP primers did not PCR amplify *E. coli* DNA.

FIG. 26, rows 6 to 8 of column B, each contained 10 ng, 50 ng and 200 ng respectively of *H. pylori* genomic DNA and in column C, each contained instead a respective equivalent of *E. coli* genomic DNA. The HP probe showed higher homology to its own gene.

Hybridization of a panel of bacterial DNA to the HP gene probe has shown that it has some homology to the other bacteria species (FIGS. 24, 25). However by combining sequence specific primer directed PCR and hybridization with a probe that has low homology to other species, it is still possible to increase the sensitivity and specificity of HP detection (FIG. 26, Table 2a- grid F).

Exemplification of various aspects of the invention using PCRISH in no way limits the methods of the present invention and any appropriate technique may be used to monitor or detect the presence of *E. coli* DNA in cells. This invention herein relates the use of PCRISH as a method for illustrating how pathogens can be detected in-situ. It does not exclude the use of in-situ hybridization nor in-situ-PCR technology, using sequences within Formula I, as an alternative. The amount of target, reporter system, PCR cycles and hybridization conditions are important determinants in deciding which method is appropriate.

Bacteria Detection in Tissue Specimens Using PCRISH Technology

A preferred method in amplifying vast amount of DNA sequences in cells/tissue and detecting the presence of the sequences in-situ use the PCR-in-situ hybridization (PCR-ISH) technology. PCRISH is practiced routinely by those having ordinary skill in the art and its uses in detecting infection in-situ is widely used and accepted.

As a start, cells or tissues are fixed with a suitable fixative (example 10% buffered formalin) for 2–72 hrs and the tissues subsequently paraffin-embedded. The paraffin-embedded tissues are then sectioned at 3–4 microns and mounted on aminoalkysilane treated glass slides. Before amplification is undertaken, the sections are deparaffinized first and then carefully permeabilized using proteolytic enzymes such as proteinase K, so that the cellular morphology is maintained and the DNA is accessible. The cell/tissue is now ready to permit access of PCR reagents into the cellular compartment where the nucleic acids are found. Amplification then occurs at the defined target intracellular sequence. Detection of amplified product is then carried out by hybridizing with a non-radioactive labeled DNA probe. We used DNA probes labeled with Digoxigenin-labeled nucleotides. This DIG-labeled probe is detected with anti-digoxigenin (anti-DIG) antibodies that are conjugated to alkaline phosphatase. This alkaline phosphatase is visualized with colorimetric (NBT and BCIP) alkaline phosphatase substrates (Boehringer Mannheim). It is imperative to always to perform a negative control with each specimen and to understand that a negative result only indicates an inability to detect the substance analyzed. Negative tissue control does not contain the specific antigen in question. Positive control must accompany each run of test tissue sections within which the specific DNA sequence is sought.

Interpretation of Hybridized Tissue Sections.

It is known that some members of the Escherichieae family (*E. coli* and *Shigella* species) are able to adhere to, invade cells and move across cells. Therefore, there is the need to correlate histopathology with quantity and depth of bacteria presence in order to evaluate their role in gastrointestinal infection and cancer. This is done by studying the quantity and spatial distribution within the tissues of the hybridization signals generated with the DIG-labeled bacteria DNA probes.

We have categorically defined the spatial distribution of the bacterial presence into positive and negative depending on whether the signals are found (i) outside mucosa cells/lumina propria (negative), (ii) in mucosa cells (positive) and (iii) in nuclei of mucosa cells (positive). All tissues are obtained upon discovery (pre-treatment) unless stated otherwise.

Colon

The use of primer and probe DNA gene sequence of 81B for carrying out PCRISH in colonic mucosa tissue in this invention is characteristically found to identify all hyperplastic tissues (number [N]=7; FIG. 27), adenomas (N=12; FIG. 28), adenocarcinomas (N=11; FIG. 29) and metastatic colonic cells in liver specimens (N=5; FIG. 30) to be positive for the 81B marker probe. The signals are characteristically predominant in cells and in nuclei of the cells. The hyperplastic tissues, adenomas and adenocarcinomas can also have 81B signals located outside cells. Metastatic cells, with primary in the colon, found in liver specimens show distinct 81B signals in the nucleus and without significant exogenous 81B signals outside cells. Mucosa tissues of normal histology obtained adjacent to tumours (N=8; FIG. 31) are positive in certain areas and have intense signals in those areas. The majority of tissues without cancer (N=16 ; FIG. 32) and obtained from normal patients indicated for colonoscopy are negative (69%). One example of an infected tissue is that of a patient's colon tissue diagnosed to have proctitis on histology (FIG. 33). Here, the distribution of 81B signal is diffusely distributed but without the intense cellular/nuclear signal that is observed in normal tissue adjacent to tumours (FIG. 31) and in tumours (benign, pre-malignant and malignant).

*H. pylori* Probe is insignificant in metastatic cells in liver sections (N=5; FIG. 34) and serves as a negative control.

The transition from normal through pre-malignant to localized malignant and finally a metastatic stage has been histologically defined for colorectal cancer. Therefore the appearance of 81B signals at early stages and before histological changes, through to all histological changes associated with cancer and leading to the metastatic stage indicates a possible aetiological role for *E. coli/Shigella*. This invention herein identifies several uses for the *E. coli/Shigella* probe whereby markers specific for *E. coli/Shigella* can be used for screening patients for risk of colorectal cancer, colorectal cancer and infection with *E. coli/Shigella*.

Gastric

*Helicobacter pylori* is established as the major aetiological agent in gastritis and peptic ulcer and it is also known to infect half of the world's population. This high infection/disease ratio is however explained by host factors, socio-economic conditions of the various countries and infection by a sub-population of virulent *Helicobacter pylori* (Chu, K. M. and Branicki, F. J. *JAMA SEA* 13:5–7, 1997). Therefore, it is clear that to understand the pathogenesis of *Helicobacter pylori* and general infection, one approach is to precisely locate the bacteria to the site of mucosal disease and to correlate it to histology and clinical presentation. Past data using immunocytochemical detection system (Cartun et al. *J Clin Pathol*. 43:518. 1990) and in-situ hybridization technique have both localized the bacteria to the luminal, foveolar epithelium or periepithelial mucous layers of the gastric mucosa of helicobacter pylori associated gastritis (Van Den Berg et al. *J Clin Pathol*. 42:995–1000, 1989; Bashir et al. *J Clin Pathol* 47:862–866, 1994). Unlike these observations, we are able to show that *Helicobacter Pylori* can be found beyond the luminal or foveolar epithelium in patients with gastritis and may assist in understanding the significance of high infection/disease ratio. This invention will highlight the resolution power of a successful PCRISH technique for studying the association of endoscopic diagnosis of gastric conditions with histological findings, bacteria pathogenesis and clinical presentations.

The invention herein has found *E. coli*, other than *H. pylori*, in stomach related conditions such as gastritis of varying severity, ulcer and cancer.

The use of primer and probe DNA gene sequence of *H. pylori* and 81B for carrying out PCRISH in stomach tissue in this invention is found to identify all *H. pylori* Positive active chronic gastritis (N=9), *H. pylori* positive gastritis (acute on chronic) (N=12), active chronic gastritis with no histologically detectable *H. pylori* (N=10), chronic gastritis with no histologically detectable *H. pylori* (N=9), mild gastritis with no histologically detectable *H. pylori* (N=4), normal with no histologically detectable *H. pylori* (N=4), normal tissue distant to tumour (N=1), adenocarcinoma (N=5) and liver specimen with poorly differentiated metastatic stomach adenocarcinoma (N=1), positive for the 81B sequence. The distribution of the 81B sequence is such that they can be in the luminal areas with variable degree of penetration into intercellular, cellular and nuclear areas of specimens. The area of infection is patchy. For the cancer specimens, the signals are found mainly in the nuclei of tumours (FIG. 35) and in normal tissue adjacent to tumours (FIG. 36) they are found both in the nuclear and luminal area. For the metastatic cells in liver section, that originated from the cancer at the gastro-oesophageal junction, the signals are also mainly. in the nuclei but without the exogenous signals that can sometimes be observed with the primary tumour (FIG. 37). Gastric mucosa with normal histology and no histologically detectable *H. pylori* but positive for the 81B probe is interesting as the patient presented with non-ulcer dyspepsia, epigastric discomfort and vomiting. The 81B signals show patchy aggregates. FIGS. 38 and 39 are of the same specimen but showing different area The samples that are histologically diagnosed to be positive for *H. pylori* are confirmed by PCRISH. Although the *H. pylori* probe is found present in normal tissue distant to the adenocarcinoma of stomach (FIG. 40), it showed insignificant nuclear signals in the tumour itself (FIG. 41). *H. pylori* probe is not detected in metastatic tumour cells in liver (FIG. 42).

This invention herein presents a use for the *E. coli/Shigella* probes in gastric related studies whereby it can be used to screen for patients with risk of gastric cancer, gastric cancer and gastric infection. When found in the presence of *H. pylori*, it supports the possibility that synergistic interaction between two types of bacteria can be a cause for gastric related conditions (active chronic gastritis, FIGS. 43, 44). How important the presence of *H. pylori* is to *E. coli* is yet to be determined as it is known that *E. coli* has a mechanism for acid resistance. (Lin J, et al. *Applied and Environmental Microbiology* 62:3094–3100, 1996). In addition, *E. coli* are known to have invasive, cytonecrotizing, adherent, and toxigenic genes that can account for gastric related conditions.

Cellular Instability

Studies have suggested that apparently uninvolved mucosa adjacent to, and even remotely from colorectal cancer is abnormal morphologically and histochemically (Ngoi et al. Cancer 66:953–958, 1996). In addition, the invention herein showed *E. coli/Shigella* DNA marker in the nucleus of many normal cells next to tumours, tumour cells and metastatic tumour. This suggests that *E. coli/Shigella* probe can be a marker associated with risk of cellular instability or cellular instability and tumourigenesis as it is known that bacteria DNA has tumourigenic potential.

Isolation of Microorganism that is Associated with Tissue Infection

The invention herein indicates a method whereby in addition to localization of bacteria in tissue sample, the marker sequence can further assist in identifying and isolating members/strains of the family of bacteria it represents, in tissue/fecal specimens.

To start off at the tissue level, using PCRISH, the spatial distribution of the marker (for example, 81B or OH or any other that is within the Formula 1 sequence) would indicate whether there is a pathogen present. This observation may be supported by histological diagnosis for infection, benign, pre-malignant or malignant cancer. This is then followed by detecting for positive colonies isolated from the positive specimens (for example tissue, fecal), and hybridizing to the positive colonies, separately, a panel of DNA that is known to encode either invasive, adherent, necrotizing, toxigenic or other pathogenic properties. The bacteria that is found to possess pathogenic properties as defined by a DNA sequence, can have their presence within the tissue checked by PCRISH using primers and hybridizing probes for that property. From hereon, association studies can be carried out empirically with the various pathogenic probes to understand bacteria presence and infection, cancer risk and etiology of cancers.

With this approach, the inventors have found pathogenic *E. coli* to be the main pathogen associated with cancer risk and cancer. Herein the inventors define pathogenic *E. coli* as those strains of *E. coli* able to invade into cells and those that can cause cellular changes in cells. Since pathogenic *E. coli* is found in the instant invention as a marker of cellular instability and tissue at risk of cancer (benign tumours, pre-malignant tumours) and cancers (malignant tumour/cells), it therefore implies that any sequence of *E. coli* (pathogenic or otherwise) can be used for the above purpose.

A related aspect of the instant invention provides a molecular probe of at least 8 nucleotides, identified by the methods as herein described wherein said probe comprises a sequence of nucleotides from Formula I and wherein said molecular probe is capable of specifically hybridizing to *E. coli* and/or *Shigella* species'-derived nucleic acids.

Assays

Microbiological techniques are practiced routinely by those having ordinary skill in the art and its use is wide and accepted. Information for practicing is disclosed herein by reference: "Nga, B. H. and Lee, Y. K.: Microbiology Applications in Food Biotechnology. Elsevier Applied Science, 1990. Koneman et al. Introduction to Diagnostic Microbiology. J B Lippincott Company 1994. AOAC Official Methods of Analysis 1995. Pepper I L., Gerba C P and Brendecke J W: Environmental Microbiology: A laboratory Manual. Academic Press 1995. P R Hunter: Waterborne Disease: Epidemiology and Ecology. John Wiley and Sons 1997.

DNA and related technology is widely used by those having ordinary skill in the art and information for practicing DNA and related technology is disclosed herein by reference: Moseley et al. *The Journal of Infectious Diseases* 142:892–898, 1980. Berger S L and Kimmel A R: Guide to Molecular Cloning Techniques. Methods in Enzymology. Volume 152. Academic Press Inc 1987. Tenover F C: DNA Probes for Infectious Diseases. CRC Press 1989. Sambrook J, Fritsch E F and Maniatis. T: Molecular Cloning: A laboratory manual. Second Edition. Cold Spring Harbor Laboratory Press 1989 (3 volumes); Echeverria et al. *J Clinical Microbiol* 27: 31–334, 1989; Virginia L C and Bavoil P M: Bacteria Pathogenesis. Academic Press 1997.

Aspects of the present invention include various methods such as PCR and dot-blot, for example, for determining whether a sample contains bacteria sequence of the Escherichieae family by molecular analysis. Nucleic acid-based assays can be made exquisitely sensitive, and their specificity can be adjusted from broad to a very narrow range by careful design of the probe and precise control of hybridization conditions.

The invention relates to Formula I, DNA gene probes and primers used in the method of identifying DNA that is encoded in the DNA of members of the Escherichieae family such as the *E. coli* and *Shigella* species.

The DNA sequence based methods for determining whether a sample DNA encoding the sequence found in *E. coli* and *Shigella* species include but are not limited to polymerase chain reaction technology, Northern and Southern blot technology, dot-blot, colony-blot, PCR-in-situ hybridization, in-situ-hybridization technology and oligonucleotide hybridization technology.

The invention primarily involves methods in DNA detection and these methods are commonly used alone or in combination so as to enhance the sensitivity and specificity of the DNA sequence for detecting the presence of species of E. coli and Shigella.

It is contemplated that other sequence-based methodology for detecting the presence of bacteria DNA in samples may be employed according to the invention.

PCR Technology

A preferred method in amplifying vast amount of DNA sequences uses the polymerase chain reaction (PCR) technology. PCR technology is practiced routinely by those having ordinary skill in the art and its uses is wide and accepted. Methods for practicing PCR technology are disclosed in "McPherson M J, Quirke P and Taylor G R: PCR. A Practical Approach. Volume 1. Oxford University Press 1994", which is incorporated herein by reference.

The nucleotide sequence present in species of E. coli and Shigella is well known such as in GenBank database accession number AE000201, AE000202 and AE000203. To perform this method, DNA is extracted/released from cells in a sample and tested using well-known methods and readily available starting material.

The DNA is combined with the primers, free nucleotides and enzyme following published PCR protocols. The mixture undergoes a series of temperature changes. If the DNA encoding the marker sequence for E. coli and Shigella species are present, that is, if both primers hybridize to sequences on the same molecule, the molecule comprising the primers and the intervening complementary sequences will be exponentially amplified. The amplified DNA can be easily detected by a variety of well known means. If the sequence is not present, no DNA molecule will be exponentially amplified. The PCR technology therefore provides an extremely easy, straightforward and reliable method of detecting E. coli and Shigella species DNA in a sample. Publication is herein provided by reference for indicating how PCR technology is utilized for detecting pathogens in food, Gannon et al *Applied and Environmental Microbiology* 58:3809–3815, 1992; AOAC Official Methods of Analysis 1995.

PCR Primers

PCR primers can be designed routinely by those having ordinary skill in the art using well known DNA sequence information that can be retrieved from GenBank database. Software programs are also available to assist in designing optimal primer sequences as long as sequences of gene of interest are known. (PCR PLAN (PC/Gene system, Intelligenetics, inc. USA). Primers are generally 8–50 nucleotides, preferably 18–28 nucleotides. A pair of primers is routinely used for PCR. When performing PCR on extracted DNA samples containing targeted specific bacteria DNA, multiple copies of the DNA will be made. If the targeted DNA is not present, PCR will not generate a discrete detectable product.

PCR Product Detection

PCR amplified DNA may be detected by several well-known methods. The preferred method for detecting the presence of amplified DNA is to resolve the PCR reaction material by gel electrophoresis and staining the gel with ethidium bromide in order to see the amplified DNA if present. A standard molecular weight marker containing a standard of equivalent size to the expected size of the amplified DNA is preferably run on the gel as a control.

In some instances, such as when small amounts of amplified DNA is generated at the first attempt, therefrom, it is desirable or necessary to perform a nested PCR reaction on the first PCR reaction product. A nested set of primers is used in the second PCR reaction. The nested set of primers can either hybridize to sequences downstream of the 5'primer and upstream of the 3'primer used in the first reaction or hybridize further into the first PCR product and allow a second PCR reaction.

The present invention includes oligonucleotide sequences, which are useful as primers for performing PCR methods to amplify DNA fragments that are useful for identifying the Escherichieae family in particular E. coli and Shigella species. For the detection of the sequence, labeling of DNA can either be radioactive or non-radioactive nucleotides.

Random Prime Labeling of DNA Fragment (Megaprime DNA, Amershanm Pharmacia Biotech Inc, USA)

Labeling can be carried out according to manufacturer's recommendation. Between 100–500 ng of DNA fragment is heated for 5 min with optimized amount of hexamer primer-solution (7 µl) before cooling rapidly to room temperature. This is then mixed with reaction mixture containing 12 µl of labeling buffer, 5 µl enzyme (1U/µl), 5 µl of $^{32}$P (6,000 Ci/mmol) and water to 50 µl final reaction volume. Labeling is carried out at 37° C. for 3 hrs. Separation of unincorporated $^{32}$P from labeled sequence is carried out by spin column method (Biospin columns: Bio-Rad Laboratories, USA).

The amount of sequence to be labeled can vary over a wide range as other parameters can influence the outcome of the invention. Examples to consider: the efficiency of the labeling system employed as other systems of labeling are available (polymerase chain reaction [PCR] labeling and use of radioactive or non-radioactive nucleotides), the nature of the sequence, either as probe A or in combination with other sequences or sub-fragments of the Formula I sequence.

PCR on Total Genomic DNA.

One hundred microlitres of PCR reaction mixture containing 10 mM KCl, 10 mM(NH$_4$)$_2$SO$_4$, 20 mM Tris HCl (pH 8.0), 2 mM MgSO$_4$, 0.1% Triton X-100, 200 µM (each) of dNTPs, 0.4 µM (each) of two primers, 1.5 unit of Taq polymerase and 1 µg of total genomic DNA (e.g. extracted from colon tissue) is amplified in a thermal cycler (Perkin Elmer Cetus, model TC1). Amplification is carried out in 3 stages: (i) 94° C. for 3 min; (ii) 10 cycles of 30 s at 94° C., 30 s at 62° C., 1 min 30 s at 72° C., and then (iii) 35 cycles of 1 min at 92° C., 40 s at 58° C., 1 min 30 s at 72° C. with an auto extension of 5 s at 72° C. at the end of each cycle. Lastly, an extension time of 7 min at 72° C.

Hybridization and Post Hybridization Conditions

The complete/partial sequence of formula I either alone or as a mixture are radioactively labeled by random-prime method using $^{32}$P-dCTP (alpha-$^{32}$P-dCTP, 6,000 Ci/mmol, Amersham Pharmacia Biotech Inc, USA). Nylon membranes (Hybond-N+, Amersham Pharmacia Biotech) are pre-hybridized overnight at 65° C. in a buffer containing 5×SSC (1×SSC is 0.15 M sodium chloride, 0.015 M sodium citrate) 0.1% SDS, 5× Denhardt's solution (1× Denhardt's solution is 0.02% bovine serum albumin, 0.02% polyvinyl pyrolidine 360K MW and 0.02% ficoll 400K MW in water), 200 µg/ml sonicated denatured salmon sperm DNA (sssDNA). Hybridization is carried out at 40° C. for overnight in a buffer containing 5×SSC, 20 mM sodium phosphate, pH 7.0, 1×Denhardt's solution, 0.1% SDS, 200 µg/ml sssDNA, 25% deionized formamide and labelled probe. The probe used can be from 100 to 500 ng of labelled sequence. The membranes are washed at 65° C. in 5×SSC, 0.1% w/v SDS, 20 mM Na pyrophosphate for several washes and followed by another few washes at 65° C. with 1×SSC, 0.1% w/v SDS and 20 mM Na pyrophosphate. All washes ranged from 30 to 60 min or until the background signal is acceptably low. Autoradiographs are exposed overnight at −70° C.

Several parameters can be empirically adjusted to improve on the specificity of the hybridization assay. An increased in stringency of the assay can be achieved by increasing the percentage formamide used during hybridization and/or by decreasing the salt concentration of the post hybridization wash buffer. Use of alpha-$^{32}$P-dCTP, 3,000 Ci/mmol is possible as this will only affect the level of sensitivity of detection.

Polymerase-Chain-Reaction-In-Situ-Hybridization Technology

Incorporated herein are references that are useful for sample preparation and understanding the principals and application of PCRISH: "Rentrop et al. *Histochemical J* 18:271–276, 1986, Carson, F. L. Histotechnology. A Self-Instructional Text. American Society of Clinical Pathologists Press 1990; Mikel U V: Advanced Laboratory Methods in Histology and Pathology. Armed Forces Institute of Pathology 1994; Nuovo, G. J.: PCR In Situ Hybridization. Protocols and Applications. Raven Press, N.Y. 1994; Gu, J: In Situ Polymerase Chain Reaction and Related Technology. Eaton Publishing Co. USA 1995; Boehringer Mannheim Non-radioactive It Situ Hybridization Application Manual ($2^{nd}$ edition) Washington, D.C., 1996; O'Leary et al. *J Pathol.* 178:11–20, 1996.

Fixation and Tissue Preparation

Pathology departments routinely fix tissue that are targeted for embedding in paraffin wax and which are subsequently used for diagnosis of tissue pathology. For fixation, we used for our biopsy specimens, 10% buffered formalin for 48–72 hrs (100% formalin diluted in phosphate buffered saline [PBS] to a 10% v/v concentration). After paraffin embedding, specimens of 3–4 micron thickness are cut onto 3-aminopropyltriethoxysilane (silane) coated microscope slides. Requirement of tissue thickness is dependent on the overall size of the tissue to be tested. The inventors recommend 3 micron for biopsy specimen and 4 micron for larger specimens. Before the samples can be used for PCRISH, the sections are fixed on slides at 58° C. for 1 hr 20 min, followed by deparaffinization in xylene (3×5 min) and final rinse in 100% (3×1 min) ethanol. At this stage, the sections can be left for use the following day. Just prior to use, the sections are rehydrated 2 min each through graded (70% and 50%) ethanol and water with final equilibration in PBS for 5 min.

PCR Labeling

PCR labeling of probes for PCRISH is carried out using digoxigenin dUTP (Boehringer Mannheim). This is carried out in a 100 µl reaction mixture comprising of 10 mM KCl, 10 mM $(NH_4)_2SO_4$, 20 mM Tris HCl (pH 8.0). 2 mM MgSO4, 0.1% Trition X-100, 50 µM DIG-11-dUTP, 150 µM dTTP, 200 µM each of dATP, dCTP, dGTP, 0.4 µM primers each, 2 units of Taq DNA polymerase (Perkin Elmer, UK) and 2 µl of first PCR product. The first PCR product is made with the outer primers for the same gene using K12 bacteria genomic DNA.

Amplification is carried out in 4 stages in a thermal cycle (GeneAmp PCR System 2400 or 9600, Perkin Elmer, UK):
(i) 94° C. for 2 min, (ii) 5 cycles of 30 s at 94° C., 30s at 58° C., 90s at 72° C. (iii) 10 cycles of 30 s at 94° C., 30s at 55° C., 90 s at 72° C. and (iv) 30 cycles of 60 s at 92° C., 30 s at 52° C. 90 s at 72° C., with an autoextension of 5 sec at 72° C. at the end of each cycle. Final extension time is 7 min at 72° C.

Proteinase K Digestion

For optimal cell permeabilization, each tissue type is empirically titrated against time at 40° C. for any given concentration of proteinase K. The inventors routinely use a fixed concentration of 10 µg/ml of proteinase K in PBS and adjust the time of digestion. The enzyme is diluted from a 10 mg/ml stock into the 40° C. pre-warmed PBS solution for 15 min before starting the permeabilization step. The size, type of tissue (normal or fibrous and necrotic) and how long it has been archived affect the duration of proteinase K digestion. After digestion, the sections are rinsed several times in PBS for a total of 5 min to stop the proteinase K digestion. This is followed by incubating in 10% buffered formalin for 1 min at room temperature and a further rinse in several changes of PBS to remove excess formalin. The sections are then dehydrated by incubating them, for 3 mins each, in a graded ethanol series of 70%, 85% and 100%. The slides are air dried at room temperature and free of ethanol before PCR.

In-Situ PCR

Twenty five microlitres of PCR reaction mixture containing 10 mM KCl, 10 mM $(NH_4)_2SO_4$, 20 mM Tris HCl (pH 8.0), 2 mM $MgSO_4$, 0.1% Triton X-100, 200 µM (each) of dNTPs, 0.6 µM (each) of two primers, 1 unit of Taq polymerase is overlayed onto each tissue section. Glass coverslip (24×40 mm) are then carefully put on top, taking care not to create air bubbles. The cover slips are sealed on all sides with nail vanish, then air dried before placing the slides into the thermal cycler (GeneAmp In situ PCR System 1000, Perkin Elmer Cetus). Amplification is carried out in 3 stages: (i) 94° C. for 2 min; (ii) 10 cycles of 30 sec at 94° C., 30 sec at 58° C., 60 sec at 72° C., and then (iii) 15 cycles of 30 sec at 92° C., 30 sec at 55° C., 60 sec at 72° C. with an auto extension of 5 sec at 72° C. at the end of each cycle. Lastly, an extension time of 7 mins at 72° C.

Post PCR Wash

After PCR, a check for air bubbles inside the cover-slip is always made, and its location and size is recorded before incubating them 5 min each at 92% and 100% ethanol respectively. The validity/interpretation of the final data will take into account the presence or absence, size and location of the bubble. Bubbles create artifacts. The layer of varnish is carefully peeled off the coverslip and the sections rinsed several times with 2×SSC before soaking twice in 0.5×SSC at room temperature for 5 min each. It is important that the varnish does not touch the specimen. The section is then treated with 10 µg/ml proteinase K solution for approximately 15 s before rinsing several times with PBS and dehydrated through a graded ethanol series (1 minutes each in 70%, 85% and 100% ethanol). The slides are air dried at room temperature before hybridization.

Hybridization

Twenty five microlitre of hybridization buffer (comprising of 25% formamide, 1×dendhardt solution, 5% (w/v) dextran sulphate, 200 µg/ml SSS DNA, 4×SSC and 5% (v/v) DNA probe) is overlaid onto the tissue section. Coverslip is placed over each tissue section, taking care not to create air bubbles.

Coverslip must be larger that the specimen, with a minimum distance of 3 mm away from all sides of the tissue. The coverslip is sealed on all sides with rubber cement and the cement is thoroughly air dried before the denaturation step. The sections are placed over a 95° C. heating block for 6 min to denature the DNA, rapidly cooled on ice for 1 min and finally incubated overnight at 40° C. in a humid chamber.

Post Hybridization Wash

After the overnight incubation, the rubber cement is carefully peeled off and the section rinsed several times in 0.5×SSC, twice for 5 min in 0.5×SSC at room temperature, and in 0.1×SSC at 42° C. for 20 min (2×5 min, followed by 1×10 min).

Immunological Detection Kit (Boehringer Mannheim)

This protocol follows closely the one provided by the manufacturer, but with minor modification. Each section is dipped briefly into buffer 1 (100 mM maleic acid, 150 mM NaCl, adjusted to pH 7.5 [20° C.] with NaOH, autoclaved) for equilibration and the excess liquid drained off before addition of 100 μl of buffer 2 (1% blocking reagent) is added to cover each tissue section. This is incubated in a humid chamber at room temperature for 20 min. This is followed by incubation with 100 μl of anti-DIG antibodies conjugated to alkaline phosphatase (1:500 v/v in 1% blocking reagent. Blocking reagent: a 100 mg/ml stock is prepared by dissolving the supplied powder form in buffer 1. This is then autoclaved and aliquoted into eppendorf tubes and frozen at −20° C. This stock is diluted 1:10 in buffer 1 to make the 1% blocking reagent.) A coverslip is put over the section to prevent evaporation and to ensure that the tissue section is completely covered with the antibody conjugate. This is placed in a humid chamber for 1 hr at room temperature. Sections are then incubated in buffer 1 for 20 min (2×5 min and 1×10 min) to wash off the unbound antibodies and equilibrated for another 5 min in 37° C. buffer 3 (100 mM Tris HCl, 100 mM NaCl, 50 mM MgCl$_2$, adjusted to pH 9.5 [20° C.] with NaOH). The colour-substrate stock solution (nitroblue tetrazolium salt/5-bromo-4-chloro-3-indolyl phosphate [NBT/BCIP]) is diluted 1:50 in 37° C. buffer 3 just prior to use. Detection buffer 3 is drained off sections and 120 μl of the freshly prepared colour-substrate solution is distributed over the tissue to detect the hybridized probe. The sections are covered with coverslip each and left in a 37° C. dark, humid chamber for at least 1 hour. Color development is carefully monitored until the reaction on the positive control slide is appropriate. Color development can range between 1 to 4 hours. After rinsing sections several times in 37° C. distilled water, they are stained with nuclear fast red for 1 to 5 s depending on the tissue size. Excess stain is rinsed off by several dips into distilled water and sections are mounted in a water-based mounting medium (DPX Mountant, BDH).

The system has been tested out on cytospin cells, colon, stomach sections that undergo PCRISH to (1) a reaction mixture without a probe and (2) a reaction mixture with a probe that has no complementary sequences in the tissue. There is no endogenous activity to give artifacts.

TABLE 1

| Primer Code | Map | Map Position | Sequence 5'–3' | Gene |
|---|---|---|---|---|
| ECM-246 | AE000201 | 246-266 | atgactggtttagtaaaatgg (SEQ ID NO. 1) | cspG |
| ECM-850 | AE000201 | 850-830 | tcaatattcactgttaacctc (SEQ ID NO. 2) | sfa |
| ECM-1163 | AE000201 | 1143-1163 | cattgcgtaaccaatcaccgc (SEQ ID NO. 3) | yccM |
| ECM-1958 | AE000201 | 1958-1938 | gcaagtagcacgacatttgtc (SEQ ID NO. 4) | yccM |
| torT-5129 | AE000201 | 5129-5148 | ggtgcaagcctctacgccgc (SEQ ID NO. 5) | torT |
| torT-5750 | AE000201 | 5750-5731 | tgccgcctctgccgcaatgg (SEQ ID NO. 6) | torT |
| torC-7218 | AE000201 | 7218-7242 | aacttgccgagcgtgaatgggcgcg (SEQ ID NO. 7) | torC |
| torC-7761 | AE000201 | 7761-7737 | gtggcctgcaacttgctccactcgg (SEQ ID NO. 8) | torC |
| torA-8332 | AE000201 | 8332-8356 | tatccgatggtacgcgtggactggc (SEQ ID NO. 9) | torA |
| torA-8891 | AE000201 | 8891-8867 | gcaatgtgcttcacatgctcgcgcc (SEQ ID NO. 10) | torA |
| torD-10574 | AE000201 | 10574-10593 | gaccacgctgacagcacaac (SEQ ID NO. 11) | torD |
| torD-11160 | AE000201 | 11160-11141 | ggtggtcgcactccactaac (SEQ ID NO. 12) | torD |
| CD-415 | AE000202 | 415-436 | gctttcccccaatctttacgtg (SEQ ID NO. 13) | cbpA |
| CD-1351 | AE000202 | 1351-1329 | gatttacgcgagataacgctatg (SEQ ID NO. 14) | cbpA |
| agp-3151 | AE000202 | 3151-3172 | cgctaatcgccgcagctgtggc (SEQ ID NO. 15) | agp |
| agp-4359 | AE000202 | 4359-4336 | cgctatcaaacttatccatcgggc (SEQ ID NO. 16) | agp |
| Wrb-4807 | AE000202 | 4807-4836 | tgtgaaacgtcaaataattcctgcgctgcg (SEQ ID NO. 17) | wrbA |
| Wrb-5235 | AE000202 | 5235-5206 | catgtacggacatattgaaacgatggcacg (SEQ ID NO. 18) | wrbA |
| ycdG-6073 | AE000202 | 6073-6094 | ctcctgatgaacaacttctggc (SEQ ID NO. 19) | ycdG |
| 81B-7223 | AE000202 | 7223-7240 | ggatccagccccatcaga (SEQ ID NO. 20) | ycdG |

TABLE 1-continued

| Primer Code | Map | Map Position | Sequence 5'–3' | Gene |
|---|---|---|---|---|
| 81B-7278 | AE000202 | 7278-7297 | cgtgttgaacgcccattact (SEQ ID NO. 21) | ycdG |
| ycdG-7359 | AE000202 | 7359-7340 | tcgacctctacagagagcgg (SEQ ID NO. 22) | ycdG |
| OH-7419 | AE000202 | 7419-7436 | acaagcagggcgcatcag (SEQ ID NO. 23) | b1007 |
| OH-7562 | AE000202 | 7562-7590 | acgaaaccagagcctcttccagttgcggg (SEQ ID NO. 24) | b1007 |
| 81B-7754 | AE000202 | 7773-7754 | gcccacattactggtgtgcc (SEQ ID NO. 25) | b1007 |
| 81B-7794 | AE000202 | 7794-7774 | ctgcagtgtgaccgatacgcc (SEQ ID NO. 26) | b1007 |
| OH-7985 | AE000202 | 7985-7966 | atagcagcaagctttatgcg (SEQ ID NO. 27) | b1008 |
| New1-8160 | AE000202 | 8160-8179 | cggcaagttgtgggctggag (SEQ ID NO. 28) | b1008 |
| New1-9704 | AE000202 | 9704-9684 | cgtaattattcccgctggcag (SEQ ID NO. 29) | b1010 |
| New2-9731 | AE000202 | 9731-9749 | gcgatatgagcaaaggacg (SEQ ID NO. 30) | b1011 |
| B-11375 | AE000202 | 11375-11356 | ctgtcgatgatcaaactgcg (SEQ ID NO. 31) | b1012 |
| New2-503 | AE000203 | 503-484 | gcatctccatacagaacagg (SEQ ID NO. 32) | ycdc |
| putP-5944 | AE000203 | 5944-5963 | ctgggttacttcgggcagcc (SEQ ID NO. 33) | putP |
| putP-6693 | AE000203 | 6693-6674 | cggagccgaatgatagtgcg (SEQ ID NO. 34) | putP |
| HP-178 | E25742 | 178-199 | gctaagagatcagcctatgtcc (SEQ ID NO. 35) | HP16S rRNA |
| HP-228 | E25742 | 228-252 | accaaggctatgacgggtatccggc (SEQ ID NO. 36) | HP16S rRNA |
| HP-513 | E25742 | 513-489 | gcgctctttacgcccagtgattccg (SEQ ID NO. 37) | HP16S rRNA |
| HP-775 | E25742 | 775-751 | gccctccaacaactagcatccatcg (SEQ ID NO. 36) | HP16S rRNA |

TABLE 2a

Grid A lists the different types of bacteria genomic DNA loaded onto nylon plus membrane and hybridized to random primed $^{32}$P-radiolabeled gene probes.

| | W | X | Y | Z |
|---|---|---|---|---|
| 1 | Placenta | Escherichia vulneris | Salmonella choleraesuis | |
| 2 | Helicobacter pylori | Hafnia alvei | Shigella flexneri | TG2 |
| 3 | Aeromonas jandanei | Klebsiella pneumoniae | Serratia marcescens | |
| 4 | Citrobacter freundii | Morganella morganii | Shigella sonnei | K12 |
| 5 | Cedecea lapagei | Proteus vulgaris | Yersinia enterocolitica | |
| 6 | Enterobacter cloacae | Providencia alcalifaciens | Escherichia blattae | 078: H11 |
| 7 | Escherichia hermannii | Pseudomonas aeruginosa | Enterobacter agglomerans | |
| 8 | Edwardsiella tarda | Shigella boydii | 219/1 Shigella sonnei | sssDNA |

TABLE 2a-continued

Grid B lists the different types of bacteria genomic DNA loaded onto nylon plus membrane and hybridized to random primed $^{32}$P-radiolabeled gene probes.

| | W | X | Y | Z |
|---|---|---|---|---|
| 1 | Placenta | Escherichia vulneris | Salmonella choleraesuis | 078: H11 |
| 2 | Helicobacter pylori | Hafnia alvei | Shigella flexneri | 142/31 |
| 3 | Aeromonas jandanei | Klebsiella pneumoniae | Serratia marcescens | K12 |
| 4 | Citrobacter freundii | Morganella morganii | Shigella sonnei | TG2 |
| 5 | Cedecea lapagei | Proteus vulgaris | Yersinia enterocolitica | 179/36 |
| 6 | Enterobacter cloacae | Providencia alcalifaciens | Escherichia blattae | 197/5 |
| 7 | Escherichia hermannii | Pseudomonas aeruginosa | Enterobacter agglomerans | 117/3B |
| 8 | Edwardsiella tarda | Shigella boydii | 219/1 Shigella sonnei | sssDNA |

TABLE 2a-continued

Grid C lists the different types of bacteria genomic DNA loaded onto nylon plus membrane and hybridized to random primed $^{32}$P-radiolabeled gene probes.

| | W | X | Y | Z |
|---|---|---|---|---|
| 1 | Placenta | Escherichia vulneris | Salmonella choleraesuis | 078: H11 |
| 2 | Helicobacter pylori | Hafnia alvei | Shigella flexneri | 196/1 |
| 3 | Aeromonas jandanei | Klebsiella pneumoniae | Serratia marcescens | K12 |
| 4 | Citrobacter freundii | Morganella morganii | Shigella sonnei | TG2 |
| 5 | Cedecea lapagei | Proteus vulgaris | Yersinia enterocolitica | 196/28 |
| 6 | Enterobacter cloacae | Providencia alcalifaciens | Escherichia blattae | 197/5 |
| 7 | Escherichia hermannii | Pseudomonas aeruginosa | Enterobacter agglomerans | 218/40 |
| 8 | Edwardsiella tarda | Shigella boydii | 219/1 Shigella sonnei | 0157: H7 |

Grid D lists the DNA of *E. coli* and gram positive bacteria isolated from patients' fecal specimen and loaded onto nylon plus membrane and hybridized to different random primed $^{32}$P labeled gene probes.

| | A | B | C | D | E | F |
|---|---|---|---|---|---|---|
| 1 | Placental | 139/6 | 158/20 | 174/TM5 | 206/13 | HP |
| 2 | 114/TB | 142/31 | 158/37 | 179/36 | 218/40 | 114/3g |
| 3 | 117/3B | 145/34 | 159/TM17 | 193/6 | 224/1 | 115/TA |
| 4 | 119/1TM1 | 145/40 | 162/20 | 196/1 | 231/1 | 116/TC |
| 5 | 129/20 | 152/W2-35 | 164/1 | 196/28 | 236/4 | 116/TD |
| 6 | 135/35 | 154/1 | 168/4 | 197/5 | 240/28 | 117/2D |
| 7 | 130/22 | 154/9 | 168/38 | 205/T18 | 252/22 | O157: H7 |
| 8 | 136/36 | 156/TM22 | 172/33 | 205/T34 | K12 | Staphylococcus |

Grid E lists the range of different amount of Enterobacter cloacae and K12 *E. coli* DNA loaded onto nylon plus membrane and hybridized to different types of random primed $^{32}$P gene probe.

| | Enterobacter Cloacae (ng) | *E. coli* K12 (ng) | *E. coli* K12 (ng) |
|---|---|---|---|
| 1 | | 1 | 1 |
| 2 | 100 | 2 | 2 |
| 3 | | 5 | 5 |
| 4 | 100 | 10 | 10 |
| 5 | | 20 | 20 |
| 6 | | 50 | 50 |

Grid F lists the *H. pylori* primer directed PCR amplified DNA product of *H. pylori* and *E. coli* DNA and total DNA of *H. pylori* and *E. coli* isolates obtained from patients' fecal specimens. These are loaded onto nylon plus membrane and hybridized to random primed $^{32}$P radiolabeled *H. pylori* ribosomal gene probe (HP).

| | A Volume of Diluted (1:10) PCR reaction mixture after amplification | B Rows 1–5: PCR reaction mixture Rows 6–8: HP Genomic DNA | C Rows 1–5: PCR reaction mixture Rows 6–8: *E. coli* Genomic DNA |
|---|---|---|---|
| 1 | 1 µl (HP) | 5 µl of HP diluted reaction mix 5 µl of K12 reaction mixture | 5 µl of K12 reaction mixture |
| 2 | 5 µl (HP) | 5 µl of HP diluted reaction mix 5 µl of 142/31 reaction mixture | 5 µl of 142/31 reaction mixture |
| 3 | 10 µl (HP) | 5 µl of HP diluted reaction mix 5 µl of 179/36 reaction mixture | 5 µl of 179/36 reaction mixture |
| 4 | 50 µl (HP) | 5 µl of HP diluted reaction mix 5 µl of 197/5 reaction mixture | 5 µl of 197/5 reaction mixture |
| 5 | 1 ul (mixed *E. coli* isolates) | 5 µl of HP diluted reaction mix 5 µl of 117/3B reaction mixture | 5 µl of 117/3B reaction mixture |
| 6 | 5 ul (mixed *E. coli* isolates) | 10 ng of HP genomic DNA | 10 ng of 117/3B genomic DNA |
| 7 | 10 ul (mixed *E. coli* isolates) | 50 ng of HP genomic DNA | 50 ng of 117/3B genomic DNA |
| 8 | 50 ul (mixed *E. coli* isolates) | 200 ng of HP genomic DNA | 200 ng of 117/3B genomic DNA |

TABLE 2b

Bacteria source.

| Bacterial genus | Bacteria species | Source |
|---|---|---|
| Escherichia (*E. coli*) | 078: H11 | ATCC 35401 |
| | 078: K80: H12 | ATCC 43896 |
| | 0157: H7 | ATCC 43895 |
| | 029: NM | ATCC 43892 |
| | 0111 | ATCC 33780 |
| | 0142: K86(B) | ATCC 23985 |
| | TG2 | gift |
| | K12 | ATCC 29947 |
| Escherichia (non-coli) | *E. hermannii* | ATCC 33650 |
| | *E. vulneris* | ATCC 33821 |
| | *E. blattae* | ATCC 29907 |
| Shigella | *S. flexneri* (serotype 2A) | ATCC 29903 |
| | *S. sonnei* | ATCC 29930 |
| | *S. boydii* (serotype 2) | ATCC 8700 |
| Edwardsiella | *E. tarda* (01433: H1) | ATCC 15947 |
| Salmonella | *S. choleraesuis* | ATCC 43971 |
| Citrobacter | *C. freundii* | ATCC 8090 |
| klebsiella | *K. pneumoniae* (Ozaenae type4) | ATCC 11296 |
| Enterobacter | *E. cloacae* | ATCC 13047 |
| Hafnia | *H. alvei* | ATCC 13337 |
| Serratia | *S. marcescens* | ATCC 13880 |
| Proteus | *P. vulgaris* | ATCC 13315 |
| Morganella | *M. morganii* | ATCC 49948 |
| Providencia | *P. alcalifaciens* | ATCC 9886 |
| Yersinia | *Y. enterocolitica* | ATCC 29913 |
| Cedecea | *C. lapagei* | ATCC 33432 |
| Aeromonas | *A. jandanei* | ATCC 49568 |
| Enterobacter | *E. agglomerans* | field isolates |
| Pseudomonas | *P. aeruginosa* | field isolates |
| Helicobacter | *H. pylori* | field isolates |
| Human | Placental DNA | Sigma (UK) |
| Salmon | Salmon sperm DNA | Sigma (UK) |

TG2: Gibson TJ: Studies on the Epstein-Bar-Virus Genome, Ph.D Thesis 1984. Cambridge University, UK.

TABLE 3

Result of in-vitro simulation of PCRISH.

| Bacterial genus | Bacteria species | b1007/b1008 genes | | ycdG/b1007 genes | | HP gene | |
|---|---|---|---|---|---|---|---|
| | | PCR primers OH-7419 OH-7985 | Probe primers OH-7562 81B-7794 | PCR primers 81B-7223 81B-7794 | Probe primers 81B-7278 81B-7754 | PCR primers HP-178 HP-775 | Probe primers HP-228 HP-513 |
| Escherichia (E. coli) | 078: H11 | + | + | + | + | − | − |
| | TG2 | + | + | + | + | − | − |
| | K12 | + | + | + | + | − | − |
| | 142/31 | + | + | + | + | − | − |
| | 179/36 | + | + | + | + | − | − |
| | 197/5 | + | + | + | + | − | − |
| Escherichia (non-coli) | E. hermannii | − | − | − | − | − | − |
| | E. vulneris | + | − | − | − | − | − |
| | E. blattae | − | − | − | − | − | − |
| Shigella | S. flexneri (serotype 2A) | + | + | + | + | − | − |
| | S. sonnei | + | + | + | + | − | − |
| | S. sonnei: 219/1 | + | + | + | + | − | − |
| | S. boydii (serotype 2) | − | − | − | − | − | − |
| Edwardsiella | E. tarda (01433: H1) | − | − | − | − | − | − |
| Salmonella | S. choleraesuis | + | − | − | − | − | − |
| Citrobacter | C. freundii | − | − | − | − | − | − |
| Klebsiella | K. pneumoniae (Ozaenae type4) | − | − | − | − | − | − |
| Enterobacter | E. cloacae | − | − | − | − | − | − |
| Hafnia | H. alvei | − | − | − | − | − | − |
| Proteus | P. vulgaris | − | − | − | − | − | − |
| Morganella | M. morganii | − | − | − | − | − | − |
| Providencia | P. alcalifaciens | + | − | − | − | − | − |
| Yersinia | Y. enterocolitica | − | − | − | − | − | − |
| Cedecea | C. lapagei | + | − | − | − | − | − |
| Aeromonas | A. jandanei | − | − | − | − | − | − |
| Enterobacter | E. agglomerans | − | − | − | − | − | − |
| Pseudomonas | P. aeruginosa | − | − | − | − | − | − |
| Helicobacter | H. pylori | − | − | − | − | + | + |
| Human | Placental DNA | − | − | − | − | − | − |
| Salmon | Salmon sperm DNA | − | − | − | − | − | − |

The invention claimed is:

1. A probe nucleotide sequence which is specific to *E. coli*- and/or *Shigella* species or related microorganism, the nucleotide sequence consisting of a sequence from SEQ ID NO: 40, the sequence from SEQ ID NO: 40 comprising at least one of the sequence consisting of nucleotides 415 to 1351, the sequence consisting of nucleotides 3151 to 4359, the sequence consisting of nucleotides 4807 to 5235, the sequence consisting of nucleotides 6073 to 7359, the sequence consisting of nucleotides 7223 to 7794, the sequence consisting of nucleotides 7278 to 7773, the sequence consisting of nucleotides 7419 to 7985, the sequence consisting of nucleotides 7562 to 7794, the sequence consisting of nucleotides 8160 to 9704 or the sequence consisting of nucleotides 9731 to 11375, and present mainly in the nucleus of cancer cells and in the normal cells adjacent to cancer cells, for the identification of a gastrointestinal cancer or tumour or a predisposition to same.

2. A method for detecting the presence of *E. coli* or *Shigella* species or related microorganisms in a sample, said method comprising subjecting said sample to genetic analysis using an *E. coli-* or *Shigella* species-specific nucleotide sequence consisting of a sequence from SEQ ID NO: 40, the sequence from SEQ ID NO: 40 comprising at least one of the sequence consisting of nucleotides 415 to 1351, the sequence consisting of nucleotides 3151 to 4359, the sequence consisting of nucleotides 4807 to 5235, the sequence consisting of nucleotides 6073 to 7359, the sequence consisting of nucleotides 7223 to 7794, the sequence consisting of nucleotides 7278 to 7773, the sequence encompassed by nucleotides 7419 to 7985, the sequence consisting of nucleotides 7562 to 7794, the sequence consisting of nucleotides 8160 to 9704 or the sequence consisting of nucleotides 9731 to 11375.

3. The method according to claim 2 wherein said genetic analysis comprises amplification of nucleotide sequence present in the sample.

4. The method according claim 2 wherein said *E. coli-* and/or *Shigella* species-specific nucleotide sequence is labeled to provide an identifiable signal.

5. The method according to 2 wherein the sample comprises a nucleic acid preparation from food, water, semi-solids or semi-liquid material, mammalian tissue, or extract or cells thereof or a nucleic acid preparation from said tissue, extract or cells.

6. The method according to claim 5 wherein the sample is mammalian tissue or extract or cells thereof.

7. The method according to claim 6 wherein the tissue, extract or cells are from a patient suffering from cancer or cellular instability or gastrointestinal infection, or a patient at risk of cancer or cellular instability.

8. The method according to claim 7 wherein the cancer is gastrointestinal cancer.

9. The method according to claim 7 wherein the cancer is colon cancer.

10. The method according to claim 7 wherein the cancer is stomach cancer.

11. The method according to claim 7 wherein the cancer is colorectal cancer.

12. An isolated nucleic acid molecule comprising the probe nucleotide sequence of claim 1 wherein said probe nucleotide sequence is capable of specifically hybridizing to *E. coli-* and/or *Shigella* species'-derived nucleic acid molecules.

13. A method of testing and selecting sequences specific to *E. coli* or *Shigella* species or related microorganisms in a sample, said method comprising subjecting a nucleic acid molecule preparation from said sample to genetic analysis using one or more *E. coli* or *Shigella* species'-specific nucleotide sequences consistig of a sequence from SEQ ID NO: 40, the sequence from SEQ ID NO: 40 comprising at least one of the sequence consisting of nucleotides 415 to 1351, the sequence consisting of nucleotides 3151 to 4359, the sequence consisting of nucleotides 4807 to 5235, the sequence consisting of nucleotides 6073 to 7359, the sequence consisting of nucleotides 7223 to 7794, the sequence consisting of nucleotides 7278 to 7773, the sequence consisting of nucleotides 7419 to 7985, the sequence consisting of nucleotides 7562 to 7794, the sequence consisting of nucleotides 8160 to 9704 or the sequence consisting of nucleotides 9731 to 11375.

14. The method according to claim 13 wherein said genetic analysis comprises amplification of nucleotide sequence present in the sample.

15. The method according to claim 13 wherein said *E. coli-* and/or *Shigella* species-specific nucleotide sequence is labeled to provide an identifiable signal.

16. The method according to claim 13 wherein the sample comprises mammalian tissue or extract or cells thereof.

17. The method according to claim 16 wherein the tissue, extract or cells are from a patient suffering from cancer or cellular instability or gastrointestinal infection, or a patient at risk of cancer or cellular instability.

18. The method according to claim 17 wherein the cancer is gastrointestinal cancer.

19. The method according to claim 17 wherein the cancer is colon cancer.

20. The method according to claim 17 wherein the cancer is stomach cancer.

21. The method according to claim 17 wherein the cancer is colorectal cancer.

22. A nucleotide sequence identified by the method according to claim 13 wherein said sequence is capable of specifically hybridizing to *E. coli* and/or *Shigella* species'-derived nucleic acid molecules.

* * * * *

SEQUENCE LISTING

<160> NUMBER OF SEQ ID NOS: 41

<210> SEQ ID NO 1
<211> LENGTH: 21
<212> TYPE: DNA
<213> ORGANISM: Artificial
<220> FEATURE:
<223> OTHER INFORMATION: primer

<400> SEQUENCE: 1
atgactggtt tagtaaaatg g                                             21

<210> SEQ ID NO 2
<211> LENGTH: 21
<212> TYPE: DNA
<213> ORGANISM: Artificial
<220> FEATURE:
<223> OTHER INFORMATION: Primer

```
<400> SEQUENCE: 2
tcaatattca ctgttaacct c                                              21

<210> SEQ ID NO 3
<211> LENGTH: 21
<212> TYPE: DNA
<213> ORGANISM: Artificial
<220> FEATURE:
<223> OTHER INFORMATION: Primer

<400> SEQUENCE: 3
cattgcgtaa ccaatcaccg c                                              21

<210> SEQ ID NO 4
<211> LENGTH: 21
<212> TYPE: DNA
<213> ORGANISM: Artificial
<220> FEATURE:
<223> OTHER INFORMATION: Primer

<400> SEQUENCE: 4
gcaagtagca cgacatttgt c                                              21

<210> SEQ ID NO 5
<211> LENGTH: 20
<212> TYPE: DNA
<213> ORGANISM: Artificial
<220> FEATURE:
<223> OTHER INFORMATION: Primer

<400> SEQUENCE: 5
ggtgcaagcc tctacgccgc                                                20

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
tgccgcctct gccgcaatgg                                                20

<210> SEQ ID NO 7
<211> LENGTH: 25
<212> TYPE: DNA
<213> ORGANISM: Artificial
<220> FEATURE:
<223> OTHER INFORMATION: Primer

<400> SEQUENCE: 7
aacttgccga gcgtgaatgg gcgcg                                          25

<210> SEQ ID NO 8
<211> LENGTH: 25
<212> TYPE: DNA
<213> ORGANISM: Artificial
<220> FEATURE:
<223> OTHER INFORMATION: Primer

<400> SEQUENCE: 8
gtggcctgca acttgctcca ctcgg                                          25

<210> SEQ ID NO 9
```

<211> LENGTH: 25
<212> TYPE: DNA
<213> ORGANISM: Artificial
<220> FEATURE:
<223> OTHER INFORMATION: Primer

<400> SEQUENCE: 9
tatccgatgg tacgcgtgga ctggc                                              25

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
gcaatgtgct tcacatgctc gcgcc                                              25

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
gaccacgctg acagcacaac                                                    20

<210> SEQ ID NO 12
<211> LENGTH: 20
<212> TYPE: DNA
<213> ORGANISM: Artificial
<220> FEATURE:
<223> OTHER INFORMATION: Primer

<400> SEQUENCE: 12
ggtggtcgca ctccactaac                                                    20

<210> SEQ ID NO 13
<211> LENGTH: 22
<212> TYPE: DNA
<213> ORGANISM: Artificial
<220> FEATURE:
<223> OTHER INFORMATION: Primer

<400> SEQUENCE: 13
gctttccccc aatctttacg tg                                                 22

<210> SEQ ID NO 14
<211> LENGTH: 23
<212> TYPE: DNA
<213> ORGANISM: Artificial
<220> FEATURE:
<223> OTHER INFORMATION: Primer

<400> SEQUENCE: 14
gatttacgcg agataacgct atg                                                23

<210> SEQ ID NO 15
<211> LENGTH: 22
<212> TYPE: DNA
<213> ORGANISM: Artificial
<220> FEATURE:
<223> OTHER INFORMATION: Primer

<400> SEQUENCE: 15

```
cgctaatcgc cgcagctgtg gc                                            22

<210> SEQ ID NO 16
<211> LENGTH: 24
<212> TYPE: DNA
<213> ORGANISM: Artificial
<220> FEATURE:
<223> OTHER INFORMATION: Primer

<400> SEQUENCE: 16
cgctatcaaa cttatccatc gggc                                          24

<210> SEQ ID NO 17
<211> LENGTH: 30
<212> TYPE: DNA
<213> ORGANISM: Artificial
<220> FEATURE:
<223> OTHER INFORMATION: Primer

<400> SEQUENCE: 17
tgtgaaacgt caaataattc ctgcgctgcg                                    30

<210> SEQ ID NO 18
<211> LENGTH: 30
<212> TYPE: DNA
<213> ORGANISM: Artificial
<220> FEATURE:
<223> OTHER INFORMATION: Primer

<400> SEQUENCE: 18
catgtacgga catattgaaa cgatggcacg                                    30

<210> SEQ ID NO 19
<211> LENGTH: 22
<212> TYPE: DNA
<213> ORGANISM: Artificial
<220> FEATURE:
<223> OTHER INFORMATION: Primer

<400> SEQUENCE: 19
ctcctgatga acaacttctg gc                                            22

<210> SEQ ID NO 20
<211> LENGTH: 18
<212> TYPE: DNA
<213> ORGANISM: Artificial
<220> FEATURE:
<223> OTHER INFORMATION: Primer

<400> SEQUENCE: 20
ggatccagcc ccatcaga                                                 18

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
cgtgttgaac gcccattact                                               20

<210> SEQ ID NO 22
<211> LENGTH: 20
<212> TYPE: DNA
```

-continued

<213> ORGANISM: Artificial
<220> FEATURE:
<223> OTHER INFORMATION: Primer

<400> SEQUENCE: 22
tcgacctcta cagagagcgg                                              20

<210> SEQ ID NO 23
<211> LENGTH: 18
<212> TYPE: DNA
<213> ORGANISM: Artificial
<220> FEATURE:
<223> OTHER INFORMATION: Primer

<400> SEQUENCE: 23
acaagcaggg cgcatcag                                                18

<210> SEQ ID NO 24
<211> LENGTH: 29
<212> TYPE: DNA
<213> ORGANISM: Artificial
<220> FEATURE:
<223> OTHER INFORMATION: Primer

<400> SEQUENCE: 24
acgaaaccag agcctcttcc agttgcggg                                    29

<210> SEQ ID NO 25
<211> LENGTH: 20
<212> TYPE: DNA
<213> ORGANISM: Artificial
<220> FEATURE:
<223> OTHER INFORMATION: Primer

<400> SEQUENCE: 25
gcccacatta ctggtgtgcc                                              20

<210> SEQ ID NO 26
<211> LENGTH: 21
<212> TYPE: DNA
<213> ORGANISM: Artificial
<220> FEATURE:
<223> OTHER INFORMATION: Primer

<400> SEQUENCE: 26
ctgcagtgtg accgatacgc c                                            21

<210> SEQ ID NO 27
<211> LENGTH: 20
<212> TYPE: DNA
<213> ORGANISM: Artificial
<220> FEATURE:
<223> OTHER INFORMATION: Primer

<400> SEQUENCE: 27
atagcagcaa gctttatgcg                                              20

<210> SEQ ID NO 28
<211> LENGTH: 20
<212> TYPE: DNA
<213> ORGANISM: Artificial
<220> FEATURE:
<223> OTHER INFORMATION: Primer

<400> SEQUENCE: 28
cggcaagttg tgggctggag                                              20

```
<210> SEQ ID NO 29
<211> LENGTH: 21
<212> TYPE: DNA
<213> ORGANISM: Artificial
<220> FEATURE:
<223> OTHER INFORMATION: Primer

<400> SEQUENCE: 29
cgtaattatt cccgctggca g                                    21

<210> SEQ ID NO 30
<211> LENGTH: 19
<212> TYPE: DNA
<213> ORGANISM: Artificial
<220> FEATURE:
<223> OTHER INFORMATION: Primer

<400> SEQUENCE: 30
gcgatatgag caaaggacg                                       19

<210> SEQ ID NO 31
<211> LENGTH: 20
<212> TYPE: DNA
<213> ORGANISM: Artificial
<220> FEATURE:
<223> OTHER INFORMATION: Primer

<400> SEQUENCE: 31
ctgtcgatga tcaaactgcg                                      20

<210> SEQ ID NO 32
<211> LENGTH: 20
<212> TYPE: DNA
<213> ORGANISM: Artificial
<220> FEATURE:
<223> OTHER INFORMATION: Primer

<400> SEQUENCE: 32
gcatctccat acagaacagg                                      20

<210> SEQ ID NO 33
<211> LENGTH: 20
<212> TYPE: DNA
<213> ORGANISM: Artificial
<220> FEATURE:
<223> OTHER INFORMATION: Primer

<400> SEQUENCE: 33
ctgggttact tcgggcagcc                                      20

<210> SEQ ID NO 34
<211> LENGTH: 20
<212> TYPE: DNA
<213> ORGANISM: Artificial
<220> FEATURE:
<223> OTHER INFORMATION: Primer

<400> SEQUENCE: 34
cggagccgaa tgatagtgcg                                      20

<210> SEQ ID NO 35
<211> LENGTH: 22
<212> TYPE: DNA
<213> ORGANISM: Artificial
<220> FEATURE:
```

-continued

```
<223> OTHER INFORMATION: Primer

<400> SEQUENCE: 35
gctaagagat cagcctatgt cc                                            22

<210> SEQ ID NO 36
<211> LENGTH: 25
<212> TYPE: DNA
<213> ORGANISM: Artificial
<220> FEATURE:
<223> OTHER INFORMATION: Primer

<400> SEQUENCE: 36
accaaggcta tgacgggtat ccggc                                         25

<210> SEQ ID NO 37
<211> LENGTH: 25
<212> TYPE: DNA
<213> ORGANISM: Artificial
<220> FEATURE:
<223> OTHER INFORMATION: Primer

<400> SEQUENCE: 37
gcgctcttta cgcccagtga ttccg                                         25

<210> SEQ ID NO 38
<211> LENGTH: 25
<212> TYPE: DNA
<213> ORGANISM: Artificial
<220> FEATURE:
<223> OTHER INFORMATION: Primer

<400> SEQUENCE: 38
gccctccaac aactagcatc catcg                                         25

<210> SEQ ID NO 39
<211> LENGTH: 11275
<212> TYPE: DNA
<213> ORGANISM: E. coli
<220> FEATURE:
<221> NAME/KEY: misc_feature
<223> OTHER INFORMATION: AE 000201

<400> SEQUENCE: 39
aagccagcga tatttaagac cgccggacgg ctaaataaa atttgcttaa tctcaattat     60
catgcgttaa tagctgcgtc ggtttgaaag acagacagca tacaaagtag tttactaaag   120
cagttctcat tatcaggcat tatccccttc ttttgagtct ctctcctgaa cactaagtag   180
tttctgtatt aaagccctgt tgccgaaag gcccaaaatg aaggaagtaa atatgtcta    240 ataaaatgac tggtttagta aaatggttta acgcagataa aggttttggc tttatcactc   300
ctgatgatgg cagcaaagac gttttcgtcc atttcaccgc catccagagc aatgaattcc   360
gcacgctgaa cgaaaatcag aaagttgaat tttctattga gcagggcaa cgtggccccg   420 cggcagcgaa cgttgttacg ctctaaggtt gccattatta ctcaacatct ccatttccgc   480
tgtccatgtt gtcatggttc acagtaccgc acatcggcat tcgatgtgac ggagcgaaac   540
cctttgggcg ctaagtgtat tttttgtaaa tcgacgatga tcacctttga taacgtcgcg   600
ctgcaaatac gcactgacca tgcgccgctg gatttcacaa aataatatca ggctccctcg   660
tggagccttt tttatatctg ccttattttt cttcaacgct gtatgtatag taagcgataa   720
cctgttgatt attgaatctt tcggggagat ggcttataac atttcttacc tgaccaggt   780
```

-continued

```
accgggaacc aacaccttac tggcgtgttg ctgtcttttta agaccagaag aggttaacag    840
tgaatattga agagttaaaaa aaacaagccg aaacggaaat cgccgacttt atcgcgcaaa    900
aaatcgccga gctgaacaag aatacaggga agaagtctc tgaaattcgc ttcaccgcac    960
gagaaaaaat gaccgggctt gaaagttatg atgtcaaaat caaaataatg tgattttgtg   1020
aacatcaccc cgtgcgaggt gatgttccgc ttgttgctaa tttagtgacc aatcattggc   1080
gcttgtggaa ttaagcgtcg gtacaattcc tccggcaccg ggctttgcca tactcccgca   1140
tacattgcgt aaccaatcac cgcaaacata atccccagaa ccagtagcgt cattaaccag   1200
ccagacaacg caaaggcttt tttatttgcc gcaggttttt gcagtgaaaa ggtcaatgtt   1260
gaggctaccg gacatgactc tacgcaagtc atacagccgg tacattccac tgttcgtacc   1320
tgaattaatt tatcgaccgg gatccgtgat gggcaatttt ttgcgcattt gccacagtcg   1380
atacaacttt cggcattgcg acgaatctta aacggcgaca atagcgaaac cacgcccatc   1440
agcgcgccat atgggcaaag ataacgcaca caggcatggc gaataaacag gctggcaatc   1500
agcaaaacgg tcacgctgat taatgtcgcg gtccccatat gacgaaagaa atcgagcatt   1560
ttaacgtcca tcaccacgct gtagggcgac aacataaaat agtgaatcgc ctgagcgggc   1620
atcaataacg cgatatagat aaaaaaactc aacagcaaat acttcacgcc gcgcagagga   1680
atatccagcc agcggggaag gacacattgc cgaccaaaca gtttgttacc gagatcgccg   1740
attaattcag aaagcgtacc aaccgggcat aaccatgagc aaaaggcctt tttgagtaat   1800
agactgatga cgataaaaagc gaccaataac agcatcgcgg cggcgtggac ggacggtaac   1860
tgacctgtta caaggctata tttcagattc atcagcccgg caatcggtag ccagccttcg   1920
atacctcccg gtctggcgac aaatgtcgtg ctacttgccg tttcgtaata gcgcacccaa   1980
taccagaacg tgatggcaat ataaatattc attgccaaca gtaataattg cgtcgcttta   2040
cgccaggtcg tggcattacg ccagtcattc acggtaatt tgccgcccgt cgtgcctggc   2100
cgccgctgcc agcgggttct tttattctct gccatgattt tgccagtccg ttaagttgta   2160
taccaaatgc cactattcta gttgttctta actggctgat attgattcaa atcgcgttca   2220
ggtctttctt atgcaaccat gcttccagag cggcaacact gcgtgtaatt tcttcgtgtg   2280 gaagggggc agataatggc tgctgctcca gttgtgcgca tagctggctg gcgatatgca   2340
ttcccagact cgagcaactg cttttttagct gatgcgcggc acgctttatt ttctcgctat   2400
cctgactggc gcgggcaatg tcgatttcat cgagaagcgg cagggcatgt tgtgtaaata   2460
ataccagcca ttcgtggatc ttctccgtcc ccattaactg agcatcttca ttgagttgcg   2520
atacatccag cgattgatca ttattgactt gcagttggag atagtgcgcc agtaactgac   2580
cgagcacttc acgcggcacc ggtttaggga taatcccgcg gaataatgaa ctggtacgct   2640
ggcgcagcgt ttcgtcaatg acatgggcgc taaagccaat caaaaccagc gacggatatt   2700
gctgtgccag ttgtcgggca agcgtaatgc cgtcgatatc cggcagatca aaatccacca   2760
gtgcggcagc aaacggttcg ctattttgca gtgtctctaa agcctgcgcg gcattgccaa   2820
cagcaacaat ctgcgcacca ctggttttca gcatctcaat ggtaattcgc tgggttagcg   2880
ggttatcttc aattaacagc aaacgtaaac cgtcaagacg caccgcctga ttgactgttt   2940
ttggcacggg tgccgtggca acacgtaacg gcaagcgtaa acaaaaacag cttccaacct   3000
ccggcgtgct ggtggcgctc agttcgccgc ccatcgcctg ggccagacgg ctactgatag   3060
tcagtcccag cccggtgccg ccgcgtttgc cgcttacctg cacaaatggc tggaagattt   3120
ctgccagttt cgcgggatca ataccgcagc cgctgtcttc cacttcgacc agccattgct   3180
```

```
cgccatcagt gcgactacgc aggataatgt acccttcgtc agtaaaacgc agggcgttgc   3240
tcaacaggtt ggttataacc tgacgaatac gtcgtggatc gcccattaac gcgcacggca   3300
tatcatcggc aattgccgtt gccaggcgaa tcgggcgacc tttcacccgt ccgctcatta   3360
attgcagggt actttccagc agcgggcgcg gttcaaaggg ctcatcgctg accgaaacat   3420
tcttgccacc tgcttcgata gcggaataat cgagaatatc gttgaggatg gtcagcaacg   3480
attcaccaga gtcagtaatt gcccgcaaat catcacgctg ggcgttaagt gcggggttat   3540
ctgccagcag ttgagcagtg ccgagaatac cgtacagcgg tgtgcggatc tcatggctca   3600
tcgccgccag aaacgccgat tttgcctggc tggcttttc tgcttccgcc cgtgcctgtc   3660
ggtgttctat caccagttcc tgcaattcag ctgtacgcgc tttgacctgc gccgccagct   3720
gttcgcggtg gcgattcagt gcatgaacat tgctgcgaaa cgcatccatc agccgcccga   3780
tggtatccag ctcccgtacg ccagcggttt ccgggaaagg ggagtcaata tcaccgtcca   3840
gcagccgttg cagcgcctgc gtttgttcgg caagtggacg cgtgactgag cgataaacca   3900
cgcgccagag gatcagaatc agtgcgcaaa gtgaaaccat ccccagcaat aacaggctgt   3960
attgcccgcg tgcactcgct ttttccagat gcgccagtcc gtgctgatta cgcagctcaa   4020
tggtgtcgac cagctgactg acttcgctac taaactgcgc gaactgggcg atgttatttt   4080
gtgcgagagt ttgtaggtga ttgctgattt cactgtcctg ctgatacagc gccagcaaat   4140
cgctatattg gctaacggta gttaacgttg ttgcgacctg cgcacgaaca cccgatctt    4200 caatgcgtat ttgccgacgt tgcagaattt tcaccgcatt attgagctgc ttttccagcg   4260
ttggtgcatt tttctggatc tgctccagcc ccagattcat caccatttgc tgcacccgca   4320
gagcgctaag gcgcagttca ttcatctggt taacatactc aagatcgata tcaatcagcc   4380
gatcgagtgc actttcagca gcctgacgct gatcttgttc gatcaaatcg taaatcccgg   4440
cctgggtcgc tccagcggaa gttgtcgcat tattcgcctg accttgcgcc aggcgtgcga   4500
tctcatcggc ggcagcgact atctgctgac tgagttgctg ttgttgctgg cgcagttgca   4560
aacgctgccc caccagttcc ccttgctgac gtaacgaacg ggagatctcc tgctcctgtt   4620
gttcaatagc ggtggtatca aaccttgtt cccgtaacgc ttgcagcaac gcattaatct    4680
tcaggctttg tgcggtgagc attcgcccct gcgcctgcca catcttttcg ttatcggcac   4740
tggtcaggtt ctgcgcggcg aaaagttccc aggcgctggc ttcgctcaac tggcgcgcca   4800
tattcatggt aggaatcaat gcctgagtgt tgtctttttc cacctggctg ataaagcgca   4860
ggttgtacca tcccaccagg gtactggtca gggttaacag cgccatcagg gcaaagccca   4920
tccagagtct tcgggtcagg gttaaattca cggtcggtgc actttaggtg aaaaaggttg   4980
agtcgcaaag cggaatgcat ctagcataaa gccttattat tgatgaggct atcatgcgcg   5040
tactgctatt tttacttctt tccctttttca tgttgccggc attttcggct gataacctgt   5100
tgcgctggca tgatgcgcag catttcacgg tgcaagcctc tacgccgctt aaagccaaac   5160
gcgcatggaa actgtgcgcg ctttatccca gcctgaaaga ttcatattgg ttatcgttga   5220
actatggtat gcaggaggct gctcgccgct acggtgtgga tttaaaagtg ctggaggcag   5280
gcggctacag ccagttggct acccagcaag cacaaatcga ccagtgtaaa cagtggggcg   5340
cagaggccat tttgctcggt agtagcacga cctcatttcc cgacctgcaa aagcaggtag   5400
caagtctgcc ggtgatcgaa ctggtaaatg ctattgatgc tccccaggtg aaaagccgcg   5460
ttggtgtgcc ctggtttcag atgggctatc aaccggggcg atatctggtg caatgggcgc   5520
```

-continued

```
acggtaaacc actgaatgtg ctgttgatgc ccggacccga taacgccggg ggcagtaagg      5580
agatggtcga aggttttcgc gcagccattg ccggaagccc ggtgcgtatt gttgatattg      5640
cgcttggtga taacgatatt gaaatccagc gtaacctgtt gcaggagatg ctggaacgcc      5700
atccagaaat cgacgtcgtt gccggaacgg ccattgcggc agaggcggca atgggggaag      5760
ggcgtaacct gaaaacgccg cttaccgtgg tgtcgtttta tctttcacat caggtgtatc      5820
gcgggctgaa gcgggaaga gtgattatgg ctgccagcga tcaaatggtc tggcaggggg      5880
aactggcggt tgagcaggcc atcaggcaat tacagggggca atcggtttct gataatgtca      5940
gcccaccgat tttagttctg acgccgaaaa atgccgaccg tgaacatatt cgccgctcgc      6000
tgtcaccagg gggatttcgt ccggtctatt tttatcagca cacatcagcg gctaagaaat      6060
aaccttcacc atgttgcgtc accagtaaat ccgcgctgag tttatgacgt aaacgacgaa      6120
ttaacacatc gacggtgcgc aggtcagggt tttccacccg acgcgcagaa agcatacgta      6180
gcagacgttc acggctgaga atttcgcccg gattcgtcac aaatgccacc aacatttcat      6240
actctgcgcg ggtcagttta atcggctcgc catcccgctc cagcgtatgg cgcgacacat      6300
tcaggcaata accggcaaag cgatagcagt tgtcctgagt gtgcggttga gcttgtcgcg      6360
cgaggtcgat tcgccagagc agatttttca cccgtactac cagttcgcgc agttccagcg      6420
gtttggtgac gtaatcgtct gcgcccattt ccagcccaac aatacggtca atccgatcgc      6480
tgcgtccggt aaccagaata atccccaccg ttgagcgttc tcgcagggcg cgggttaaca      6540
tcaggccatt ttcatcgggt aagttgatat ccagcagaat taaatctacc gactgattct      6600
gcataatttc ccgtagccca gcaccgctcg ccgtaacgga aacggtatac ccctcctgag      6660
tgaagtagga ttgtaatcgc gcctgggtaa ccggctcatc ttcaacaata acaatgtgat      6720
gtggcatcag agggttttac tcattctgtt catatctgtt catattctgc cgtaagccgt      6780
tcatcctgac cagtgccgct gttcatattt gctcattaag atcgcttcac taaaccataa      6840
ttctacaggg gttattatgc ggaaactctg gaacgcgcta cgccgaccca gtgctcgttg      6900
gtcggtactg gcgctggtcg caattgggat tgtgattggc attgcgctga ttgtattgcc      6960
acacgttggg atcaaagtca ccagcacaac cgaattttgt gtcagttgcc acagtatgca      7020
accggtgtat gaagaatata acagtcggt gcatttccag aacgcctccg gcgtgcgagc      7080
tgaatgccat gactgtcata tcccgccgga tattccaggc atggtgaagc gcaaactgga      7140
agcgagcaat gatatctacc agacctttat tgctcactcc attgatacac ctgaaaaatt      7200
cgaagccaaa cgcgcggaac ttgccgagcg tgaatgggcg cgaatgaaag aaaacaactc      7260
ggcaacctgc cgctcctgcc ataactacga tgcgatggat catgcgaagc agcatcctga      7320
agcagcacgt cagatgaagg tggcagcgaa agataatcaa tcctgcatcg actgtcataa      7380
aggtattgcc caccagttac cggatatgag tagcggcttc cgtaagcagt tcgatgagct      7440
gcgcgccagt gctaatgaca gtggtgacac gctgtactct attgatatta agccaattta      7500
tgcggcgaaa ggcgataaag aagcctctgg ttctctgctg cctgcttcgg aagtgaaagt      7560
ccttaaacgt gacggcgact ggctgcaaat tgaaattacc ggctggacgg aaagcgccgg      7620
acgtcagcgt gtactcaccc aattcccagg taaacgcatc tttgttgcct cgattcgtgg      7680
tgatgtgcag cagcaggtaa aaacgctgga gaaaccacc gttgccgaca ccaataccga      7740
gtggagcaag ttgcaggcca ctgcgtggat gaagaaaggc gacatggtga acgatatcaa      7800
accgatctgg gcttatgcgg attcgttgta caacggcacc tgtaaccagt gccacgcgc      7860 accggaaatc gcccactttg acgctaacgg ttggatcggc acgctcaacg gcatgattgg      7920
```

```
ctttaccagt ctcgataaac gtgaagaacg caccttgttg aaatatctgc aaatgaatgc   7980
gtctgacacc gcaggtaagg ctcacggcga taagaaggaa gaaaaataat gaacaataac   8040
gatctctttc aggcatcacg tcggcgtttt ctggcacaac tcggcggctt aaccgtcgcc   8100
gggatgctgg ggccgtcatt gttaacgccg cgacgtgcga ctgcggcgca agcggcgact   8160
gacgctgtca tctcgaaaga gggcattctt accgggtcgc actgggggggc tatccgcgcg   8220 acggtgaagg atggtcgctt tgtggcggca aaaccgttcg aactggataa atatccgtcg   8280
aaaatgattg ccggattgcc ggatcacgta cacaacgcgg cgcgtattcg ttatccgatg   8340
gtacgcgtgg actggctgcg taagcgccat ctcagcgata cctcccagcg cggtgataac   8400
cgttttgtgc gcgtgagctg ggatgaagcc ctcgacatgt tctatgaaga actggaacgc   8460
gtgcagaaaa ctcacgggcc gagtgccttg ctgaccgcca gtggttggca atcgacgggg   8520
atgttccata acgcttcggg gatgctggcg aaagctattg ccttgcatgg taatagcgtt   8580
ggtacgggcg gagattactc taccggtgct gcgcaggtga tcctgccgcg cgtagtcggt   8640
tcgatggaag tgtatgaaca gcaaacctcc tggccgctgg tattgcagaa cagcaaaacc   8700
attgtgctgt ggggctccga tttgctgaaa aaccagcaag cgaactggtg gtgcccggat   8760
cacgatgttt atgaatatta cgcgcagcta aaagcgaaag tcgccgccgg tgaaattgag   8820
gtcatcagca tcgatccggt tgtcacatcc acccatgagt atctggggcg cgagcatgtg   8880
aagcacattg cggttaaccc gcaaactgac gtgccgctgc aactggcgct ggcacatacg   8940
ctgtacagtg aaaacctgta cgacaaaaac ttccttgcta actactgtgt gggttttgag   9000
cagttcctgc cgtatctgct gggtgagaaa gacggtcagc cgaaagatgc cgcatgggct   9060
gaaaaactga ccggcattga tgccgaaacc attcgtgggc tggcgcggca gatggcggcg   9120
aacagaacgc aaattattgc tggctggtgc gtgcagcgta tgcagcacgg tgaacagtgg   9180
gcgtggatga ttgtggttct ggcggcgatg ctggggcaaa ttggcctgcc aggtggtggt   9240
tttggttttg gctggcacta caacggcgca ggcacgccgg ggcgtaaagg cgttattctg   9300
agtggtttct ccggctctac gtcgattccg cctgttcacg acaacagtga ctacaaaggc   9360
tacagcagca ctattccgat tgcccgtttt atcgatgcga tcctcgaacc ggggaaagtg   9420
atcaactgga acggtaaatc ggtaaaactg ccgccgctga aatgtgtat ttttgccgga   9480 actaacccat tccatcgcca tcagcagatc aaccgcatta ttgaaggctt gcgcaagctg   9540
gaaacggtta tcgccataga taaccagtgg acctcaacct gccgctttgc cgatatcgta   9600
ctgcctgcga ccacgcagtt tgagcgtaac gatctcgacc agtacggcaa tcactccaac   9660
cgtggcatta tcgccatgaa acaggtggtg ccgccgcagt tcgaggcgcg caacgacttc   9720 gatatttttcc gcgagctgtg ccgtcgcttt aatcgcgaag aagcctttac cgaagggctg   9780
gacgaaatgg gctggctgaa acgcatctgg caggaaggtg tacagcaagg caaaggacgc   9840
ggcgttcatc tgccagcgtt tgatgacttc tggaataaca aagagtacgt cgagtttgac   9900
catccgcaga tgtttgttcg ccaccaggca ttccgcgaag atccggatct cgaaccgctg   9960
ggcacgccga gtggcctgat tgagatctac tcgaaaacta tcgccgatat gaactacgac  10020
gattgtcagg ggcatccgat gtggtttgag aaaatcgaac gctcccacgg tgggcctggc  10080
tcgcaaaagt atccgttgca tctgcaatct gtgcatccgg atttccgact tcactcgcag  10140
ttatgtgagt cggaaacgct gcgtcagcaa tatacggtag cgggtaaaga gccagtattc  10200
attaacccgc aggatgccag cgcgcgcggt attcgtaacg gtgatgtggt acgcgtcttt  10260
```

-continued

```
aacgctcgcg gtcaggtgtt ggcaggggca gtggtttctg accgctatgc acccggcgtg   10320
gcacgaattc acgaagggc atggtacgat ccagataaag cggcgagcc tggtgcgctg      10380 tgcaaatacg gtaaccccaa cgtgttgacc atcgacatcg gtacatcgca gctggcgcag   10440
gcgaccagtg cgcacactac gctggtggaa attgagaagt acaacggaac agtggagcag   10500
gtgacggcgt taacggccc cgtggagatg gtggcgcagt gcgaatatgt tcccgcgtcg    10560
caggtgaaat catgaccacg ctgacagcac aacagattgc ctgtgtttac gcctggctag   10620
cgcagttgtt ctcccgtgag ctggacgatg aacaactgac gcaaatcgcc agtgcgcaga   10680
tggctgaatg gttttcgttg ctgaaaagcg aaccgccgct cactgcggcg gtgaacgagc   10740
tggaaaaccg tattgccacg ctgacagtac gtgacgatgc ccgtctggaa ctggccgcgg   10800
acttttgcgg cctgtttctg atgaccgaca acaagcggc gctgccgtat gcatcggcct    10860
acaaacagga cgagcaagag attaaacgct tgttagttga ggcagggatg gaaaccagcg   10920
gcaatttcaa cgaaccggca gatcatctgg cgatctatct cgaattgctc agccatctgc   10980
atttttcgct gggagagggg accgttcctg cgcgaagaat cgacagtttg cggcaaaaaa   11040
cactgacggc gctgtggcaa tggttaccag agtttgttgc gcgttgtcgt cagtatgaca   11100
gctttggttt ttacgcggca ctaagccagt tattgctggt gttagtggag tgcgaccacc   11160
aaaacagata acgtcgtttg tgcgcctgaa aagacgcgtt tagcgtcgca tcaggcatta   11220
tggcgcagtt gccggatgcg gcgtgaacgt cttatccggc ccacaggaac tgtaa         11275
```

<210> SEQ ID NO 40
<211> LENGTH: 11710
<212> TYPE: DNA
<213> ORGANISM: E. coli
<220> FEATURE:
<221> NAME/KEY: misc_feature
<223> OTHER INFORMATION: AE 000202

<400> SEQUENCE: 40

```
ttatggcgca gttgccggat gcggcgtgaa cgtcttatcc ggcccacagg aactgtaatc     60
tttgtagacc ggttaagatg cgtcatcgca tccggcaaac acacatcacg gatgagctac    120
aaaccgggaa agccgctggc gcagcaggcg gttttcctgc ttcaggtgcg caatatcatc    180
cattaacgtc agcgccaccg cgatcccgg ccagtccaga gccagttcat gacgcaggcg     240
taccgcgcgt tgcaccacaa tggcggcatg gtcgtcaaat acccaggttg tttcctggat    300
ctcacgcggt tcaaccaccc ccaaaccgac aatttcattc aactcctctt cagagatgcc    360
ggtatgcagg caaaattcgg taatagtaaa agtcaccgta acattagcca ttatgctttc    420
ccccaatctt tacgtggatc aaaagacgac tgggcgtctg ccagttgctg ccacagcgcg    480
gcagtgtttt catccggttt cggcggcatc acgattttca gtaccgcata cagatcgccg    540
gtctgttttt tgctcaccag accttttgcct ttaacgcgca atcgttgccc ggcctggctg   600
cctggcggga tagtcagcaa aatgctttct ttcagtgttg aacggtgac tttagcaccc     660 agcgccgctt cccacgggct aaccggcacc acaatttcca gatcctggcc gacaatatca    720
aacagcggat gtggcgcaat atgaatcacc agccacaaat cgccatttgg accgccgttt    780
tcgcccggcg tcccctggcc tttcagacgt atgcgttgac cattgccgac gcccgccggg    840
atcttcacat tcagcgtttt cggaatttcc tgttcgatca tgccaaaggc gttataaacc    900
ggcaggttat agctgatggt acgcttatgc tcagtaagcg tttcttcgag gaataccgcc    960
acttcgattt caatatcgtg gccgcgtgtg cggggcgtt gacggctctg gcgggcatgc    1020
```

-continued

```
tgaccgaaaa ttgacgagaa gatatcgtca aaatcttcgg cgttaaaact ctgaccgtcg   1080
ccatggtgga actgacggtt aaattgcgga tcgttgcgat gttgccacat ctgatcatac   1140
tcagcgcgac gttgttcatc acttaacact tcccaggctt cagcgacctc tttgaagcgg   1200
gcttcggcat ccggttcttt gctgacatca ggatggtatt tgcgggcaag tcgacgatag   1260
gcggtcttga ttgtcttgag atcgtccgtc ggtttcacgc ccatgatggc gtaataatcc   1320
tttaattcca tagcgttatc tcgcgtaaat caacacaaat tgaaggaacc cctgtaaggt   1380
aactcctata agtgtagggt aatcctcaaa atttcatatg ccaacacaga atatgttatt   1440
gaaatcatcg cggagaggag gtcgccatca agatggggtg ctgaacatat tttaaacagg   1500 tgaaaaggg tgagcgattt ttgatagttg aaccaggcac tttaagttta actagggcgt   1560
cattatttat taaattttat agacgctata tatgggtagt aatatacatg gaattagttg   1620
cactgcaaat aattatttga aacaggcctg gaacgatata aaaaatgagt acgaaaaaaa   1680
tcaaacatat tcaatcacgc ttttttgaaaa cacactggtg tgttttatgc ggttatacaa   1740
tgaactcaga cgtaaagtaa atgaagagga tactccatgt ctggaatgtg aatcactaga   1800
aaaagaattt gaggaaatgc agaatgaaaa tgatctatca ttatttatga gaatattgcg   1860
tactaatgat acacaaattt attcagggg ttcaggaggt attacatata ctatacaata   1920
tgttcgagat attgatattg ttagagtgtc cttgccgggc agagcttcag agtctatcac   1980
agattttaaa ggttattatt ggtataactt tatggagtat attgaaaaca ttaatgcgtg   2040
tgatgatgtt ttttctgagt attgtttttga tgatgaaaat ataagtgtcc agccagagcg   2100
gataaatacg ccgggaatat ctgatttgga ttctgacatt gatttgtctg gtatatcttt   2160
tattcagcgt gaaactaacc aggcattagg attaaaatat gctcctgtag atggcgatgg   2220
atattgtctg ttaagagcta tactggtttt aaaacaacat gattattcat gggcgctggt   2280
cagttataag atgcaaaagg aagtttacaa cgaattcatt aaaatggttg ataaaaaaac   2340
gatcgaggct cttgttgata cggcattcta taatctcagg gaagatgtaa agacgttatt   2400
tggcgttgat ctacaatctg acaaccaaat tcagggcag agtagtctta tgtcatggag   2460 cttctctgttt tttaaaaaac aattcattga tagttgcttg aataacgaaa aatgtatcct   2520
gcatttaccc gagtttatat ttaatgataa caagaacttg cttgctttag ataccgacac   2580
gtcggatagg attaaagcgg tgaagaattt tcttgttgtt ctttcagata gcatttgctc   2640
attatttatt gttaatagta atgtggcatc aatctccttg gggaatgaat cctttttcaac   2700 agatgaagat cttgagtatg gttatttaat gaacactggc aatcattatg acgtttacct   2760
ccctcctgaa cttttttgctc aggcttacaa gttaaacaat aaggaaatga atgcgcaact   2820
cgactattta aatcgttatg caatttaatg gcaaaggcat atgctaaaaa ccattgttat   2880
tagtctcaca cttttttatt ggtaaatatt gtctctgtat tggtaacgcc gcagatattc   2940
tgtttagcca caggtgcaat tatcagcggc gtacgcgagg caggggctaa tcaggcatag   3000
tttgcgtcaa accttgcctg ttttttgaaga tgtatataga aaaacaggcg ttcaacaagc   3060 catttttgcga acctgttccc ggaaaaaagt catatttctg tcacactctt tagtgattga   3120
taacaaaaga ggtgccagga atgaacaaaa cgctaatcgc cgcagctgtg gcagggatag   3180
ttttactcgc ttcaaacgct caggcacaaa ccgtaccgga aggctatcag ctacagcaag   3240
tgctcatgat gagccgccat aacttacgtg cgccgctggc gaacaatggc agtgtgctgg   3300
agcagtcgac gccgaataaa tggccagaat gggacgtccc cggtgggcaa ctcaccacca   3360
aaggtggcgt gctcgaagtg tatatgggcc attacatgcg tgaatggctg gcagagcagg   3420
```

```
ggatggtgaa atcggggaa tgcccgccgc cgtacaccgt ttatgcctat gccaatagtc    3480
tgcaacgtac cgttgcgacc gcacagttct ttattaccgg cgcattcccg ggtgtgata    3540
ttcctgtgca tcaccaggaa aaaatgggca ctatggaccc aacctttaac ccggtgatca    3600
ccgatgattc cgccgcattc agtgaacagg cggtggcggc aatggagaaa gagctcagca    3660
aactccagct taccgacagc taccagctac tggaaaaaat cgttaactat aaagattccc    3720
ctgcctgtaa agagaaacaa cagtgttcgc tggtggatgg caaaaatacc tttagcgcca    3780
agtatcaaca agaaccaggt gtttccgggc cgctgaaagt cggcaactcg ctggtagatg    3840
cgtttacttt gcaatattac gaaggttttc cgatggatca ggtggcctgg ggagaaatca    3900
aatctgacca gcagtggaag gtgttgtcga agcttaaaaa cggctaccag acagcctgt    3960
ttacctcacc ggaagtggcg cgcaatgttg cgaaaccgct ggtcagttat atcgacaaag    4020
ctctggtcac cgatcgcacc agcgcaccga aaattacagt gttggttggg cacgactcca    4080
acattgcctc tctgttaacg gcgctggatt tcaaaccgta tcagttgcat gaccagaacg    4140
aacgcacgcc gattgcggc aaaatcgttt ccagcgttg gcatgacagc aaagccaatc    4200
gcgatttgat gaaaattgaa tatgtgtatc agagtgcgga acagttacgt aatgccgatg    4260
cgttaaccct gcaggcacct gcgcagcgtg tgacgctgga attaagcggt tgcccgatag    4320
acgctgatgg tttctgcccg atggataagt ttgatagcgt gttgaatgaa gcggtgaaat    4380
aacagaaaac tcccccgcga gaagcggggg agtcgctggt taaacgtttt tacgttcgat    4440
ggtctgttcg ccccaaaaaa gcgaatcttt atcggtctta gcaaaggctt tgactaacac    4500
ttcatcacta ccttcttccc aaatcttttc cgccattttt tcgtcgtacc cggcgacttc    4560
gaaaatggcc tcggctattt ccggcgacgt attgcgcaga gatgcccatt caccgacgtg    4620
atgagctttc gcttcttgag ttggcatgcg tatcctcctg ttgaagatta gccgttaagt    4680
ttaactgcca gacctgcgac atattcccct tgataacgag caatagacag ttcttcctgg    4740
ctgggctggc gtgaaccgtc accgcctgcg atggtggttg cgccgtacgg cgtaccgccg    4800
cgaacctgtg aaacgtcaaa taattcctgc gctgcgtagc caatagggac aattaccatg    4860
ccgtgatgcg caagggtcgt ccaggtggat gtgatggttt gttcctgacc gccgccagta    4920
ccggtggaac taaagacgct cgccagtttt ccgtatagtg cgccggaagc ccacaggccg    4980
cccgtctggt cgaggaaggt acgcatttga ccggacatgt tgccaaagcg ggtaggtgta    5040
ccaaaaataa tggcgtcgta atcggccagt tcttgcgggg ttgcaaccgg tgcagtttgc    5100
gttttaccgc ctgcttttc aaataattgc ggcggcatgg tttccggtac acgcttaacg    5160
acaacttcag cgccatccac tttgcttgca ccctcagcga ctgcgcgtgc catcgtttca    5220
atatgtccgt acatggaata taaagcacc agaactttag ccatttctaa ccactcctcg    5280
tgttatctct attccgtagc gattcgctac cacttattta agataagac gtccttttca    5340
gagtgcaaat ttcacaacca cttatttgat ttataacaac tttcacaagc acgtaatttt    5400
gtcgcaaaat gacacatttt tatctcatcg cgtttttta atcataagag cggcttatgg    5460
ataattattg gagatgatat ctattctcgc taagaagctg ttgcaggata ttaccaaacg    5520
cgggtctgcc cgcgtcagtt cactaagctt agtcccacgt agcgaaaata tggcagccgc    5580
catacgccgc gttaattcta tgcaatatga tgtctatacc cagacggagg tcagtaatgg    5640
caaaccatcg aggcggttcc ggcaattttg cagaagaccg cgaaagagca tcagaagcag    5700
gtaaaaaagg tggacagcac agcgggggta atttcaagaa tgacccgcag cgcgcatctg    5760
```

```
aagcaggtaa aaaaggtggt aagagcagtc acggcaaaag cgacaactag ccgggctaat    5820
caatgacgaa tgcattttg  tctgtagctc gtcaaaaagc catcaccgcc ggttacccgg    5880
tggttgatac tgatgacaaa tgtaagcttg cctgatgcgc gatgcttatc aggcctacca    5940
gaagattgca atatattgaa tttgcactgt tttgtaggcc ggataaggcg tttacgccgc    6000
atccggcatg aacaatgcgt acgttgtcaa caatctgcac cgccggtaac cccggcggtt    6060
ttctgtttat ggctcctgat gaacaacttc tggcggtgga acgtcaacca actttctgct    6120
taacaacgca ttgagtaaaa tcgcgccaaa ggttgctgta ccaatccctc caacgtaaa     6180 accgcccagc gtgagagcaa aatcacccgc gcccagcact aaggttactg cgaccataat    6240
caaattaccg ttctggctta aatcgacacg gttttgtacc catatccttg cgcctgcgac    6300
ggcaatcagc ccgaacacaa caattgatgc accaccaata accgcggccg gaatggtatg    6360
aatcagcgca ccaaatttcg gtgaaaagcc caacagcatg gcgatgacgg cagcagcaac    6420
aaacaccagc gtcgagtaga cttttggtcac ggccatcaca ccgatatttt cagcataggt    6480
ggtcacgccg ctaccgccga cagagccgga aagcatcgtt gccagaccat cgcctacgaa    6540
tgcccgcccc atatacgggt ccatattgcg tccggtcatc ccggcgactg ccttgagatg    6600
acctaagttt tccgccacca gaatcaccgc cacgggcgca atcagcatca ttgcctgacc    6660
attaaaagca ggagtggaaa aatgtggcag accgaaccag gcagcatggc tgacgagagt    6720
aaaatcgacg gcttttccca gccctaaaac gttggtcatc acgccataca gcagacaggc    6780
gacaattaat cctacgagaa tcaataaccg ctggatcatg ccacgggtaa acaccgccac    6840
cagcccaata cacagcaccg tcattaccgc catccagcta tcaaaggccg aagccgatac    6900
acttttcact gcgataggcg ctaagttcag gccaatcgcc atcaccaccg cacccgtcac    6960
caccggcggc atcagtcgtt caatccagcg cgtaccgatt ttcatcacca ccaggccaat    7020
gacggtataa accagcccac aggcgataat cccgcccagc gcaatgctga tattcgggtt    7080
aatgccctga ccgttaaagc ccgtcgcggc gatcaccacg ccgacaaaag ccgcgctgga    7140
gccgagataa ctggggacgc gcccgccggt aataaagaaa aacagtaacg tgccgatccc    7200
cgacattaaa atggaaagat tgggatccag ccccatcaga atcggcatta acaccgtcgc    7260
gccaaacatc gccaccgcgt gttgaacgcc cattactgcc gtctgagcaa acggcaatcg    7320
ttcatccggc gcgaccacgc cgctctctgt agaggtcgat tttaactgcc agtgaggaaa    7380
accgaacatt gccatcagct gtctccttaa ggaggttaac aagcaggcg  catcagcgcg    7440 tgataactgc gatcgaacca caccagcccg tagggtgtgg tgtgacgatg aatcgcttcg    7500
atggcgcaaa acagaatgtc gtgggtgccg acgctcacca cctggctgat acggcagtca    7560
aacgaaacca gagcctcttc cagttgcggg catccggtca cccccgtctg ccagcgggcg    7620
gcggcaaagc ggtgttccat gggcgttttg ccgccaaaaa ggtttgaaag cggctcctgc    7680
ccggcgctaa gtgtatttac acacagcgtt cgatttcat  tgaatgccgg ccagacggac    7740
gccccacgat tcaggcacac cagtaatgtg ggcggcgtat cggtcacact gcagacggcg    7800
ctggcggtga accggcgcg  cccggctgga ccgtccgtgg tgataatatt gaccgccgcg    7860
cccatgcagg acatcgcatc gcgaaaagtt tgttgatcga caatgttcat agtttgctcc    7920
ttacaacagc ccgcaggctt cttcaaagga cagacgtggc aggcgcgcat aaagcttgct    7980
gctatcgcca tagccgatat taatcagcag attgctcttc agcgtgctgc ccgtaaaaaa    8040
ggcgtcgtcc acgtgttgac ggtcaaagcc cgacatcggg ccggtatcca gtcccagcgc    8100
ccggcaggcg acgatcagat aggccgcctg catggaactg ttgcgaaacg ctgtttcttc    8160
```

```
ggcaagttgt gggctggagg taaaccaact gcgggcatca ccgtggggaa acagtagtgg    8220
taaccgttca taaaattcac tgtcccaggc gacgatagcg gtgacgggcg cggtcagggt    8280
tttttgcaga ttgccgctgg aaagtgccgg gcgcagacgt tcttttcctt ctgccgtgcg    8340
ggtaaacacg atccgtgccg gagaacagtt agctgatgtc ggcccccatt tcatcagggc    8400
ataaatctcc cgtaacgtct catcgctgac gggtgtctcc cgccagccgt tgtgagtgcg    8460
ggcatcggtg aacagggtgc taagcgcacc tgggctaacg gcttcgttca tagcaattcc    8520
ttacagggcg gcttcacggt gatgtaacag gctggcaagc ccgttgagta acagagcatt    8580
aaacgtttcg ggatcggtca cgttgcaggc gtgtccgcca tagggcatca ccattttctg    8640
gctatcgggc agggcggcat gaagttcact ggaacatgct gttggcacca gcagatcatc    8700
actggcgcag atgatttgca ccgggcagcg gatgcgatcc gcatggtgac taaagtcagc    8760
gcgtttgagg gcgttaagtc gacgcagtaa attattttg ccctgaaaat gcgccagtgc     8820
cagcgcgtct tctgcctcca ggcgaggtgc gcgggccgcc atccagtcgg cgggatagag    8880
gaacaacggc tgcgcttcca cccatgcctg cgcgccgccg ctatacagta atcgttcgcg    8940
aacctgaaaa cagcggcgcg tatgggcgtt tattcgtagc cagccgttaa cgctgatcag    9000
cacagttacc gacgcgggat aatccagcgc cagctgcatt cccaccagcg caccgagcgc    9060
atggccgacc actgcgtaat gctcaatccc tgcggctacc agcgcctgat gcagttccgc    9120
tgccatctgg gcgatactgt aatcttctgc cagcgtgtcg ggattattgc cggtgccgcg    9180
ctggtcgtaa cagactacct gatactcctg ctccagcacc gccagttgcg gtaaccagta    9240
actgccgcta cccccaagac ccgaaatcaa caccactacg ggcgcatcag cataaggggg    9300
aggtgagagt gaaagtttca tcgcggcctc acttggcgat atgcgcaatt gtggcgattt    9360
ccaccagcgc gtcaggtttt accagtccgc actgaatgca gaatcgcgcc ggtttatcac    9420
ccggaaaaaa ctcggcgtag atttcgttaa tcgcggcgta attttccag tcggtaataa    9480
agatgctgtt gaaggtcaca tccgccatcg tgccacccgc cgtctcgatc accttgcgga    9540
tagtttccag aacgtggcgg gttttgcgcct ttgggtcatc ggcaaacagc acgttattat    9600
gttgatcaaa agccagcgta ccggagacat acaccacgcc atcagccagc gtgccgggaa    9660
cgaaggggc cagcggtgcg ctgctgccag cgggaataat tacggatttt ggcatcgtta    9720
aactccttaa gcgatatgag caaaggacgt gggagaaagc gcgtcgcaga atgtttcgac    9780
gtcgctgacc cagccaaaaa aggtttcgat attgaacaac gcggctttct gcgcaaattt    9840
cggccccgcc tggtgagttg cgtcttcaag caccacgccg aaatactcca gaaaaaagcc    9900
gtcgcgtagc gtcgattcga cgcagacgtt ggtagcgatg ccggtgaaaa ccagatggcg    9960
tattccgcgg ctgcgcaaaa tgctgtccag cggcgtattg aagaaaccgc tgtagcgcgg   10020
cttcggcagc acaatatcgc caggctgcgg caccagttca tccaccagtt gataatccca   10080
ggagcctttc gccagcaatt tcccctgcag ctgcggctgc ttacgcatgg ttttcagggc   10140
gttcgattta tgaaaattcg gtgagccggg tccgccagcc tcgacatact gttcatccca   10200
gccattttga aaccagatga tcagcatccc tgccgctcgc gctgcggtca cggcggtttg   10260
aatgttggca atgaccgggc gagtggttga gacatcaaac ccggcgagat ctaagtagcc   10320
gcctggcgtg gcataagcgt tttgcatatc caccacgatc agcgcacttt gctgcggatc   10380
gaaggtaatg gcttccggtc gagcggttaa ggtcgtcatc atgccacctc ctgagtcagc   10440
gcaggtagat gggcgcggca ttgcatcagt ggttgaatgc gctcgccgaa ggtttcgatt   10500
```

-continued

| | |
|---|---|
| cccgacagaa aatcgtcgaa ggttaacagc acgccttcgg caccaggcac gcttgcgact | 10560 |
| tcatctaaca tgcgcgcgac actggcgtaa gaaccgacta acgtccccat attgatgttt | 10620 |
| accgccgaag tgggatcggc catctgacga acgttggtgt cagtaccgga gcgggtatct | 10680 |
| ttctgacttt gttcggttag ccagcttaac gcctcttcat ccgcgcccgc tttgtagtgt | 10740 |
| tcccatttgg cgcgagcggc atcgtcggtt tcatcggcaa tcaccataaa caacacataa | 10800 |
| gagccaacgt cgcgtccggt ttgctctgcg gcctgtttca tccgcgcagc ggtcggggcg | 10860 |
| aaagccgtgg gtgtatttac gcctttgccg aaacagaagt tgaaatcggc ataccgggcg | 10920 |
| gagaacgcca tgccagcgtc gctttgcccg gcgcagatca cttttcatggg gacactcggt | 10980 |
| tgcggactca cgcgacaatc attcatggtg aaaaaatcgc ctttaaaatc gcttttcccc | 11040 |
| gtgccccaca ggtcgcgcag cacctgaaca tattcggtga gatagtcgta acgacggag | 11100 |
| aaatagtcat cgccaggcca gatacccatc tgctcatact cgggcttttg ccagccagtc | 11160 |
| acgaggttga cgccaaaacg cccgccagag atggagtcga tggttgcggc catacgggcg | 11220 |
| acgattgccg gaggtaacgt taaggtggca gcagtggcgt aaatctgaat gcgcgaggtc | 11280 |
| acggccgcca gccccgccat caaggtgaac gactcaaggt tgtgatccca gaactcagtt | 11340 |
| ttgccgccaa agccacgcag tttgatcatc gacagggcga aatcgaaatg gtagtgctcc | 11400 |
| gcttttgca caatggcttt attcagttca aggtcggca tgtactgcgg cgcgtgggtc | 11460 |
| gaaatgagcc agccgttgtt gccaataggt acgaatacgc caattttcat catcaacctc | 11520 |
| tcttcgtctc gtaaagtgaa agtcagacgg ggcgctgcat cctgcatatc cttttcagcc | 11580 |
| gcgtattggc ttgtttgcaa agcggatgcc agttttttaaa aagttaatgt tattaatctg | 11640 |
| ttaacattac gttatctaaa atatctggta aaagtggac taaacggtca aaacagttgc | 11700 |
| acataaaaca | 11710 |

<210> SEQ ID NO 41
<211> LENGTH: 10751
<212> TYPE: DNA
<213> ORGANISM: E. coli
<220> FEATURE:
<221> NAME/KEY: misc_feature
<223> OTHER INFORMATION: AE 000203

<400> SEQUENCE: 41

| | |
|---|---|
| tatctaaaat atctggtaaa aagtggacta acggtcaaa acagttgcac ataaaacatg | 60 |
| catctgtgcg cgatgagagt gcagaaggtc gaggccgggc gggggttttg ctatcctgtt | 120 |
| gccaatctac aagaggggag agcgcatgac gcaaggcgca gtgaaaacaa cgggtaaacg | 180 |
| ttcgcgcgca gtaagcgcga agaaaaaagc gattcttagc gcagcactgg cactttttc | 240 |
| acaattcggt tttcacggca caaggctgga gcagatcgca gagttggcgg gtgtttcaaa | 300 |
| aaccaatctg ctgtattact ttccgtcaaa agaggcgctg tatattgccg tgctgcggca | 360 |
| gattctcgat atctggctgg caccgttaaa agcgtttcgt gaagatttcg ccccgctggc | 420 |
| ggcgatcaaa gagtacatcc gtctgaagct ggaagtctca cgcgattatc cgcaggcttc | 480 |
| gcgcctgttc tgtatggaga tgctggcagg cgcgccgctg ttaatggatg aactgacggg | 540 |
| cgatttgaag gcattaattg atgagaaatc ggcgctgatt gccggttggg tcaaaagcgg | 600 |
| caaactcgcg ccgattgatc cgcagcattt gatttttatg atttgggctt ccactcaaca | 660 |
| ttacgccgat ttcgcccctc aggtggaggc ggtgacaggc gcgacgttgc gcgatgaggt | 720 |
| attttttcaat caaacggttg aaaacgtgca gcggattatt attgagggga ttcgaccacg | 780 |

-continued

| | |
|---|---|
| ttaaagatgc cggaggaggt tgtaacatcc tccggctacc tgtttaacct atagtcatta | 840 |
| agctggcgtt accgccagcg gcagcggtat tcacactcag cgaacgctcg atatacagcc | 900 |
| gttccagaag gatattgctt tcgccacggg caaaaccctg caccgaaaca attgtgccat | 960 |
| cccgcgcggc aactgcttca cacaatgcgc gaagctgatc cgaatcaccg tggaagatca | 1020 |
| ccgcatcaaa cggttgagcg gttatatttt ccgctttcgc cagttgaata cgttcgctga | 1080 |
| ctgccgatgg caatgccttc actaactgac gatgcagcgc gtcatccggc cacagtacct | 1140 |
| ggctgcccac cgccagcacg gcggcgagct gagtcagcgc atcctgctca tcatcggcaa | 1200 |
| tacacaacac gcgctcacgc ggcagcagcg tccaggtgtt gcgttcaccc gtcggccccg | 1260 |
| gcagcaatcg ttgtgttcct gcctgcgcca gctcgccata ttgcgtacat aacgcctgca | 1320 |
| attctggacg atttgctgcc cattcccgca gtgcatttag cggctgagtc aatgcggctt | 1380 |
| tcaactgcgc atcgaccgga tactttgcat cctgacgcgc gagcgtcact gccagcgcac | 1440 |
| tttccgggcg attcgccagc agacggtaga gatagagcgg accgcctgct ttcggcccgg | 1500 |
| taccggacaa cccttcgccg ccgaacggct gcacaccaac cactgcgccc accatattac | 1560 |
| ggttaacata caggttacca acatgggccg agccagtgac ctgggcgatg gtttcatcaa | 1620 |
| tgcgcgtatg gacgccaagc gtcagaccat aaccggaagc gttaatctgc tcgatcagct | 1680 |
| ctggtagctg gttacggttg taacgcacca catgcagcac cggaccaaag acctcttttt | 1740 |
| gcaattcggc aaagtcatcc agttcgatca gcgtcggggc gacaaaggtg ccgcttttgcc | 1800 |
| attcacgggc atcttcgctg ttttcccgca ccgcctggaa caccgacgg cctttgctac | 1860 |
| gcatggtctg aatatggcgc tcaatattgg ctttcgcttc gctatcaatc actggaccga | 1920 |
| tatcggtggt caggcgaccc ggattaccca tccggcattc ggccattgcg ccgcgcagca | 1980 |
| ttttcaacgt gtggtcggca atctcatctt gcaggcacag cacgcgcagc gccgaacaac | 2040 |
| gctgaccccgc actgtcgaac gccgaggcca gtacatccac gacgacctgt tcggtcagtg | 2100 |
| ctgaagaatc gacaatcatc gcgttcatgc cgccggtttc agcgatgagc ggaatagggc | 2160 |
| gaccctgagc gtccaggcgg ctggcgatat tgcgctgcag taacgtagcg acttcggttg | 2220 |
| aaccggtaaa catcaccccg cgcacgcgat catcacccgt cagttgcgcg cccacggttt | 2280 |
| cacccccgacc tggcagcaat tgcaccacgc ctggcggtac acccgcttcc agcaaaatgg | 2340 |
| cgatcccttg cgcggcaatc agcggcgttt gttctgccgg ttttgccagc acgctgttac | 2400 |
| ctgccgccag tgcggcggcg atctgcccgg tgaaaatagc cagcgggaag ttccacggac | 2460 |
| tgatacacac cacaggccct aatggacggt gggtttcgtt agcgaaatca tcccgcacct | 2520 |
| gtccggcgta gtagtggaga aaatcgaccg cttcgcgcac ttcggcaatg gcgttactga | 2580 |
| aggttttttcc ggcctcacgc accagaatac caatcagttg ctgcatctgg ctttccatca | 2640 |
| gcacggcagc gcggtgcaaa atcgctgcgc gttcagccgg aggcgtggca aaccagattg | 2700 |
| gcgcgttatt aaccgcactt tccagcgcct gttctacttc acgcggcgtg gcttcacgca | 2760 |
| catagcccac aatatctttc ggttccgcag ggttaataac gggcgacatc tcacctgccg | 2820 |
| ctaccggttg ttccagcatt ggcaaggcct gccattttg cagtgcacta ttgagcaggg | 2880 |
| cagaggagag cgaggccagg cggtgttcgt tagcgagatc cagccctgcc gagttgtcgc | 2940 |
| gcccgtgacc gtaaagatcg cgcggcaggg gaattttcgg atgcggtaat ccagtttgcc | 3000 |
| cttcctgttg cgccagtttt tctacagcag tgaccggatc ggcgaccagt tcatccagtg | 3060 |
| gcaaagaggt gtcggcaata cggttaacaa acgaggtgtt agcaccgttt tccagcaggc | 3120 |
| gacgcaccag atacgccaac agcgtttcat gtgtgccaac cggagcataa atacgacacg | 3180 |

```
gacggttaag tttgccgtcg gcaactttcc cggtgacctg ctcatacagt ggctcgccca   3240
taccatgcag gcactggaac tcgtactgac ccgggtagta gttctgcccc gccagttgat   3300
aaatcgccgc cagcgtatgg gcgttgtgcg tcgcgaactg cgggtagatt agattcggca   3360
ccgccagcag cttttcgca caggcgagat aagaaacgtc ggtatacacc ttgcgggtat   3420
aaaccggata accttcaagg ccgtccatct gcgcacgctt aatttcacta tcccagtacg   3480 cgccttcac caggcgaatc atcagacggc gacggctgcg ggtggcgaga tcaatcaggt   3540
aatcgatcac caacgggcag cgttttgat aagcctgaat aacaaaaccg atgccgttcc   3600
agcctgccag ttccggctcg aaacagagtt tttccagcag atcgagggag atctccaggc   3660
gatcggactc ttccggcgtca atgttgatac caatatcgta ctgacgcgcc agcagggtga   3720
gtgatttcag acgcgggtaa agctcttcca ttacccggtc atactgggcg cggctataac   3780
gcggatgcag cgccgacagt ttgattgaaa tgcccggccc ttcatagatg ccacgaccgt   3840
tagacgcttt accgatggcg tgaatcgcct gctgatagga aaccatatac gcctgtgcat   3900
ctgcggcggt cagcgcggct tcgcccagca tatcgtaaga gtaacggaaa cctttctctt   3960
ccagcttgcg ggcattggct aacgcttccg cgatggtttc gccagtgacg aactgctcac   4020
ccatcaggcg catcgccata tccacacctt tgcggatcag cggttcaccg cttttaccga   4080
taatgcggtt cagcgagcgg gagaggctgg cttcgttatg ggtggaaacc agtttgccag   4140
taaacagcag cccccaggtg gcggcattaa caaacagtga cgggctacga ccaatgtgtg   4200
actgccagtt accgttgctg attttgtcgc gaattaacgc gtcgcgggtg gctttgtcgg   4260
gaatacgcaa caacgcttcc gccagacaca tcagcgccac gccttcctgc gatgacagcg   4320
aaaactcctg caataacccc tggaccatac ctgcgcgacc actggcattt ttttgattac   4380
gcagtttatc ggccagctga tacgccagtt tgtgcgcctg ttcagcaact ggctgcggca   4440
ggcgggcttg ttccagcagc atagaaaccg cttcggtttc cggcggcga taggccgcgg   4500 tgatcgcggc gcgggaaacc gactggggca atatttgctc ggcaaagtcg aggaatggct   4560
ggtgtggttc ctctgccgga gtcggtgctt catcgctctc attggccgcg ccagaaagca   4620
gcgcaggtag ctccggcaga gtatcgctgt tttccagttg ttcgagataa gaaaaaatcg   4680
cctgcttaat taaccagtgt ggtgtgcgat cgatacgtgt cgcggcagac ttaatacgct   4740
cacgcgtcgc gtcgtccagc ttaaccccca tggtggtggt tcccatgcca ttactcctgt   4800
tgttcagaaa ggtgcaactt aacgttatcg tgaaatatcc atgatgttgc aactttgtgc   4860
aaccatgtta aatgtgacat gcgtagcaag cttaaaaatg aatgaaatgt taataaaaga   4920
aatcgatatg acaggatta aaaaaataac tcagactttt tctctgcggc agttaacatt   4980
tttgaaaggt gcaaccgcaa aaaatgtgag agagtgcaac ctgatgaaaa atagtgtcgc   5040
tgagcactaa aatttaatgt aaatggtgtg ttaaatcgat tgtgaataac cagcgcttcc   5100
ggcaggatac ggtcgccctg gtaaaacata aactctgtta ccccgttccg gtggcagata   5160
taacggcaag tttcgacatt gccgataata attttttgga gactttagat ggctattagc   5220
acaccgatgt tggtgacatt tgtgtctat atctttggca tgatattgat tgggtttatc   5280
gcctggcgat caacgaaaaa ctttgacgac tatattctgg gcggtcgtag tcttgggcca   5340
ttcgtgacgg cattatcggc gggtgcgtcg gatatgagcg gctggctgtt aatgggggttg   5400 ccgggcgctg ttttctttc cgggattccc gaaagctgga tcgccattgg cctgacatta   5460
ggcgcgtgga ttaactggaa gctggtggcc gggcggttgc gtgtgcatac cgaatacaac   5520
```

```
aataacgcct taacactgcc ggattatttc accgggcgct ttgaagataa aagccgcatt      5580
ttgcgcatta tctctgcgct ggttattttg ctgttcttca ccatttattg cgcttcgggc      5640
attgtggcag gcgcgcgtct gtttgaaagt acctttggca tgagctacga aacggctctg      5700
tgggcgggcg ctgcggcgac gatcctttac acctttattg gcggtttcct cgcggtgagc      5760
tggactgaca ctgtacaggc cagcctgatg attttttgccc tgatcctgac gccggttatc     5820
gtcattatca gtgtcggtgg ctttggtgac tcgctggaag tgatcaaaca aaagagcatc      5880
gaaaacgttg atatgctcaa aggtctgaac tttgttgcca ttatctcact gatgggttgg      5940
gggctgggtt acttcgggca gccgcacatt ctggcgcgtt ttatggcggc ggattctcac      6000
cacagcattg tccatgcgcg tcgtattagt atgacctgga tgatcctctg cctggcaggg      6060
gcggtggctg tcggcttctt tgggattgct tactttaacg atcatccggc gttggctggt      6120
gcggtaaatc agaacgccga gcgtgtgttt atcgaactgg cgcaaattct gtttaacccg      6180 tggattccg ggattctgct gtcggcaatt ctggcggcgg taatgtcaac cttaagttgc       6240
cagctgctgg tgtgctccag tgcgattacc gaagatttgt acaaagcgtt tctgcgtaaa      6300
catgccagcc agaaagagct ggtgtgggta ggcgtgtga tggtgctggt ggtggcgctg       6360
gtggcgattg cgctggcggc aaacccggaa accgcgtgc tgggcttagt gagctacgcg       6420
tgggcaggct ttggcgcggc gtttggtcca gtggtgctgt tctcggtgat gtggtcacgc      6480
atgacgcgta acggtgcgct ggcggggatg atcatcggtg cgctgacggt tatcgtctgg      6540
aaacagttcg gctggctggg actgtacgaa attattccgg gctttatctt cggcagtatt      6600
gggattgtag tgtttagttt gctgggtaaa gcgccgtcag cggcgatgca aaaacgcttt      6660
gccgaggccg atgcgcacta tcattcggct ccgccgtcac ggttgcagga aagctaaggg      6720
acttagcctg cggcggtttt gtttggcttc agcagcgggt tgcgctccct taatgtgcct      6780
cgccatataa attgaatggt gcagggagcg cgcaggggc ggccaatcgc cgccgccccc      6840
tgctgtcccg gccttcgggg aacgcttcag cgattttgac gccaccaaca cccgagctgt      6900
tattatgttc cgggcaaaaa gttagatttg ataatcgcgg atggacgaaa ttgcttgata      6960
cacccgctta tcagttttac atggaagctc tgatgcattg agtctggaca gttttgtcgg      7020
ctggatacgg cgtttacgcg gcatccggca agaacacatg gttctttgca acaatccca      7080 tctttctacc ctggaataat cgtttatatc ccttggcatt acctctcttt gtttacattc      7140
caacatcatt ttataaacat tccgcttgtg ttttctttg ccgtaatgat aatcgctatc       7200
actgcgattt acttttcttt gcatagattg actcagaaaa acgtttaagg gtgggtggca      7260
tgtttgttcc gtttctcatt atgttgcgcg aaggacttga agccgcgctg attgtcagtt      7320
tgattgccag ctatcttaag cgtacccagc gaggccgatg gattgtgtga tgtggattgg      7380
cgtgttgctt ccgctgcgt tgtgcctggg cttgggtatc ttcattaacg aaaccaccgg       7440
cgaatttccg caaaaagaac aggaactgtt tgaaggtatc gtggcggtga tcgccgtggt      7500
gatccttacc tggatggttt tctggatgcg caaagtgtcg cgcaacgtca agtgcaact       7560 ggaacaggca gtcgatagcg cattgcagcg tggaaatcat catggctggg cgctggtgat      7620
gatggtcttt tttgccgttg caagggaagg gctggagtcg gtcttttttcc tgctggcggc      7680 atttcaacaa gatgtcggga tctggccgcc gctgggtgca atgctcggtc ttgctactgc      7740
cgtggtgcta ggcttcctgc tctactgggg cggtattcgc ctcaatcttg gtgcatttt       7800 taaatggacc agcctgtttta ttctcttcgt cgccgcaggg ctggcagctg gtgccattcg     7860
cgcatttcat gaagccggat tgtggaacca ctttcaggaa atcgccttcg atatgagtgc      7920
```

-continued

```
ggtgctctca actcactcgc tgtttggcac gctgatggaa gggattttg gctatcagga    7980
agcgccgagc gtcagcgaag tcgccgtctg gtttatttat ctcatcccgg cgctggtggc   8040
atttgctctg ccaccacgcg caggggcgac agcgtctcgc tccgcgtaac aaatacgacg   8100
caaactcttg cttagttaca acatacttta aagggatagt ctcgtcatga ccattaactt   8160
ccgccgtaac gcattgcagt tgagcgtggc tgcgctgttt tcttctgctt ttatggctaa   8220
cgccgctgat gtgccgcagg tcaaagtgac cgtgacggat aagcagtgcg aaccgatgac   8280
cattacggtt aacgccggga aaacacagtt cattattcag aaccacagcc agaaggcgct   8340
ggagtgggag atcctcaaag gcgtgatggt ggtggaagag cgggaaaata tcgcccctgg   8400
ctttagccag aaaatgacgg cgaatttaca gcctggcgaa tacgatatga cctgcggtct   8460
gctgactaac ccgaaaggga agttgatcgt caaaggtgag gcaacggcgg atgcggcgca   8520
aagtgatgcg ctgttaagtc ttggtggtgc aattactgca tataaagcgt atgtcatggc   8580
ggaaaccacg cagctggtga ccgacaccaa agcctttacc gacgcgatta agcaggcga   8640
tatcgaaaaa gcgaaagcac tgtatgcacc gacgcgccag cactatgagc gtattgaacc   8700
gattgctgaa ctgttctccg atctggatgg cagcattgac gcccgtgaag atgattacga   8760
gcaaaaagcc gccgacccaa aattcactgg ttttccaccgt ctggaaaaag cattgtttgg   8820
cgacaacacc accaaaggga tggatcagta cgctgagcag ctttataccg atgtggtcga   8880
tttgcaaaaa cgcatcagtg aactggcttt cccaccttca aaagtggtcg gcggcgcagc   8940
cggactgatt gaggaagtgg cagccagcaa aattagcggt gaagaagatc gctacagcca   9000
caccgatctg tgggatttcc aggctaacgt tgaaggctcg cagaaaattg tcgatttgct   9060
gcgtccacaa ctgcaaaaag ccaacccgga actgctggca aaagtcgatg ccaactttaa   9120
aaaggtcgat accattctgg cgaaataccg tactaaagac ggttttgaaa cctacgacaa   9180
attgaccgat gccgaccgga atgcactgaa aggaccgatt actgcgctgg cggaagatct   9240
ggcgcaactt cgcggtgtgc tgggactgga ttaagcgtta tgcagtataa agatgaaaac   9300
ggcgtgaatg aaccgtcacg ccgacgttta ctgaaagtga taggtgcact ggcgctggcg   9360
ggaagttgtc cggtcgctca tgcacaaaaa acgcaaagtg cgccgggtac gctttcaccg   9420
gatgctcgca atgagaaaca gccgttttat ggtgagcatc aggcagggat cctgacgcca   9480
caacaggccg caatgatgct ggtggcgttt gatgtgcttg ccagcgataa agccgatctt   9540
gagcggttgt ttcgcttgtt gactcagcgt tttgcttttc tgactcaggg cggagcagca   9600
ccagaaacgc caaatccgcg cctgccacca ctcgattccg gcattcttgg cggctacatt   9660
gcgcccgata atctccacat cacgttatcg gtgggtcact cattgtttga tgagcgcttt   9720
ggccttgcgc cacagatgcc aaaaaagctg cagaagatga cgcgtttccc caacgactcg   9780
ctggatgcgc gttatgtcat ggtgatgtg ttgctacaga tttgcgccaa cacccaggac   9840
acggttatcc atgcgctgcg cgatatcatc aaacacacgc cggatttgct cagtgtgcgc   9900
tggaagcggg aagggtttat ttccgatcac gcggcgcgta gtaaaggcaa agagacgccg   9960
attaatttgc tgggtttcaa agacggcact gccaatcccg atagccagaa tgataagttg   10020
atgcaaaaag tggtgtgggt aacggcagat cagcaggagc ctgcgtggac aatcggtggc   10080
agctatcagg cagtacgctt gattcagttt cgagtggaat tttgggacag aacgccgctg   10140
aaagaacagc agacgatttt tggccgtgat aagcaaaccg gtgcgccgct gggaatgcag   10200
catgagcatg atgtgcctga ttacgccagc gacccggaag ggaaggtgat cgcgctggac   10260
```

```
                                                            -continued
agccatatcc ggctggcgaa tccccgcacg gcggagagtg agtccagcct gatgctgcgt    10320
cgtggctaca gttattcact gggcgtcacc aactccgggc aactggatat ggggttgctg    10380
tttgtctgct accaacacga tctggaaaaa ggcttcctga cagtacaaaa aaggctcaat    10440
ggcgaagcgc tggaggaata cgttaaacct atcggcggcg gttattttt tgcgctgccg     10500 ggggtgaagg acgcgaacga ttatttcgga agcgcgttat tgcgggttta atgtttttag    10560
gcggataagg catttgtgcg cagatgcctg atgcgacgct tgcgcgtctt atcatgccta    10620
caatcagtgc gggtttggta ggctggataa ggcgttcacg ccgcatccgg cgatcgtgca    10680
ctgatgcctg atgcaaatcc tgctgaaagc acacagcttt tttcatcact gtcatcactc    10740
tgtcatcttt c                                                        10751
```